(12) United States Patent
Ichikawa et al.

(10) Patent No.: US 9,233,945 B2
(45) Date of Patent: Jan. 12, 2016

(54) COMPOUND, RESIN AND PHOTORESIST COMPOSITION

(71) Applicant: SUMITOMO CHEMICAL COMPANY, LIMITED, Tokyo (JP)

(72) Inventors: Koji Ichikawa, Osaka (JP); Hiromu Sakamoto, Osaka (JP); Shingo Fujita, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 55 days.

(21) Appl. No.: 13/648,038

(22) Filed: Oct. 9, 2012

(65) Prior Publication Data

US 2013/0095424 A1    Apr. 18, 2013

(30) Foreign Application Priority Data

Oct. 12, 2011    (JP) .................. 2011-224682

(51) Int. Cl.
  *C07D 327/04*    (2006.01)
  *C08F 28/06*    (2006.01)
  *G03F 7/039*    (2006.01)
  *G03F 7/20*    (2006.01)

(52) U.S. Cl.
  CPC .............. *C07D 327/04* (2013.01); *C08F 28/06* (2013.01); *G03F 7/0397* (2013.01); *G03F 7/2041* (2013.01)

(58) Field of Classification Search
  None
  See application file for complete search history.

(56) References Cited

U.S. PATENT DOCUMENTS

| | | |
|---|---|---|
| 2009/0068590 A1 | 3/2009 | Dazai et al. |
| 2009/0197204 A1* | 8/2009 | Shiono et al. ............. 430/286.1 |
| 2009/0226842 A1* | 9/2009 | Shimizu et al. ............. 430/281.1 |
| 2010/0086873 A1 | 4/2010 | Seshimo et al. |
| 2010/0178609 A1 | 7/2010 | Dazai et al. |
| 2010/0323296 A1 | 12/2010 | Ichikawa et al. |
| 2011/0117497 A1 | 5/2011 | Sato et al. |
| 2012/0115082 A1 | 5/2012 | Ichikawa et al. |

* cited by examiner

*Primary Examiner* — Anca Eoff
*Assistant Examiner* — Anna Malloy
(74) *Attorney, Agent, or Firm* — Birch, Stewart, Kolasch & Birch, LLP

(57) ABSTRACT

A resin comprising a structural unit represented by formula (aa):

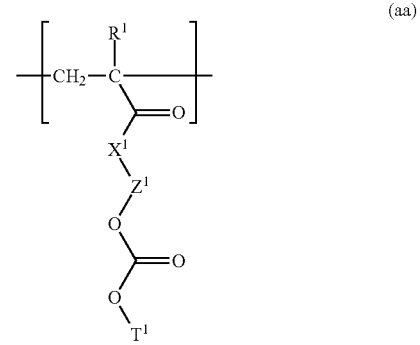

wherein $T^1$ represents a C3-C34 sultone ring group optionally having a substituent,
$X^1$ represents —O— or —N($R^c$)—,
$R^c$ represents a hydrogen atom or a C1-C6 alkyl group,
$Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)—, and $R^d$ represents a hydrogen atom or a C1-C6 alkyl group, and
$R^1$ represents a hydrogen atom, a halogen atom, or a C1-C6 alkyl group optionally having a halogen atom.

9 Claims, No Drawings

COMPOUND, RESIN AND PHOTORESIST COMPOSITION

This nonprovisional application claims priority under 35 U.S.C. §119(a) on Patent Application No. 2011-224682 filed in JAPAN on Oct. 12, 2011, the entire contents of which are hereby incorporated by reference.

FIELD OF THE INVENTION

The present invention relates to a compound, a resin, a photoresist composition and a method for producing a photoresist pattern.

BACKGROUND OF THE INVENTION

A photoresist composition is used for semiconductor microfabrication employing a lithography process. The photoresist composition comprises an acid generator and a resin.

As to a resin for photoresist composition, US 2010/0178609 A1 discloses a resin which comprises a structural unit represented by the following formula;

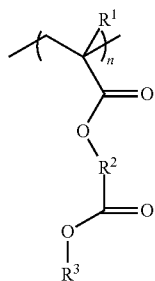

where $R^1$ represents a hydrogen atom, an alkyl group or the like, $R^2$ represents a bivalent linking group containing at least one specific polar group, and $R^3$ represents a cyclic group containing a sulfonyl group within the ring skeleton.

SUMMARY OF THE INVENTION

The present invention is to provide a resin and a photoresist composition comprising the same.

The present invention relates to the followings:

[1] A resin comprising a structural unit represented by formula (aa):

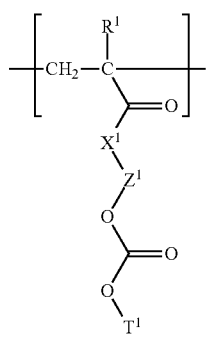

wherein $T^1$ represents a C3-C34 sultone ring group optionally having a substituent, $X^1$ represents —O— or —N($R^c$)—, $R^c$ represents a hydrogen atom or a C1-C6 alkyl group, $Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)—, and $R^d$ represents a hydrogen atom or a C1-C6 alkyl group, and $R^1$ represents a hydrogen atom, a halogen atom, or a C1-C6 alkyl group optionally having a halogen atom.

[2] The resin according to [1], wherein $T^1$ is a C4-C34 sultone ring group optionally having a substituent.

[3] The resin according to [1] or [2], which is insoluble or poorly soluble in an aqueous alkali solution but becoming soluble in an aqueous alkali solution by the action of an acid.

[4] A photoresist composition which comprises an acid generator and the resin according to [1] or [2].

[5] A process for producing a photoresist pattern comprising:

(1) a step of applying the photoresist composition according to [4] on a substrate to form a photoresist composition layer, (2) a step of forming a photoresist film by drying the photoresist composition layer, (3) a step of exposing the photoresist film to radiation, (4) a step of heating the photoresist film after exposing, and (5) a step of developing the heated photoresist film.

[6] A compound represented by formula (aa').

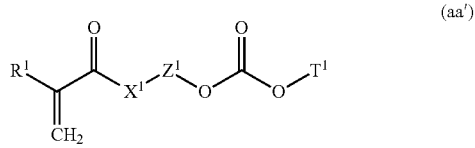

wherein $T^1$ represents a C3-C34 sultone ring group optionally having a substituent, $X^1$ represents —O— or —N($R^c$)—, $R^c$ represents a hydrogen atom or a C1-C6 alkyl group, $Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)—, and $R^d$ represents a hydrogen atom or a C1-C6 alkyl group, and $R^1$ represents a hydrogen atom, a halogen atom, or a C1-C6 alkyl group optionally having a halogen atom.

[7] The compound according to [6], wherein $T^1$ is a C4-C34 sultone ring group optionally having a substituent.

DESCRIPTION OF PREFERRED EMBODIMENTS

The resin of the present invention (hereinafter, simply referred to as RESIN (A)) comprises a structural unit represented by formula (aa):

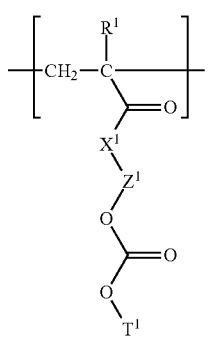

(aa)

wherein $T^1$ represents a C3-C34 sultone ring group optionally having a substituent, $X^1$ represents —O— or —N($R^c$)—, $R^c$ represents a hydrogen atom or a C1-C6 alkyl group, $Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)— and $R^d$ represents a hydrogen atom or a C1-C6 alkyl group, and $R^1$ represents a hydrogen atom, a halogen atom, or a C1-C6 alkyl group optionally having a halogen atom.

In this specification, "sultone ring group" means a cyclic group having —O—$SO_2$— within a ring structure. The cyclic group can further contain a heteroatom such as an oxygen atom, a sulfur atom and a nitrogen atom. As the heteroatom, an oxygen atom is preferable.

The sultone ring group is preferably C4-C34 sultone ring group.

The sultone ring group may have a substituent, and examples thereof include a halogen atom, a hydroxyl group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group and a C2-C4 acyl group.

Examples of the C1-C12 alkyl group include a linear or branched chain alkyl group such as a methyl group, an ethyl group, a propyl group, an isopropyl group, a butyl group, an isobutyl group, a tert-butyl group, a pentyl group, a hexyl group, a heptyl group, an octyl group, a decyl group and a dodecyl group. Preferred is a C1-C6 alkyl group, and more preferred is a methyl group. Examples of the halogen atom include a fluorine atom, a chlorine atom, a bromine atom and an iodine atom. The alkyl group having a halogen atom or a hydroxyl group includes hydroxymethyl group, hydroxyethyl group, and trifluoromethyl group.

Examples of the C1-C12 alkoxy group include a linear or branched chain alkoxy group such as a methoxy group, an ethoxy group, a propoxy group, an isopropoxy group, a butoxy group, an isobutoxy group, a tert-butoxy group, a pentyloxy group, a hexyloxy group, a heptyloxy group, an octyloxy group, a decyloxy group and a dodecyoxy group.

Examples of the C6-C12 aryl group include a phenyl group, a naphthyl group, an anthryl group and a biphenyl group.

Examples of the C7-C12 aralkyl group include a benzyl group, a phenylethyl group, a phenylpropyl group, a naphthylmethyl group and a naphthylethyl group.

The C2-C12 alkoxycarbonyl group is a group formed by bonding a C1-C11 alkoxy group with a carbonyl group, and examples thereof include a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, a hexyloxycarbonyl group, a heptyloxycarbonyl group, an octyloxycarbonyl group and a decyloxycarbonyl group, and a C2-C6 alkoxycarbonyl group is preferable and a methoxycarbonyl group is more preferable.

Examples of the C2-C4 acyl group include an acetyl group, a propionyl group and a butyryl group.

From the viewpoint of easy production of a monomer giving the structural unit represented by formula (aa), an unsubstituted sultone ring group is preferable.

The sultone ring of the sultone ring group may be monocyclic or polycyclic, which is preferably alicyclic ring. Specifically, the sultone ring is preferably a C3 to C34 alicyclic ring which has a bridged structure and —O—$SO_2$—, more preferably a C4 to C34 alicyclic ring which has a bridged structure and —O—$SO_2$—, still more preferably a C4 to C10 alicyclic ring which has a bridged structure and —O—$SO_2$—.

Examples of the sultone ring group include the group represented by the following formula ($T^1$-1), ($T^1$-2), ($T^1$-3) or ($T^1$-4);

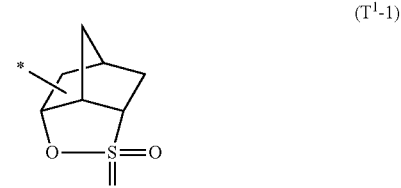

($T^1$-1)

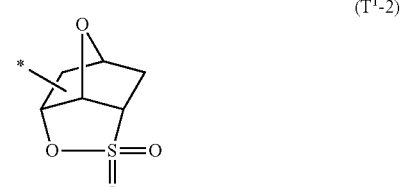

($T^1$-2)

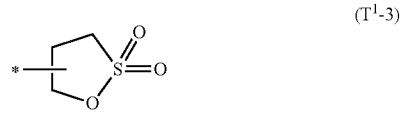

($T^1$-3)

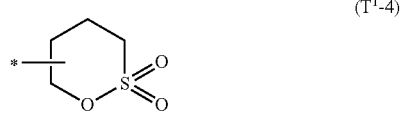

($T^1$-4)

where * represents a binding position to —O—.

It is preferred that $T^1$ is a group represented by the formula (T1):

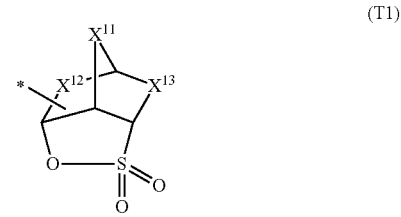

(T1)

wherein $X^{11}$, $X^{12}$ and $X^{13}$ independently each represent —O—, —S— or —$CH_2$—, a hydrogen atom in —$CH_2$— in the formula (T1) may be replaced by a halogen atom, a hydroxyl group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group or a C2-C4 acyl group, and * represents a binding position to —O—.

It is preferred that $X^{11}$, $X^{12}$ and $X^{13}$ independently each represent —O— or —CH$_2$—, and it is more preferred that $X^{11}$, $X^{12}$ and $X^{13}$ are —CH$_2$—. When one of $X^{11}$, $X^{12}$ and $X^{13}$ is —O—, it is preferred that the other two are —CH$_2$—. When one of $X^{11}$, $X^{12}$ and $X^{13}$ is —O—, it is preferred that $X^{11}$ is —O—.

It is more preferred that $T^1$ is a group represented by the formula (T2):

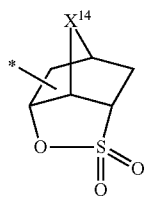

(T2)

wherein $X^{14}$ represents —O— or —CH$_2$—, and * represents a binding position to —O—.

Preferable examples of $T^1$ include the following groups;

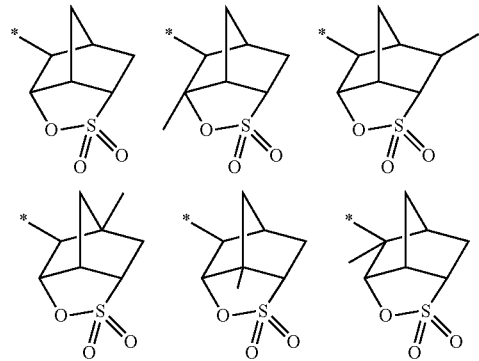

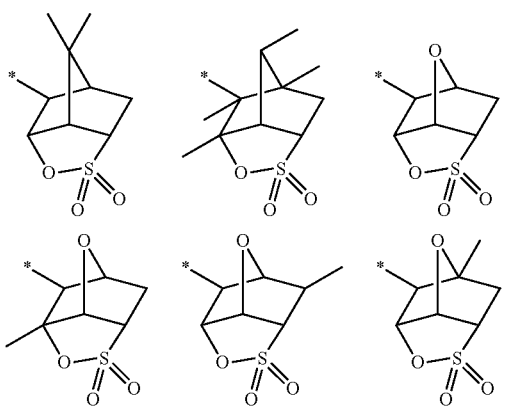

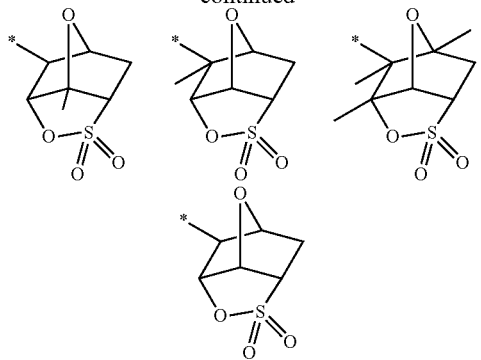

in these formulae, * represents a binding position to —O—.

In formula (aa), $X^1$ represents —O— or —N(R$^c$)—, where R$^c$ represents a hydrogen atom or a C1-C6 alkyl group. $X^1$ preferably represents —O— or —NH—.

In formula (aa), $Z^1$ represents —X$^2$— or —X$^3$—X$^4$—CO—X$^5$—, where $X^2$, $X^3$ and $X^5$ independently each represent a C1-C6 alkanediyl group, and $X^4$ represents —O— or —N(R$^d$)— where R$^d$ represents a hydrogen atom or a C1-C6 alkyl group. Of —X$^3$—X$^4$—CO—X$^5$—, any of $X^3$ and $X^5$ may bind to $X^1$.

Examples of the C1-C6 alkanediyl group include a linear or branched chain alkanediyl group such as a methylene group, an ethane-1,1-diyl group, an ethane-1,2-diyl group, a propane-1,1-diyl group, a propane-2,2-diyl group, a propane-1,3-diyl group, a propane-1,2-diyl group, a butane-1,3-diyl group, a butane-1,4-diyl group, a pentane-1,5-diyl group, a 2-methylpropane-1,3-diyl group, a 2-methylpropane-1,2-diyl group, a pentane-1,4-diyl group and a 2-methylbutane-1,4-diyl group.

When $Z^1$ is *—X$^2$—, a C1-C4 alkanediyl group is preferable and a C1-C3 alkanediyl group is more preferable. $X^2$ is preferably linear chain.

When $Z^1$ is —X$^3$—X$^4$—CO—X$^5$—, the total carbon number of $X^3$ and $X^5$ is preferably 4 or less, and more preferably 3 or less. $X^3$ and $X^5$ are preferably linear alkanediyl groups. $X^4$ is preferably —O— or —NH—, and more preferably —O—.

Examples of —X$^3$—X$^4$—CO—X$^5$— include —CH$_2$—O—CO—CH$_2$—, —CH$_2$—CH$_2$—O—CO—CH$_2$—, —CH$_2$—CH$_2$—CH$_2$—O—CO—CH$_2$—, —CH$_2$—O—CO—CH$_2$—CH$_2$—, —CH$_2$—NH—CO—CH$_2$—, —CH$_2$—CH$_2$—NH—CO—CH$_2$—, —CH$_2$—CH$_2$—CH$_2$—NH—CO—CH$_2$—, —CH$_2$—NH—CO—CH$_2$— and —CH$_2$—CH$_2$—NH—CO—CH$_2$—. Preferred is —CH$_2$—CH$_2$—O—CO—CH$_2$—. More preferred is *—CH$_2$—CH$_2$—O—CO—CH$_2$— where * represents a binding position to $X^1$.

It is preferred that $Z^1$ is *—X$^2$—, and it is more preferred that $Z^1$ is an ethane-1,2-diyl group (an ethylene group).

$X^1$ is preferably —O— or —NH—.

The structure represented by —X$^1$—Z$^1$— is preferably —O—CH$_2$CH$_2$— or —NH—CH$_2$CH$_2$—.

$R^1$ is preferably an unsubstituted C1-C6 alkyl group or a hydrogen atom, more preferably a C1-C3 alkyl group or a hydrogen atom, and especially preferably a methyl group or a hydrogen atom.

The structural unit represented by formula (aa) is preferably represented by the formula (aa1).

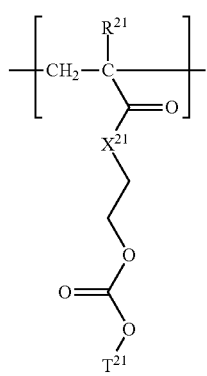
(aa1)

wherein $T^{21}$ represents a C3-C34 sultone ring group optionally having a substituent, preferably C4-C34 sultone ring group optionally having a substituent, and more preferably C4-C34 sultone ring group, $X^{21}$ represents —O— or —NH—, and
$R^{21}$ represents a hydrogen atom or methyl group.

Examples of the structural unit represented by formula (aa) include the structural units represented by the formulae (aa-1) to (aa-21).

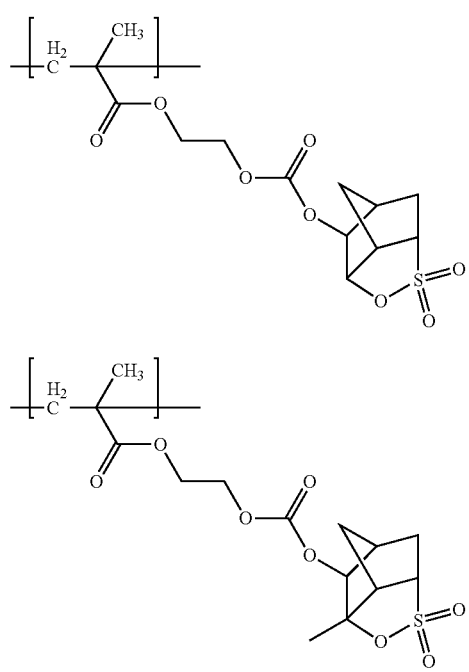
(aa-1)

(aa-2)

(aa-3)

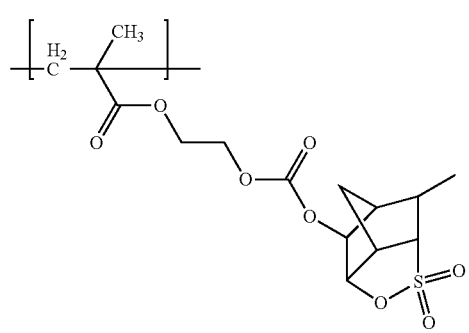

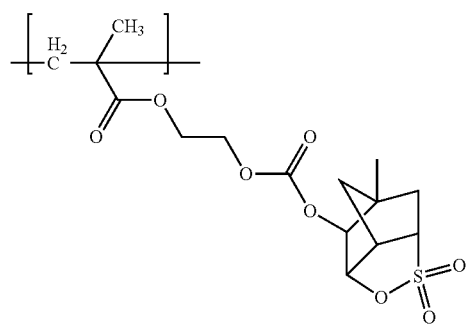
(aa-4)

(aa-5)

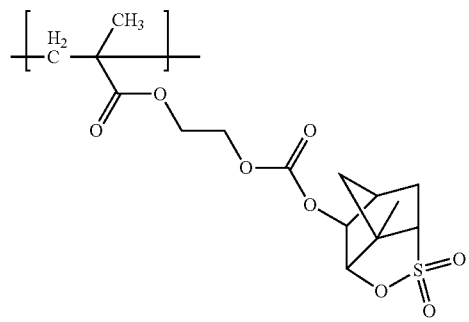
(aa-6)

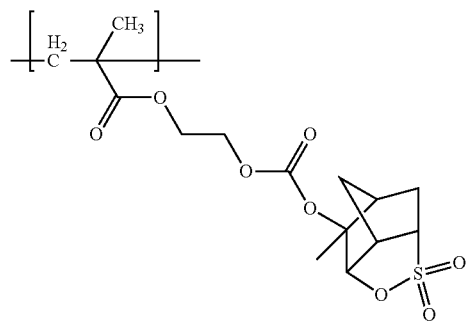
(aa-7)

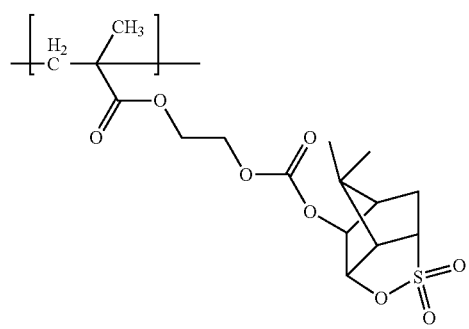
(aa-8)

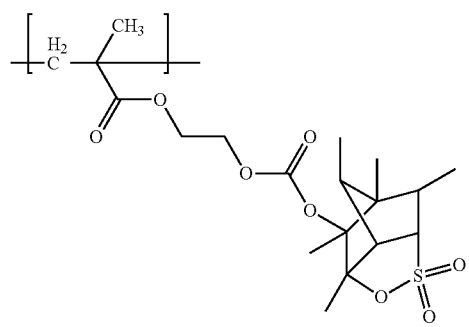

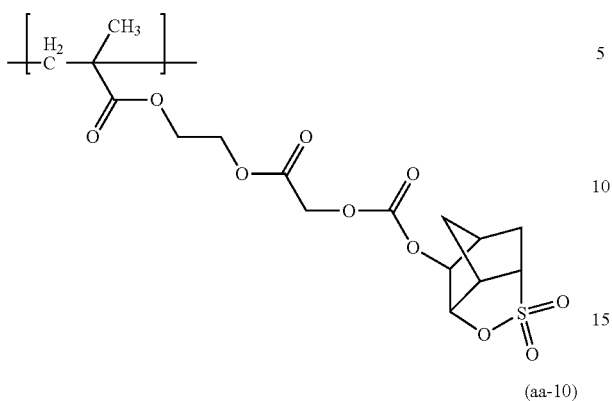
(aa-9)
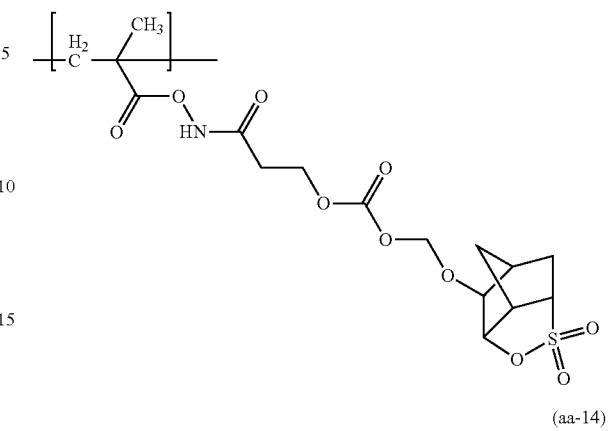
(aa-13)
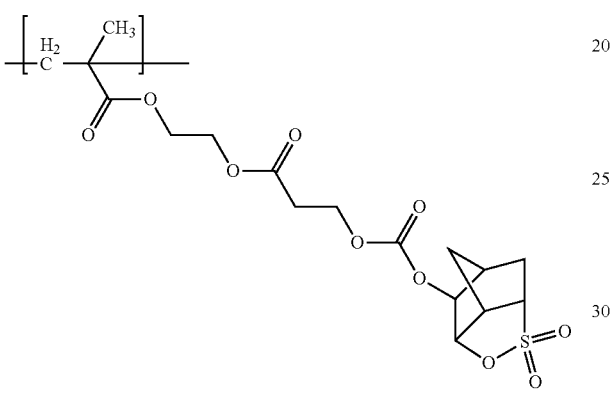
(aa-10)
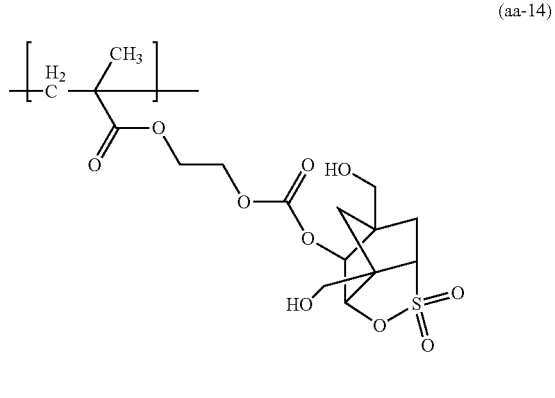
(aa-14)
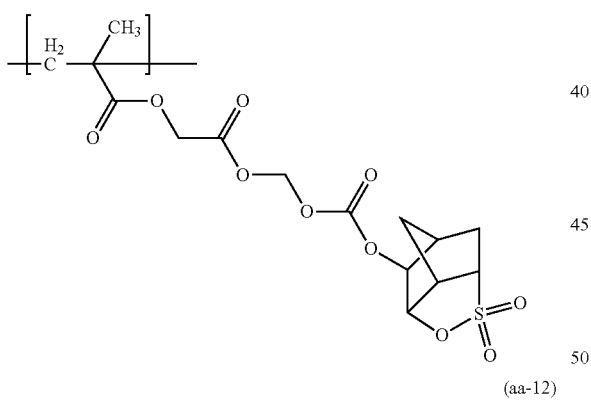
(aa-11)
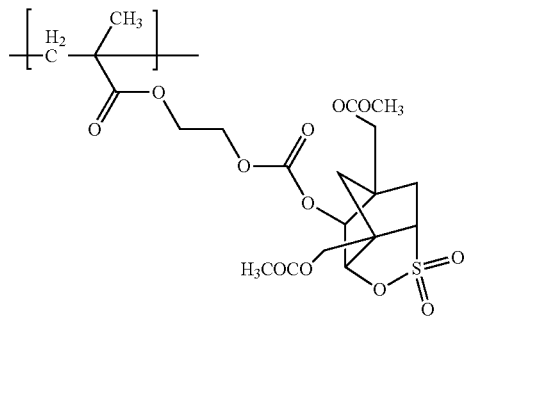
(aa-15)
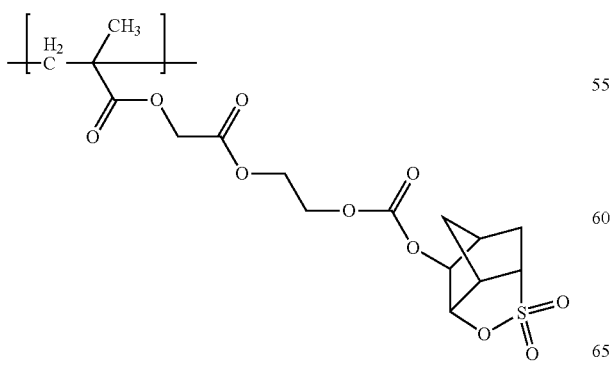
(aa-12)
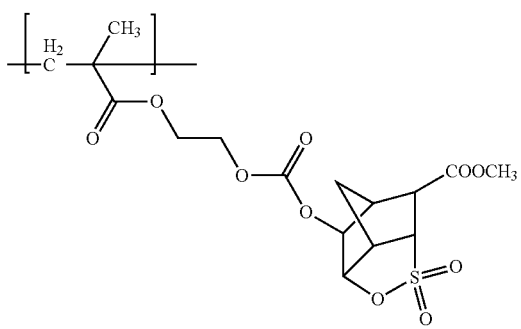
(aa-16)

(aa-17)
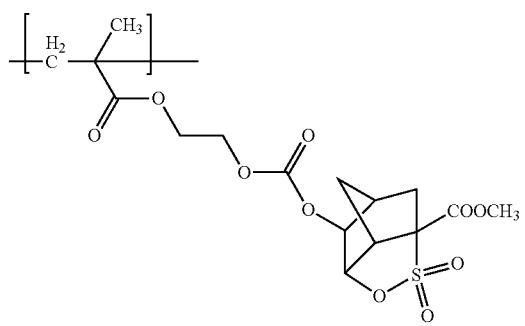

(aa-21)
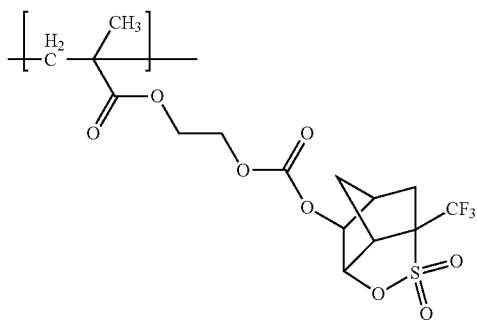

Examples of the structural unit represented by formula (aa) include the structural units represented by the formulae (aa-1) to (aa-21) wherein the partial structure M has been replaced by the partial structure A1, A2 or A3.

(aa-18)
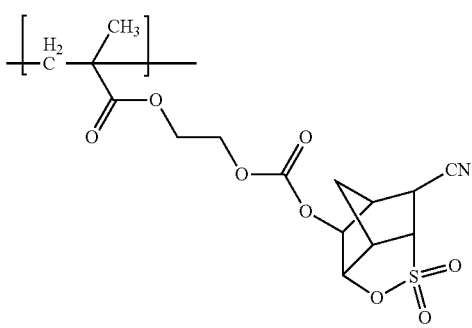

(partial structure M)

(partial structure A1)

(aa-19)
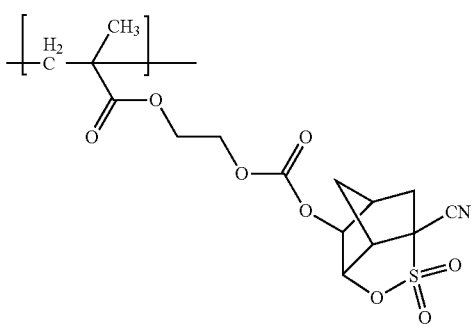

(partial structure A2)

(partial structure A3)

(aa-20)
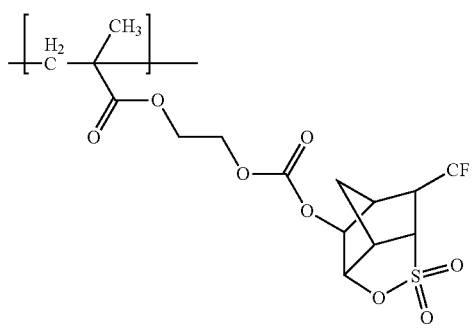

The structural unit represented by formula (aa) is derived from a compound represented by formula (aa'):

(aa')
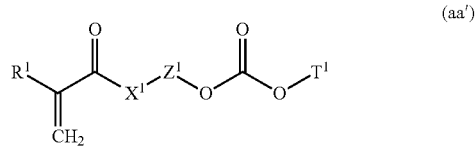

wherein $T^1$, $Z^1$, $X^1$ and $R^1$ are the same as defined above (hereinafter, simply referred to as compound (aa')).

The compound (aa') is one aspect of the present invention.

The compound (aa') can be produced by reacting a compound represented by the formula (aa1-a) with a compound represented by the formula (aa1-b) in a solvent such as acetonitrile.

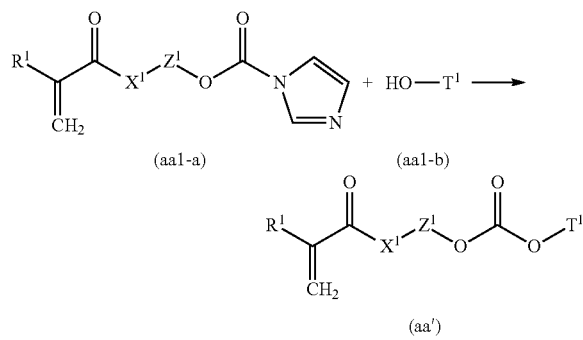

wherein $T^1$, $Z^1$, $X^1$ and $R^1$ are the same as defined above.

Examples of the compound represented by the formula (aa1-b) include compounds formed by bonding —OH to * of the groups represented by the formulae ($T^1$-1), ($T^1$-2), ($T^1$-3) and ($T^1$-4). Examples of the compound represented by the formula (aa1-b) include the following, and this compound is commercially available.

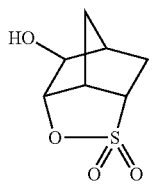

The compound represented by the formula (aa1-a) can be produced by reacting a compound represented by the formula (aa1-c) with 1,1'-carbonyldiimidazole in a solvent such as acetonitrile.

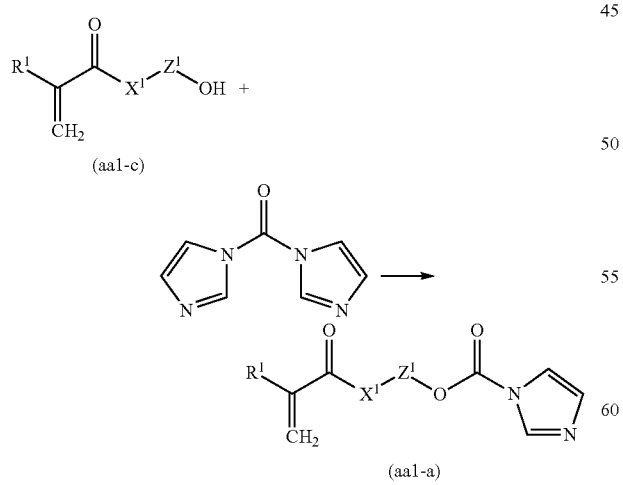

wherein $Z^1$, $X^1$ and $R^1$ are the same as defined above.
The compound represented by the formula (aa1-c) includes the following one, which is commercially available.

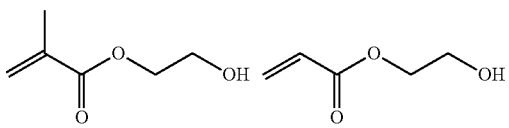

The content of the structural unit represented by formula (aa) in RESIN (A) is preferably 2 to 40% by mole, more preferably 3 to 35% by mole and especially preferably 5 to 30% by mole based on the total mole number of all the structural units of RESIN (A).

RESIN (A) may be a resin having an acid-labile group and being insoluble or poorly soluble in an aqueous alkali solution, but becoming soluble in an aqueous alkali solution by the action of an acid, or a resin not having an acid-labile group nor the above-mentioned properties as to solubility in an aqueous alkali solution.

RESIN (A) is preferably a resin being insoluble or poorly soluble in an aqueous alkali solution, but becoming soluble in an aqueous alkali solution by the action of an acid.

RESIN (A) preferably comprises the structural unit represented by formula (aa) and a structural unit derived from a compound having an acid-labile group.

When RESIN (A) is a resin becoming soluble in an aqueous alkali solution by the action of an acid, the resin can be produced by polymerizing the compound (aa') with a monomer having an acid-labile group. Two monomers having an acid-labile group can be used in combination. In this specification, "an acid-labile group" means a group capable of being eliminated by the action of an acid.

Examples of the acid-labile group include a group represented by the formula (1):

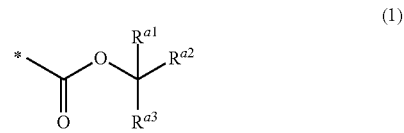

wherein $R^{a1}$, $R^{a2}$ and $R^{a3}$ independently each represent a C1-C8 alkyl group, a C3-C20 alicyclic hydrocarbon group or a combination of them, or $R^{a1}$ and $R^{a2}$ can be bonded each other to form a C2-C20 divalent aliphatic hydrocarbon group, and * represents a binding position.

Examples of the C1-C8 alkyl group include a methyl group, an ethyl group, a propyl group, a butyl group, a pentyl group, a hexyl group, a heptyl group, and an octyl group.

The alicyclic hydrocarbon group may be monocyclic or polycyclic, which includes a cycloalkyl group such as cyclopentyl group, cyclohexyl group, cycloheptyl group, and cyclooctyl group; polycyclic alicyclic hydrocarbon group such as decahydronaphtyl group, adamantyl group, norbornyl group and the groups represented as follow.

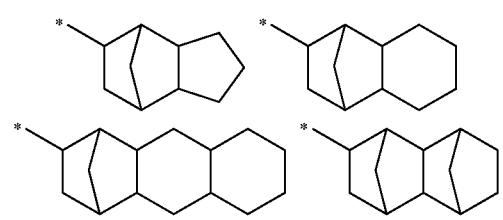

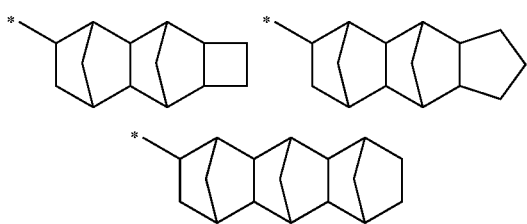

in which * represents a binding position.

The combination of alkyl group and alicyclic hydrocarbon group includes methylcyclohexyl group, dimethylcyclohexyl group, and methylnorbornyl group.

The divalent aliphatic hydrocarbon group formed by $R^{a1}$ and $R^{a2}$ which have bound each other has preferably C3-C12 carbon atoms.

When $R^{a1}$ and $R^{a2}$ are bonded each other to form a ring together with a carbon atom to which $R^{a1}$ and $R^{a2}$ are bonded, examples of the group represented by $-C(R^{a1})(R^{a2})(R^{a3})$ include the following groups.

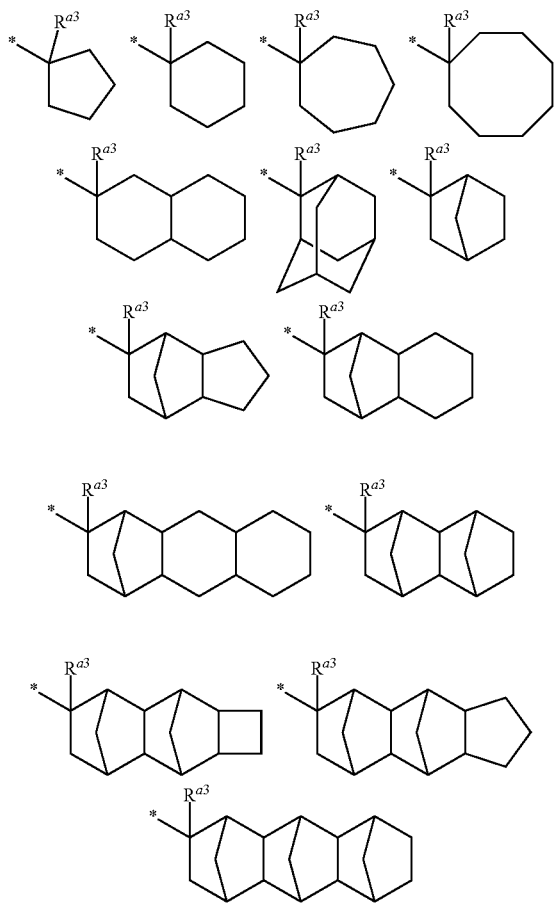

wherein $R^{a3}$ is the same as defined above, and * represents a binding position.

The group represented by the formula (1) includes a group represented by formula (1-1), formula (1-2), formula (1-3) or formula (1-4).

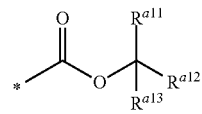

(1-1)

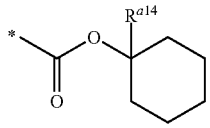

(1-2)

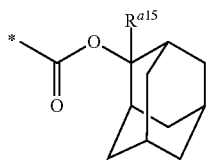

(1-3)

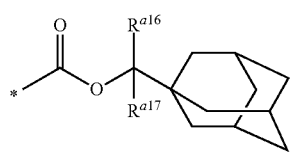

(1-4)

in which $R^{a11}$, $R^{a12}$, $R^{a13}$, $R^{a14}$, $R^{a15}$, $R^{a16}$ and $R^{a17}$ independently each represent a C1-C8 alkyl group.

The group represented by the formula (1) includes preferably tert-butoxycarbonyl group, 1-ethylcyclohexane-1-yloxycarbonyl group, 1-ethyladamantane-2-yloxycarbonyl group, and 2-isopropyladamantane-2-yloxycarbonyl group.

Among them, preferred are those represented by formula (1-2), formula (1-3) or formula (1-4) each of which has an alicyclic hydrocarbon group, and more preferred are those represented by formula (1-2) or formula (1-3) each of which has an alicyclic hydrocarbon group.

Examples of the acid-labile group include a group represented by the formula (2):

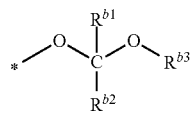

(2)

wherein $R^{b1}$ and $R^{b2}$ independently each represent a hydrogen atom or a C1-C12 monovalent hydrocarbon group, and $R^{b3}$ represents a C1-C20 monovalent hydrocarbon group, and $R^{b2}$ and $R^{b3}$ can be bonded each other to form a C2-C20 divalent hydrocarbon group, and a methylene group in the hydrocarbon group and the ring can be replaced by —O— or —S—, and * represents a binding position.

Examples of the hydrocarbon group include an alkyl group, an alicyclic hydrocarbon group and an aromatic hydrocarbon group.

Examples of the alkyl group for formula (2) include a methyl group, an ethyl group, a propyl group, a butyl group, a pentyl group, a hexyl group, a heptyl group, an octyl group, an decyl group, and a dodecyl group.

Examples of the alicyclic hydrocarbon group for formula (2) include those as mentioned above.

Examples of the aromatic hydrocarbon group include an aryl group such as a phenyl group, a naphthyl group, an anthryl group, a biphenyl group, a phenanthryl group and a fluorenyl group, which include those having a C1-C8 alkyl group.

It is preferred that at least one of $R^{b1}$ and $R^{b2}$ is a hydrogen atom.

Examples of the group represented by the formula (2) include the following;

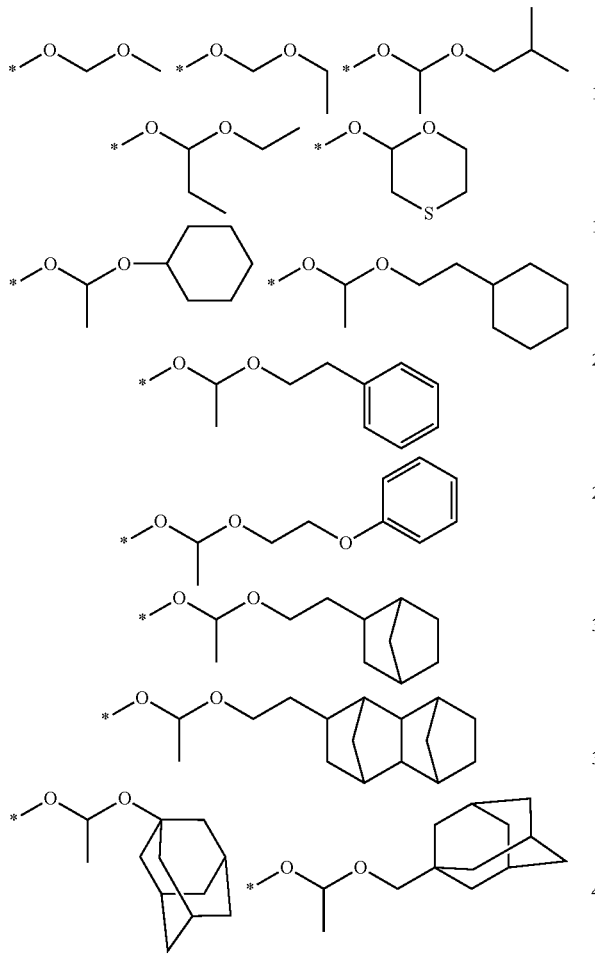

where * represents a binding position.

The monomer having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain. An acrylate monomer having the group represented by the formula (1) or (2) in its side chain or a methacryalte monomer having the group represented by the formula (1) or (2) in its side chain is especially preferable.

An acrylate monomer having the group represented by the formula (1) in its side chain or a methacryalte monomer having the group represented by the formula (1) in its side chain is preferable, and an acrylate monomer having the group represented by the formula (1) in which $R^{a1}$ and $R^{a2}$ are bonded each other to form a C5-C20 saturated alicycle together with the carbon atom to which they are bonded in its side chain or a methacryalte monomer having the group represented by the formula (1) in which $R^{a1}$ and $R^{a2}$ are bonded each other to form a C5-C20 saturated alicyclic hydrocarbon together with the carbon atom to which they are bonded in its side chain is more preferable. When the photoresist composition comprises a resin derived from a monomer having a bulky structure such as a saturated alicyclic hydrocarbon group, the photoresist composition having excellent resolution tends to be obtained.

Preferable examples of the monomer having an acid-labile group include the monomers represented by the formulae (a1-1) and (a1-2):

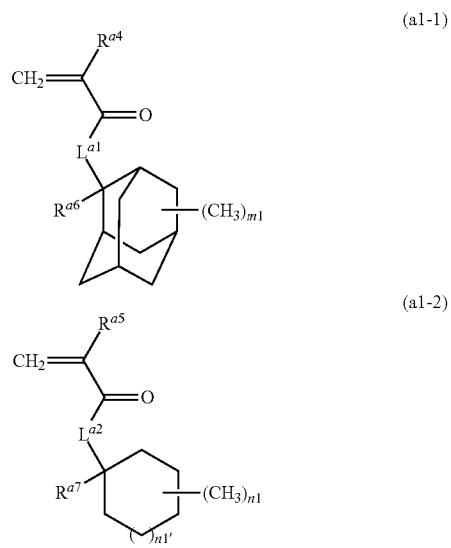

wherein $L^{a1}$ and $L^{a2}$ each independently represents *—O— or *—O—$(CH_2)_{k1}$—CO—O— in which * represents a binding position to —CO—, $R^{a4}$ and $R^{a5}$ each independently represents a hydrogen atom or a methyl group, and k1 represents an integer of 1 to 7, $R^{a6}$ and $R^{a7}$ each independently represents a C1-C8 alkyl group, a C3-C10 alicyclic hydrocarbon group or combination of them, and m1 represents an integer of 0 to 14, n1 represents an integer of 0 to 10 and n1' represents an integer of 0 to 3.

Each of $L^{a1}$ and $L^{a2}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

Each of $R^{a4}$ and $R^{a5}$ is a preferably methyl group.

Examples of the alkyl group represented by $R^{a6}$ and $R^{a7}$ include a methyl group, an ethyl group, a propyl group, a butyl group, a pentyl group, a hexyl group, a heptyl group, and an octyl group.

The alkyl group represented by $R^{a6}$ and $R^{a7}$ has preferably 1 to 6 carbon atoms.

The alicyclic hydrocarbon group represented by $R^{a6}$ and $R^{a7}$ may be monocyclic or polycyclic. Examples of the monocyclic alicyclic hydrocarbon group include cyclopentyl group, cyclohexyl group, cycloheptyl group and cyclooctyl group. Examples of the polycyclic alicyclic hydrocarbon group include decahydronaphtyl group, adamantyl group or norbornyl group, and the following groups.

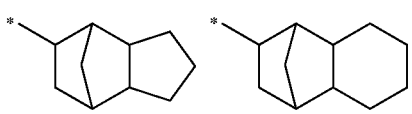

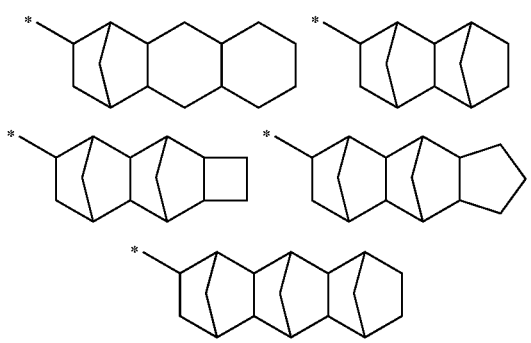

where * represents a binding position.

The alicyclic hydrocarbon group represented by $R^{a6}$ and $R^{a7}$ has preferably 8 or less, more preferably 6 or less carbon groups.

The combination of alkyl group and alicyclic hydrocarbon group includes cyclohexyl groups substituted with an alkyl group, such as methylcyclohexyl group, or dimethylcyclohexyl group, or norbornyl groups substituted with an alkyl group such as methylnorbornyl group.

In the formula (a1-1), m1 is preferably an integer of 0 to 3, and is more preferably 0 or 1.

In the formula (a1-2), n1 is preferably an integer of 0 to 3, and is more preferably 0 or 1, and n1' is preferably 0 or 1, and more preferably 1.

It is preferred that k1 is an integer of 1 to 4, and it is more preferred that k1 is 1.

Examples of the monomer represented by the formula (a1-1) include those described in JP2010-204646A1, preferably the monomers represented by the formulae (a1-1-1), (a1-1-2), (a1-1-3), (a1-1-4), (a1-1-5), (a1-1-6), (a1-1-7) and (a1-1-8), and more preferably monomers represented by the formulae (a1-1-1), (a1-1-2), (a1-1-3) and (a1-1-4).

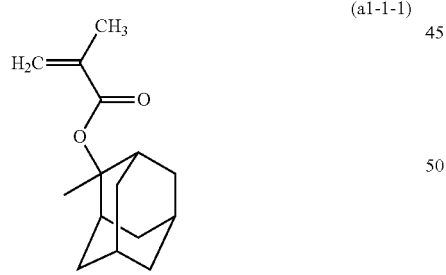
(a1-1-1)

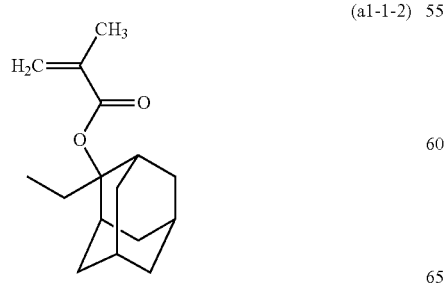
(a1-1-2)

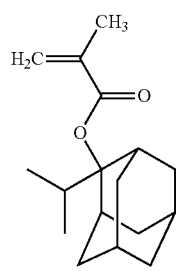
(a1-1-3)

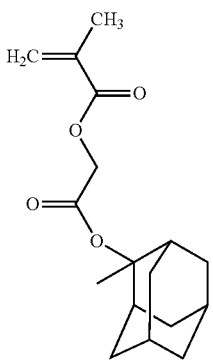
(a1-1-4)

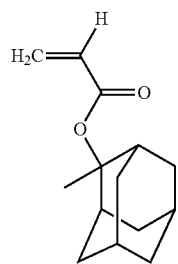
(a1-1-5)

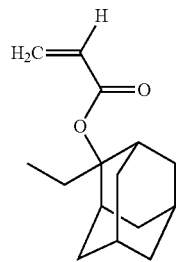
(a1-1-6)

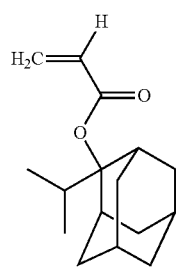
(a1-1-7)

(a1-1-8)

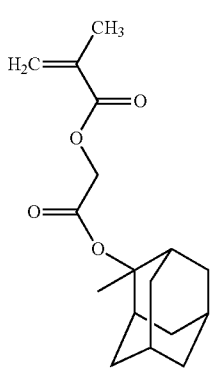

Examples of the monomers represented by the formula (a1-2) include 1-ethylcyclopentane-1-yl(meth)acrylate, 1-ethylcyclohexane-1-yl(meth)acrylate, 1-ethylcycloheptane-1-yl(meth)acrylate, 1-methylcyclopentane-1-yl(meth)acrylate, 1-methylcyclohexane-1-yl(meth)acrylate, and 1-isopropylcyclohexane-1-yl(meth)acrylate. Preferred are the monomers represented by formulae (a1-2-1) to (a1-2-12), more preferred are the monomers represented by formulae (a1-2-3), (a1-2-4), (a1-2-9) and (a1-2-10), and still more preferred are the monomers represented by formulae (a1-2-3) and (a1-2-9).

(a1-2-1)

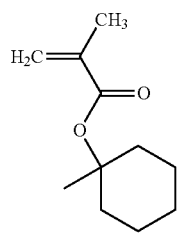

(a1-2-2)

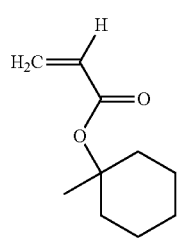

(a1-2-3)

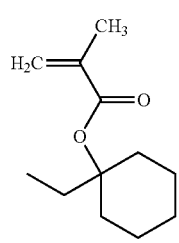

(a1-2-4)

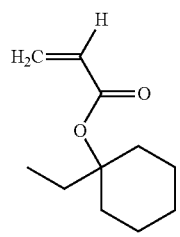

(a1-2-5)

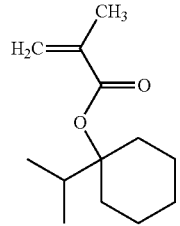

(a1-2-6)

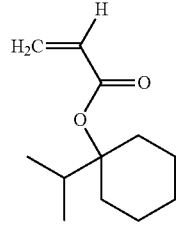

(a1-2-7)

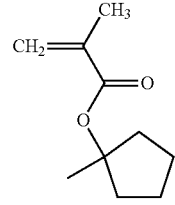

(a1-2-8)

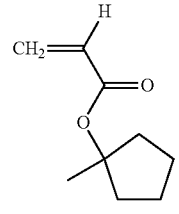

(a1-2-9)

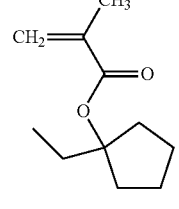

(a1-2-10)

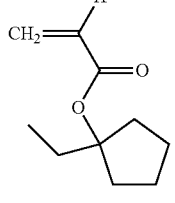

(a1-2-11)

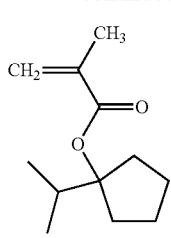

(a1-2-12)

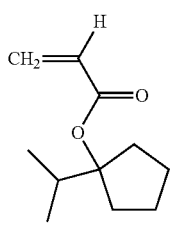

When RESIN (A) comprises the structural units derived from the monomer represented by the formula (a1-1) or (a1-2), the total content of the structural units derived from these monomers is usually 10 to 95% by mole, preferably 15 to 90% by mole and more preferably 20 to 85% by mole and especially preferably 30 to 60% by mole based on the total mole number of all the structural units of RESIN (A).

Among them, the structural unit derived from the monomer having an acid-labile group amounts preferably to 15 moles of the structural units derived from the monomer represented by the formula (a1). The more is the content of the monomers having an adamantyl group, the more improved is the resistance to dry-etching.

Other examples of the monomer having an acid-labile group include a monomer represented by the formula (a1-5):

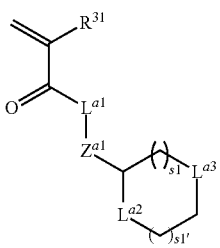

(a1-5)

wherein $R^{31}$ represents a hydrogen atom, a halogen atom, a C1-C4 alkyl group which may be substituted with a halogen atom, $Z^{a1}$ represents a single bond or *—O—$(CH_2)_{k1}$—CO-$L^{a4}$-, k1 represents an integer of 1 to 4, * represents a binding position to $L^{a1}$, $L^1$, $L^2$, $L^3$ and $L^4$ independently each represent —O— or —S—, s1 represents an integer of 1 to 3, and s1' represents an integer of 0 to 3.

$R^{31}$ is preferably a hydrogen atom, a methyl group, or a trifluoromethyl group.

One of $L^{a2}$ and $L^{a3}$ is preferably —O—, while the other of them is preferably —S—.

In the formula (a1-5), s1 is preferably 1 and s1' is preferably 0, 1 or 2.

$Z^{a1}$ is preferably a single bond or —$CH_2$—CO—O—.

Examples of the monomer represented by the formula (a1-5) include the following.

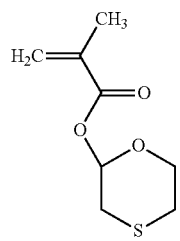

(a1-5-1)

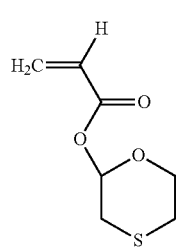

(a1-5-2)

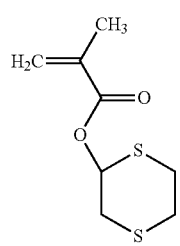

(a1-5-3)

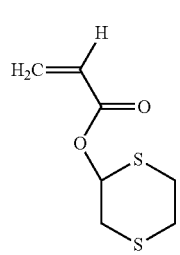

(a1-5-4)

When RESIN (A) comprises the structural unit derived form the monomer represented by the formula (a1-5), the content of the structural unit derived from this monomer is usually 1 to 95% by mole, preferably 3 to 90% by mole, and more preferably 5 to 85% by mole based on total mole number of all the structural units of RESIN (A).

RESIN (A) preferably further comprises a structural unit derived from a monomer having no acid-labile group, other than the structural unit of formula (aa) (hereinafter, such structural unit is briefly referred to as "structural unit derived from a monomer having no acid-labile group"). RESIN (A) can have two or more kinds of structural units derived from the monomers having no acid-labile group.

The monomer having no acid-labile group preferably has a hydroxyl groups or a lactone ring. When the resin comprises a structural unit derived from the monomer having no acid-labile group and having a hydroxyl groups or a lactone ring, a photoresist composition having good resolution and adhesiveness of photoresist to a substrate tends to be obtained.

When KrF excimer laser (wavelength: 248 nm) lithography system, or a high energy laser such as electron beam and extreme ultraviolet is employed as an exposure system, RESIN (A) preferably comprises a structural unit derived from a monomer having a phenolic-hydroxy group as the monomer having no acid-labile group. When ArF excimer laser (wavelength: 193 nm) is employed as an exposure system, RESIN (A) preferably comprises a structural unit derived from a monomer having an alcoholic-hydroxy group as the monomer having no acid-labile group.

Examples of the monomer having no acid-labile group and having a phenolic-hydroxyl group include those represented by the formula (a2-0):

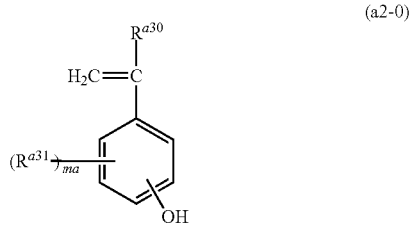

wherein $R^{a30}$ represents a hydrogen atom, a halogen atom, a C1-C6 alkyl group optionally having a halogen atom,
$R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

RESIN (A) which comprises the structural unit derived from the monomer having no acid-labile group and having a phenolic-hydroxyl group can be produced, for example, by polymerizing a monomer in which a phenolic-hydroxy group has been protected with a protecting group such as an acetyl group, for example in a manner of radical polymerization, followed by conducting deprotection of the obtained polymer with an acid or a base. Considering that RESIN (A) generally comprises a structural unit derived from a monomer having an acid-labile group, the deprotection of protected phenolic-hydroxy groups is preferably carried out by contacting the group with a base such as 4-dimethylaminopyridine or triethylamine so that the deprotection does not significantly detract the acid-labile group.

The monomers having no acid-labile group and having a phenolic-hydroxyl group include those described in JP2010-204634A1, which are preferably those represented by formula (a2-0-1) or formula (a2-0-2).

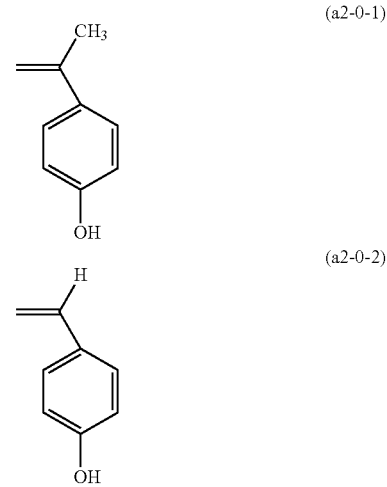

When RESIN (A) comprises a structural unit derived from the monomer of formula (a2-0), the content of the structural unit is usually 5 to 90% by moles, preferably 10 to 85% by moles, and more preferably 15 to 80% by moles, based on total mole number of all the structural units of RESIN (A).

The monomers having no acid-labile group and having an alcoholic-hydroxyl group include those represented by formula (a2-1);

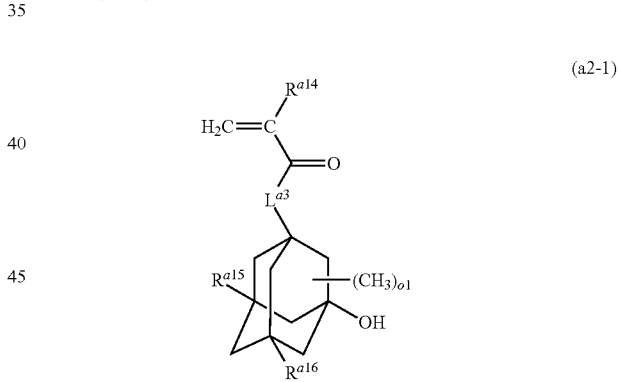

wherein $L^{a3}$ represents —O— or —O—$(CH_2)_{k2}$—CO—O—, where k2 represents an integer of 1 to 7 and * is a binding position to —CO—,
$R^{a14}$ represents a hydrogen atom or a methyl group,
$R^{a15}$ and $R^{a16}$ each independently represent a hydrogen atom, a methyl group, or a hydroxy group, and
O1 represents an integer of 0 to 10.

In formula (a2-1), $L^{a3}$ is preferably —O— or —O—$(CH_2)_{f1}$—CO—O—, where f1 represents an integer of 1 to 4 and * is a binding position to —CO—, and more preferably —O—.
$R^{a14}$ is preferably a methyl group.
$R^{a15}$ is preferably a hydrogen atom.
$R^{a16}$ is preferably a hydrogen atom or a hydroxy group.
O1 is preferably an integer of 0 to 3, and more preferably 0 or 1.

The monomers having no acid-labile group and having a alcoholic-hydroxyl group include those described in JP2010-

204646A1, which are preferably those represented by formulae (a2-1-1), (a2-1-2), (a2-1-3), (a2-1-4), (a2-1-5) and (a2-1-6), more preferably those represented by any one of formulae (a2-1-1), (a2-1-2), (a2-1-3) and (a2-1-4), and still more preferably those represented by any formulae (a2-1-1) and (a2-1-3).

(a2-1-1)
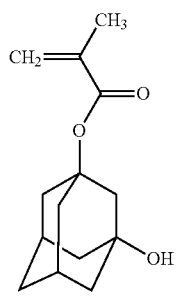

(a2-1-2)
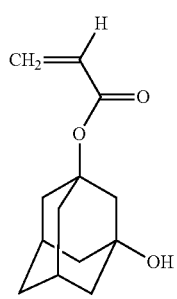

(a2-1-3)
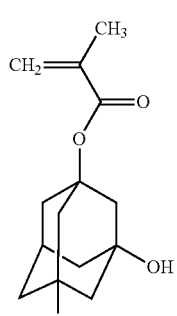

(a2-1-4)
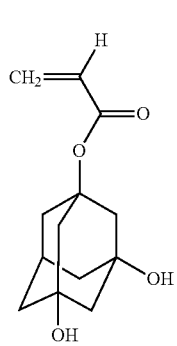

(a2-1-5)
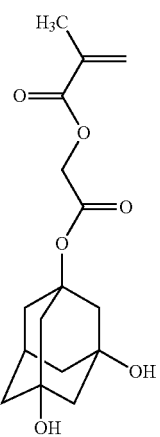

(a2-1-6)
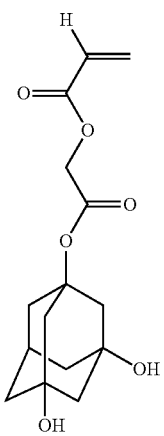

When RESIN (A) comprises a structural unit derived from the monomer of formula (a2-1), the content of the structural unit is usually 3 to 45% by moles, preferably 5 to 40% by moles, more preferably 5 to 35% by moles, and still more preferably 5 to 15% by moles, based on total mole number of all the structural units of RESIN (A).

Examples of the lactone ring of the monomer having no acid-labile group and a lactone ring include a monocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

(a3-1)
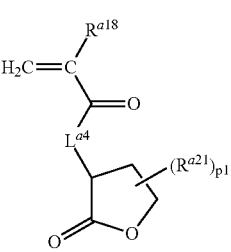

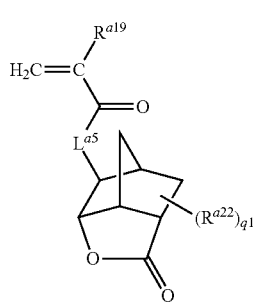
(a3-2)

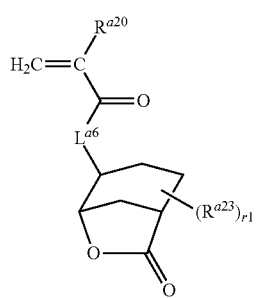
(a3-3)

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 alkyl group, $R^{a22}$ and $R^{a23}$ are independently in each occurrence a carboxyl group, a cyano group or a C1-C4 alkyl group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— or *—O—$CH_2$—CO—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer having no acid-labile group and a lactone ring include those described in JP2010-204646. Preferred are the monomers represented by the formulae (a3-1-1), (a3-1-2), (a3-1-3), (a3-1-4), (a3-2-1), (a3-2-2), (a3-2-3), (a3-2-4), (a3-3-1), (a3-3-2), (a3-3-3) and (a3-3-4), more preferred are the monomers represented by the formulae (a3-1-1), (a3-1-2), (a3-2-3), and (a3-2-4), and still more preferred are the monomers represented by the formulae (a3-1-1) and (a3-2-3).

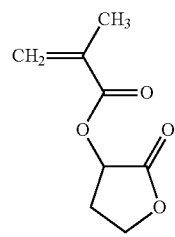
(a3-1-1)

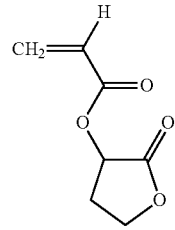
(a3-1-2)

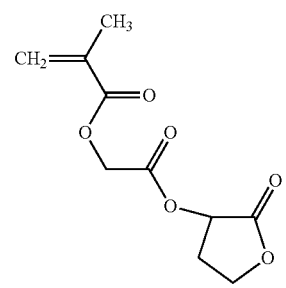
(a3-1-3)

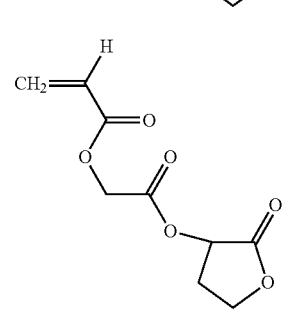
(a3-1-4)

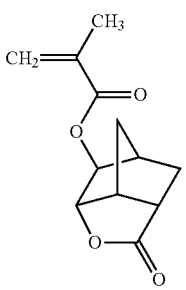
(a3-2-1)

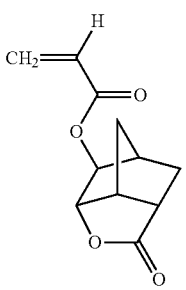
(a3-2-2)

(a3-2-3)

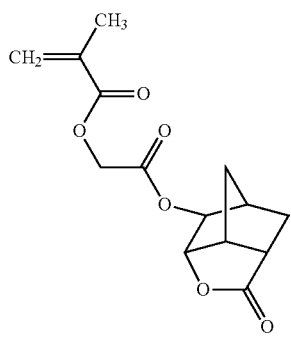

(a3-2-4)

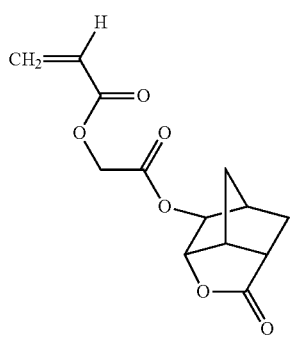

(a3-3-1)

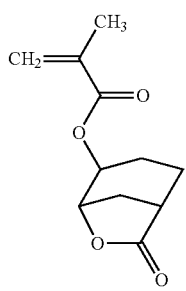

(a3-3-2)

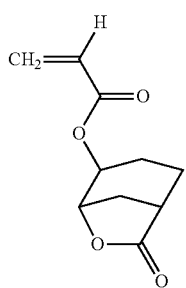

(a3-3-3)

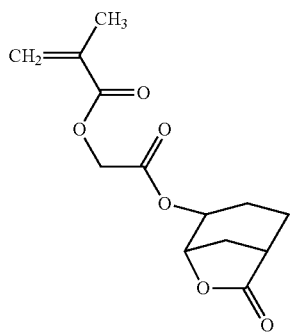

(a3-3-4)

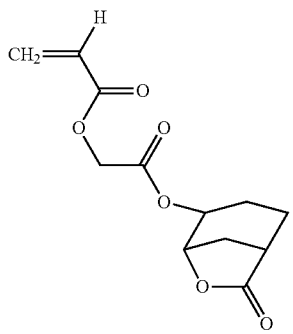

Among them, preferred are the structural units derived from α-acryloyloxy-γ-butyrolactone, α-methacryloyloxy-γ-butyrolactone, β-acryloyloxy-γ-butyrolactone, β-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-α-methyl-γ-butyrolactone, β-methacryloyloxy-α-methyl-γ-butyrolactone, 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate.

When RESIN (A) comprises the structural unit derived from the monomer having no acid-labile group and having a lactone ring, the content thereof is usually 5 to 70% by mole, preferably 10 to 65% by mole and more preferably 10 to 60% by mole, based on total mole number of all the structural units of RESIN (A).

When RESIN (A) comprises the structural unit represented by the formula (a3-1), (a3-2) or (a3-3), each content thereof is preferably 5 to 60% by mole, more preferably 5 to 50% by mole, and still more preferably 10 to 50% by mole, based on total mole number of all the structural units of RESIN (A).

RESIN (A) may comprise structural units derived from a compound other than the monomers as mentioned above (Hereinafter, such compound is briefly referred to as "another monomer").

Examples of another monomer include one represented by formula (a4-1);

(a4-1)

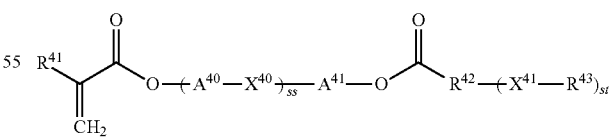

wherein
$R^{41}$ represents a hydrogen atom or a methyl group,
$A^{40}$ and $A^{41}$ each independently represent a C1-C6 divalent aliphatic hydrocarbon group,
$X^{40}$ represents —O—, —CO— or —CO—O—,
$R^{42}$ represents a C1-C18 aliphatic hydrocarbon group which may be substituted with a fluorine atom and $R^{43}$ represents a C1-C17 monovalent aliphatic hydrocarbon group which may be substituted with a fluorine atom, provided that one or both aliphatic hydrocarbon groups of $R^{42}$ and $R^{43}$ have a fluorine atom, $X^{41}$ represents —CO—O—,
ss represents an integer of 0 to 2, and
st represents an integer of 0 to 3.

$A^{41}$ is preferably a C1-C6 alkanediyl group, more preferably a C1-C4 alkanediyl group, and still preferably an ethylene group.

The partial structure represented by -$(A^{40}$-$X^{40})_{ss}$-$A^{41}$- specifically includes the following structures.

In the following formulae, * represents a binding position, and one positioned at the left side is a binding position to —O—CO—C(=CH$_2$)—$R^{41}$.

The partial structure represented by -$(A^{40}$-$X^{40})_{ss}$-$A^{41}$- where $X^{40}$ represents —O— includes the following ones.

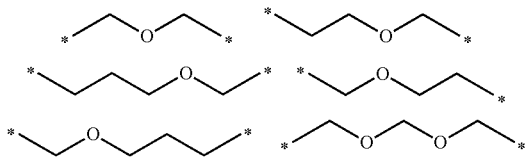

The partial structure represented by -$(A^{40}$-$X^{40})_{ss}$-$A^{41}$- where $X^{40}$ represents —CO— includes the following ones.

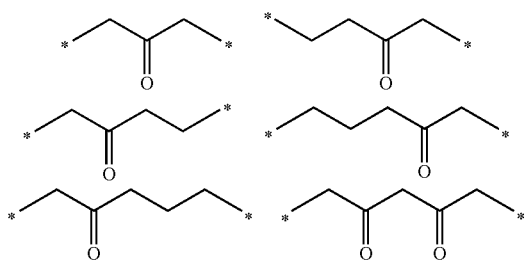

The partial structure represented by -$(A^{40}$-$X^{40})_{ss}$-$A^{41}$- where $X^{40}$ represents —CO—O— includes the following ones.

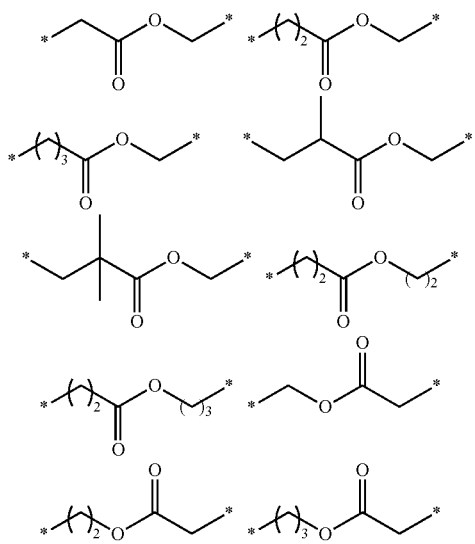

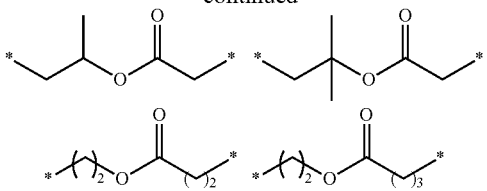

The aliphatic hydrocarbon group represented by $R^{42}$ or $R^{43}$ may have a carbon-carbon double bond, which is preferably a saturated aliphatic hydrocarbon group.

The aliphatic hydrocarbon group includes an alkyl group, an alicyclic hydrocarbon group, and a combination of alkyl group and alicyclic hydrocarbon group.

Examples of the alkyl group include a methyl group, an ethyl group, a propyl group, an isopropyl group, a butyl group, a butyl group, a pentyl group, a hexyl group, a heptyl group and an octyl group.

The alicyclic hydrocarbon group may be monocyclic or polycyclic, which includes a cycloalkyl group such as cyclopentyl group, cyclohexyl group, cycloheptyl group, and cyclooctyl group; polycyclic alicyclic hydrocarbon group such as decahydronaphtyl group, adamantyl group, norbornyl group and the compounds represented as follow.

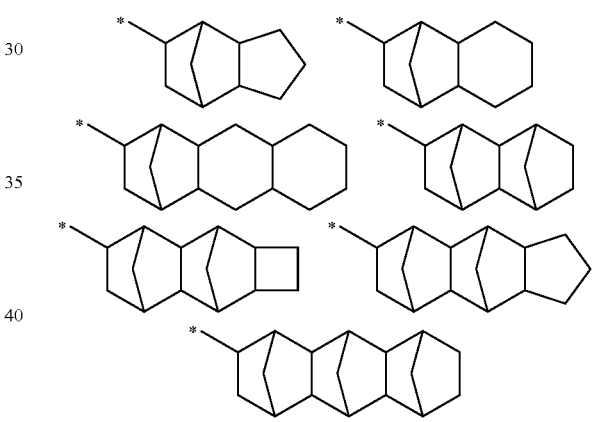

The combination of alkyl group and alicyclic hydrocarbon group includes methylcyclohexyl group, dimethylcyclohexyl group, and methylnorbornyl group.

In formula (a4-1), any one of the aliphatic hydrocarbon groups represented by $R^{42}$ and $R^{43}$ preferably has a fluorine atom, although both of the aliphatic hydrocarbon groups represented by $R^{42}$ and $R^{43}$ may have a fluorine atom. When st represents 0, the aliphatic hydrocarbon group represented by $R^{42}$ preferably has a fluorine atom. The aliphatic hydrocarbon groups having a fluorine atom, which is represented by $R^{42}$ and $R^{43}$, include an alkyl group having a fluorine atom or an alicyclic hydrocarbon group having a fluorine atom, preferably a cycloalkyl group having an fluorine atom. The alkyl group having a fluorine atom is one in which a hydrogen atom has been replaced by a fluorine atom. The cycloalkyl group having an fluorine atom is one in which a hydrogen atom has been replaced by a fluorine atom.

When one or both of $R^{42}$ and $R^{43}$ represent an aliphatic hydrocarbon group having a fluorine atom, such group is preferably that in which all of hydrogen atoms have been replaced by fluorine atoms. The aliphatic hydrocarbon group represented by $R^{42}$ and $R^{43}$ is preferably a C1-C6 perfluoroalkyl group or a C3-C6 cycloalkyl group, more preferably a C1-C6 perfluoroalkyl group, and still more preferably a C1-C3 perfluoroalkyl group.

The perfluoroalkyl group includes perfluoromethyl group, perfluoroethyl group, perfluoropropyl group, a perfluorobutyl group, perfluoropentyl group, and perfluorohexyl group.

The perfluorocycloalkyl group includes a perfluorocyclohexyl group.

The ss represents preferably 0.
The st represents preferably 0 or 1.
The monomer represented by formula (a4-1) is preferably represented by formula (a4-1').

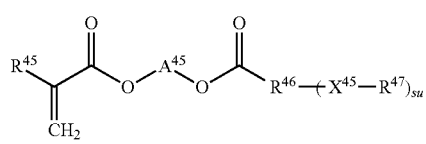
(A4-1')

wherein
$R^{45}$ represents a hydrogen atom or a methyl group,
$A^{45}$ represents a C1-C6 divalent aliphatic hydrocarbon group,
$R^{46}$ represents a C1-C18 aliphatic hydrocarbon group which may be substituted with a fluorine atom and $R^{47}$ represents a C1-C17 aliphatic hydrocarbon group which may be substituted with a fluorine atom, provided that one or both aliphatic hydrocarbon groups of $R^{46}$ and $R^{47}$ have a fluorine atom,
$X^{45}$ represents —CO—O—, and
su represents an integer of 0 to 1.

Both of $R^{46}$ and $R^{47}$ may represent an aliphatic hydrocarbon group having a fluorine atom, however any one of $R^{46}$ and $R^{47}$ preferably represents an aliphatic hydrocarbon group having a fluorine atom. When su is 1, it is preferred that $R^{46}$ represents an aliphatic hydrocarbon group having a fluorine atom and $R^{47}$ represents an aliphatic hydrocarbon group having no fluorine atom. In this case, $R^{46}$ preferably represents a perfluoroalkanediyl group.

The total number of the carbon atoms in $R^{46}$ and $R^{47}$ is 2 to 17. The number of the carbon atoms in $R^{46}$ is preferably 1 to 6, more preferably 1 to 3.

$R^{47}$ preferably represents preferably a C4-C15 aliphatic hydrocarbon group, more preferably a C5-C12 aliphatic hydrocarbon group, and still more preferably a cyclohexyl group and an adamantyl group. It is particularly preferred that $R^{46}$ represents C1-C6 aliphatic hydrocarbon group having a fluorine atom and $R^{47}$ represents a methyl group, an ethyl group, isopropyl group, a cyclohexyl group and an adamantyl group.

$A^{45}$ preferably represents an ethyl group.
The structure *—$R^{46}$—$X^{45}$—$R^{47}$ where * represents a binding position to a carbonyl group, preferably includes those as follow.

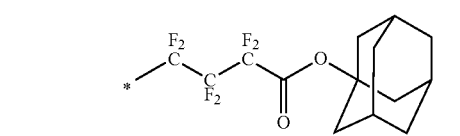
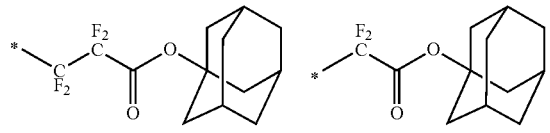

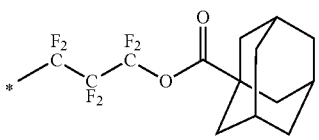
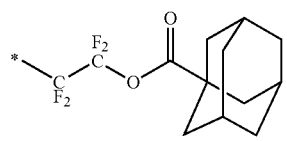 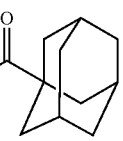

The monomer represented by formula (a4-1) where st is 0 includes those represented by formulae (a4-1-1), (a4-1-2), (a4-1-3), (a4-1-4), (a4-1-5), (a4-1-6), (a4-1-7), (a4-1-8), (a4-1-9), (a4-1-10), (a4-1-11), (a4-1-12), (a4-1-13), (a4-1-14), (a4-1-15), (a4-1-16), (a4-1-17), (a4-1-18), (a4-1-19), (a4-1-20), (a4-1-21) and (a4-1-22).

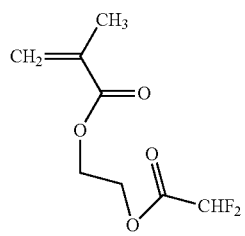
(a4-1-1)

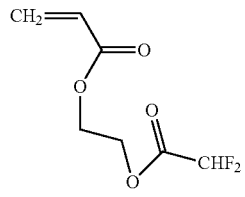
(a4-1-2)

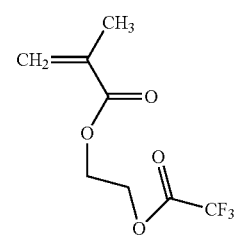
(a4-1-3)

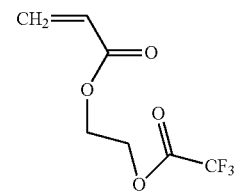
(a4-1-4)

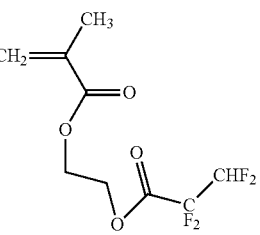
(a4-1-5)

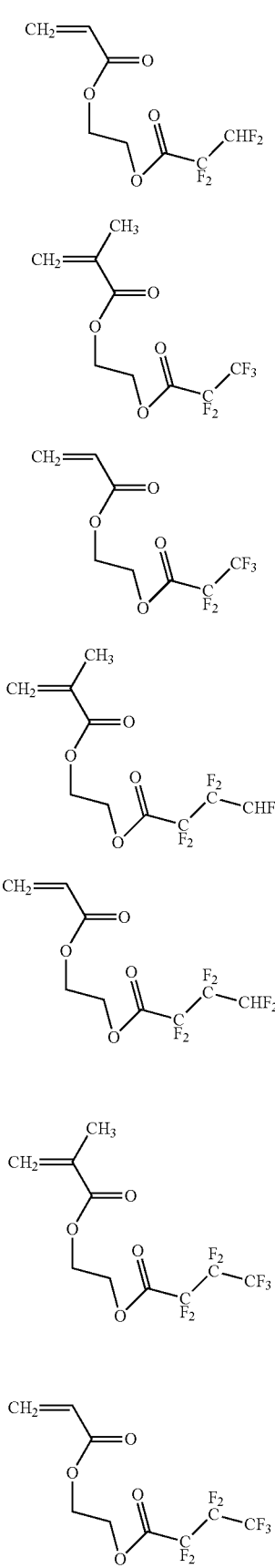
(a4-1-6)
(a4-1-7)
(a4-1-8)
(a4-1-9)
(a4-1-10)
(a4-1-11)
(a4-1-12)
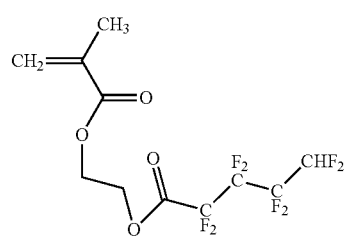
(a4-1-13)
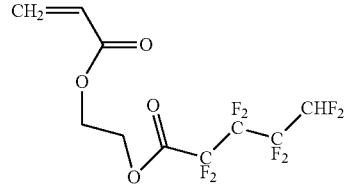
(a4-1-14)
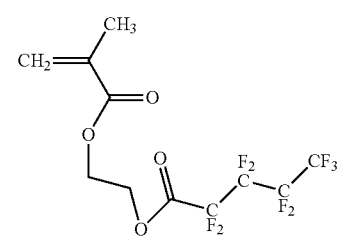
(a4-1-15)
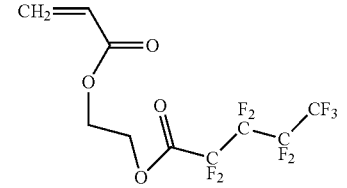
(a4-1-16)
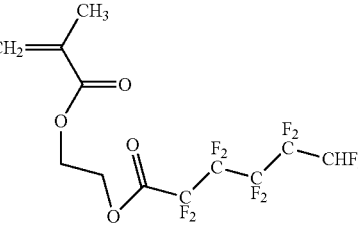
(a4-1-17)
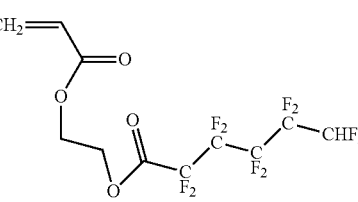
(a4-1-18)
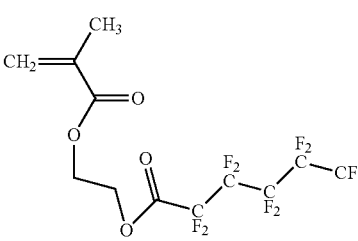
(a4-1-19)

(a4-1-20)
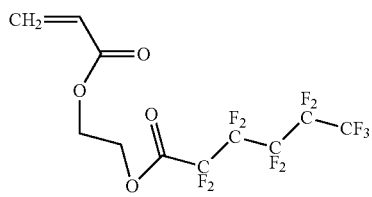
(a4-1-21)
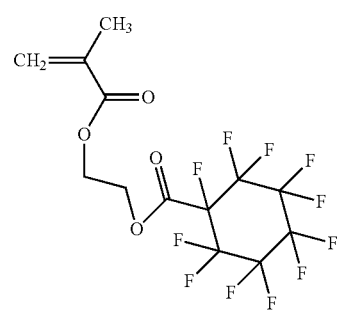
(a4-1-22)
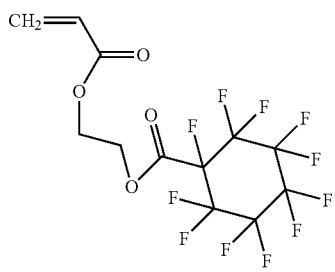
Among them, preferred are the monomers represented by formulae (a4-1-3), (a4-1-4), (a4-1-7), (a4-1-8), (a4-1-11), (a4-1-12), (a4-1-15), (a4-1-16), (a4-1-19), (a4-1-20), (a4-1-21) and (a4-1-22).
The monomer represented by formula (a4-1) where st is 1 includes those represented by formulae (a4-1'-1), (a4-1'-2), (a4-1'-3), (a4-1'-4), (a4-1'-5), (a4-1'-6), (a4-1'-7), (a4-1'-8), (a4-1'-9), (a4-1'-10), (a4-1'-11), (a4-1'-12), (a4-1'-13), (a4-1'-14), (a4-1'-15), (a4-1'-16), (a4-1'-17), (a4-1'-18), (a4-1'-19), (a4-1'-20), (a4-1'-21) and (a4-1'-22), preferably those represented by formulae (a4-1'-9), (a4-1'-10), (a4-1'-11), (a4-1'-12), (a4-1'-13), (a4-1'-14), (a4-1'-15), (a4-1'-16), (a4-1'-17), (a4-1'-18), (a4-1'-19), (a4-1'-20), (a4-1'-21) and (a4-1'-22).
(a4-1'-1)
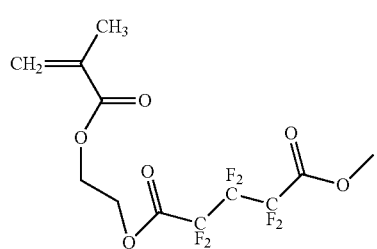
(a4-1'-2)
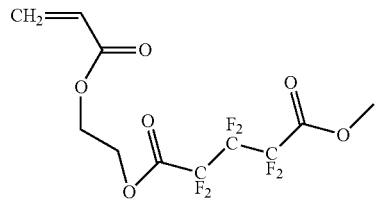
(a4-1'-3)
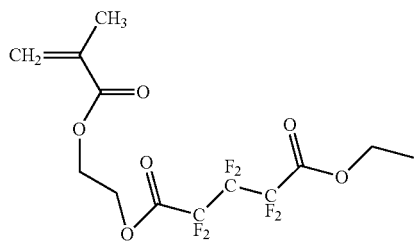
(a4-1'-4)
(a4-1'-5)
(a4-1'-6)
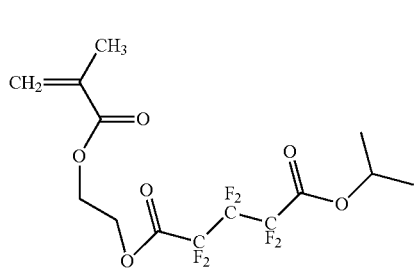
(a4-1'-7)
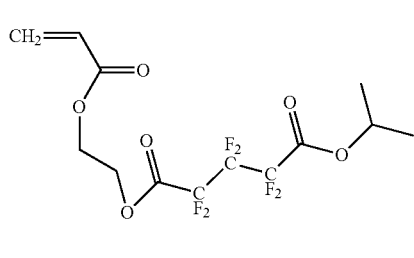
(a4-1'-8)
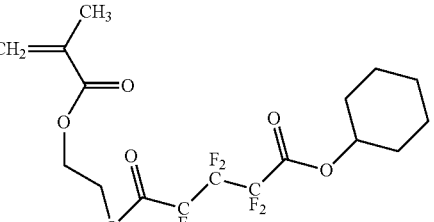
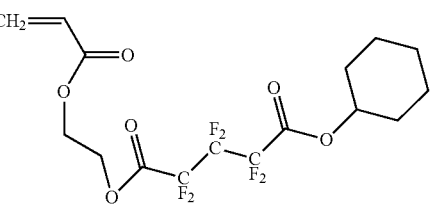

(a4-1'-9)
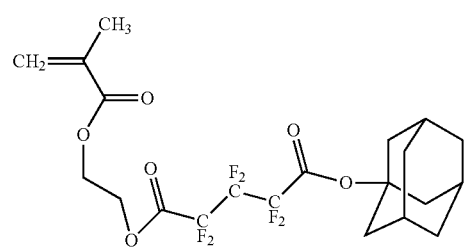
(a4-1'-10)
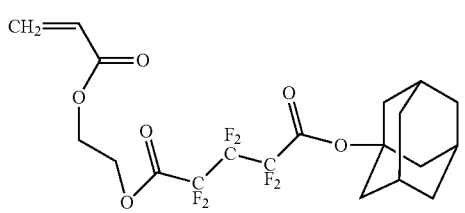
(a4-1'-11)
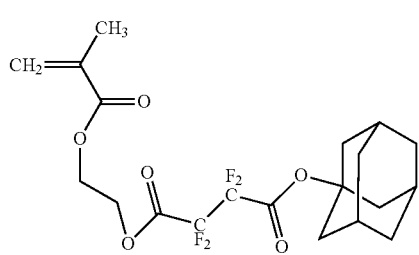
(a4-1'-12)
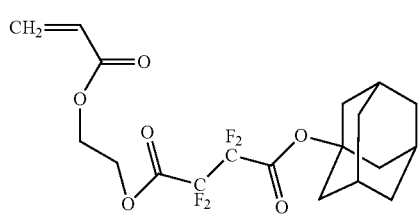
(a4-1'-13)
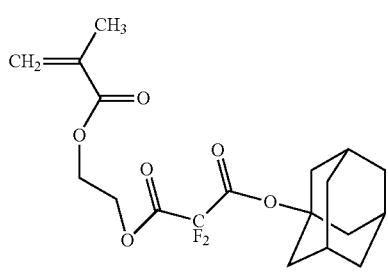
(a4-1'-14)
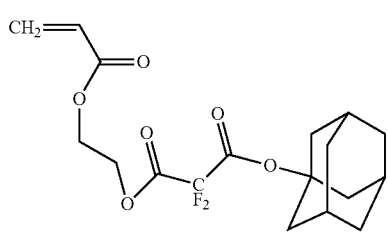
(a4-1'-15)
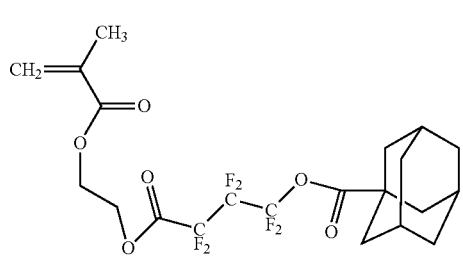
(a4-1'-16)
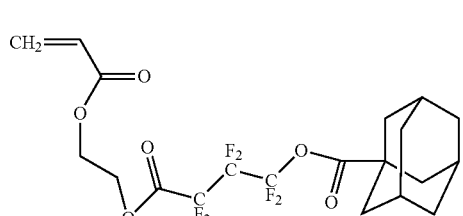
(a4-1'-17)
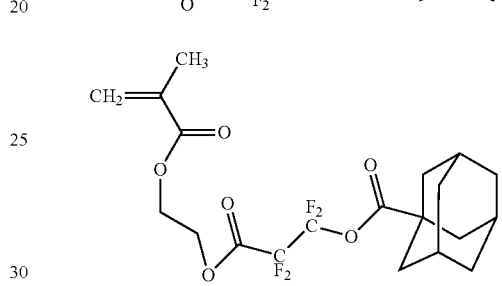
(a4-1'-18)
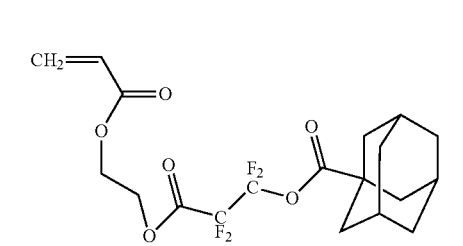
(a4-1'-19)
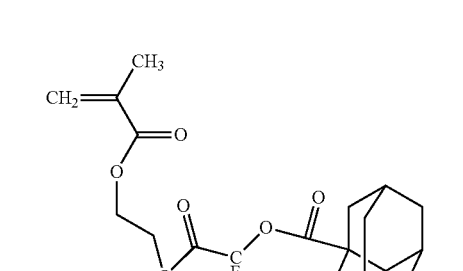
(a4-1'-20)
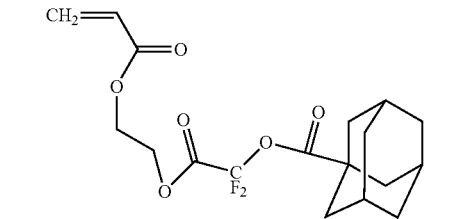

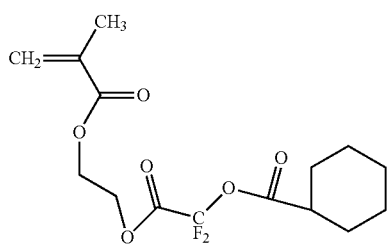

(a4-1'-21)

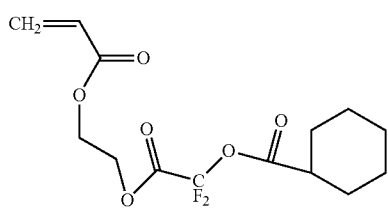

(a4-1'-22)

When RESIN (A) comprises the structural unit derived from the monomer represented by formula (a4-1), the content of the structural unit is usually 1 to 20% by mole, preferably 2 to 15% by mole and more preferably 3 to 10% by mole, based on total mole number of all the structural units of RESIN (A).

RESIN (A) comprises preferably the structural unit represented by formula (aa), the structural unit derived from a monomer having an acid-labile group and the structural unit derived from a monomer having no acid-labile group, more preferably the structural unit represented by formula (aa), the structural unit derived from a monomer having an acid-labile group and the structural unit derived from a monomer having no acid-labile group and having a hydroxyl group and/or a lactone ring.

For RESIN (A), the monomer having an acid-labile group is preferably those having an adamantyl group or a cyclohexyl group, specifically those represented by formula (a1-1) or (a1-2), and more preferably those having an adamantyl group, specifically those represented by formula (a1-1).

For RESIN (A), the monomer having no acid-labile group but having a hydroxyl group is preferably those having no acid-labile group but having a hydroxyadamantyl group, specifically those represented by formula (a2-1). The monomer having no acid-labile group but having a lactone ring is preferably those having no acid-labile group but having a γ-butyrolactone ring, specifically those represented by formula (a3-1) and formula (a3-2)

RESIN (A) can be produced by a known polymerization method such as radical polymerizaition.

When RESIN (A) is a polymer which comprises a structural unit represented by formula (aa) and a structural unit derived from a monomer having an acid-labile group, the molar ratio of these units, i.e., [structural unit represented by formula (aa)]/[structural unit derived from a monomer having an acid-labile group], is preferably 5/95 to 40/60, and more preferably 5/95 to 30/70.

When RESIN (A) is a polymer which comprises a structural unit represented by formula (aa), a structural unit derived from a monomer having an acid-labile group, and a structural unit derived from a monomer having no acid-labile group, the contents of them are preferably Structural unit represented by formula (aa): 2 to 40% by mole Structural unit derived from a monomer having an acid-labile group: 25 to 70% by mole, Structural unit derived from a monomer having no acid-labile group: 35 to 80% by mole, more preferably Structural unit represented by formula (aa): 3 to 35% by mole Structural unit derived from a monomer having an acid-labile group: 25 to 65% by mole, Structural unit derived from a monomer having no acid-labile group: 40 to 75% by mole, still more preferably Structural unit represented by formula (aa): 5 to 30% by mole Structural unit derived from a monomer having an acid-labile group: 30 to 60% by mole, Structural unit derived from a monomer having no acid-labile group: 40 to 70% by mole, based on the total mole number of all the structural units of RESIN (A).

RESIN (A) is preferably a copolymer which comprises a structural unit represented by formula (aa), a structural unit derived from a monomer having an acid-labile group, a structural unit derived from a monomer having no acid-labile group but having a hydroxyl group, and a structural unit derived from a monomer having no acid-labile group but having a lactone ring. The contents of these structural units in the copolymer are preferably Structural unit represented by formula (aa): 2 to 40% by mole Structural unit derived from a monomer having an acid-labile group: 25 to 70% by mole Structural unit derived from a monomer having no acid-labile group but having a hydroxyl group: 3 to 35% by mole, Structural unit derived from a monomer having no acid-labile group but having a lactone ring: 32 to 65% by mole, more preferably Structural unit represented by formula (aa): 3 to 35% by mole Structural unit derived from a monomer having an acid-labile group: 25 to 65% by mole Structural unit derived from a monomer having no acid-labile group but having a hydroxyl group: 4 to 30% by mole, Structural unit derived from a monomer having no acid-labile group but having a lactone ring: 36 to 65% by mole, still more preferably Structural unit represented by formula (aa): 5 to 30% by mole Structural unit derived from a monomer having an acid-labile group: 30 to 60% by mole Structural unit derived from a monomer having no acid-labile group but having a hydroxyl group: 5 to 25% by mole, Structural unit derived from a monomer having no acid-labile group but having a lactone ring: 35 to 60% by mole, based on the total mole number of all the structural units of RESIN (A).

As a combination of structural units for RESIN (A), preferred are the combinations of structural units as shown in each of (A-1), (A-2), (A-3), (A-4), (A-5), (A-6), (A-7), (A-8), (A-9), (A-10), (A-11), (A-12), (A-13), (A-14), (A-15) and (A-16).

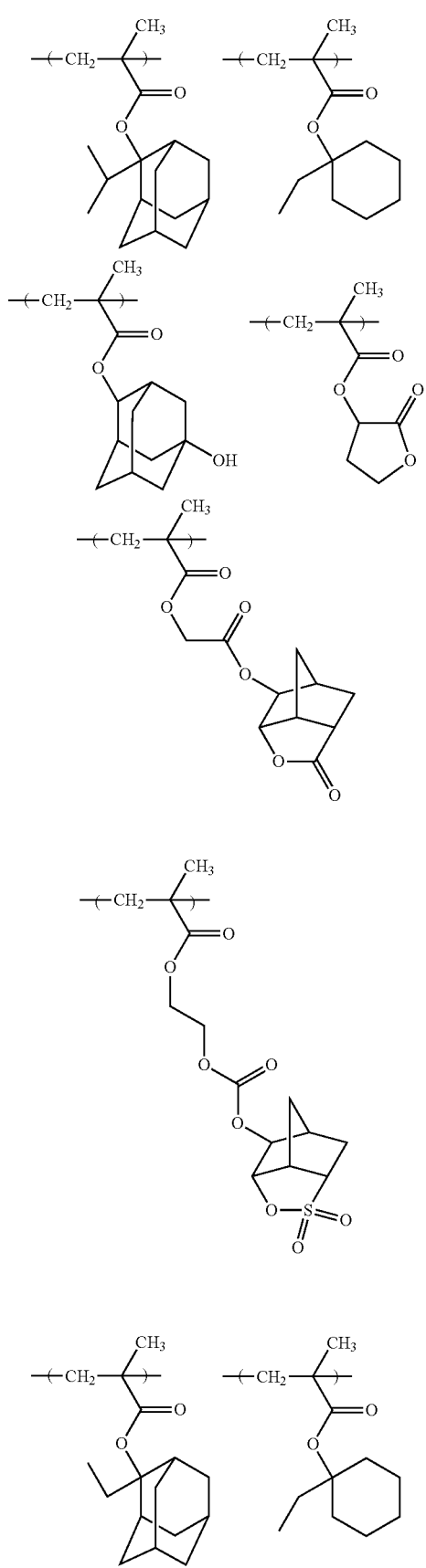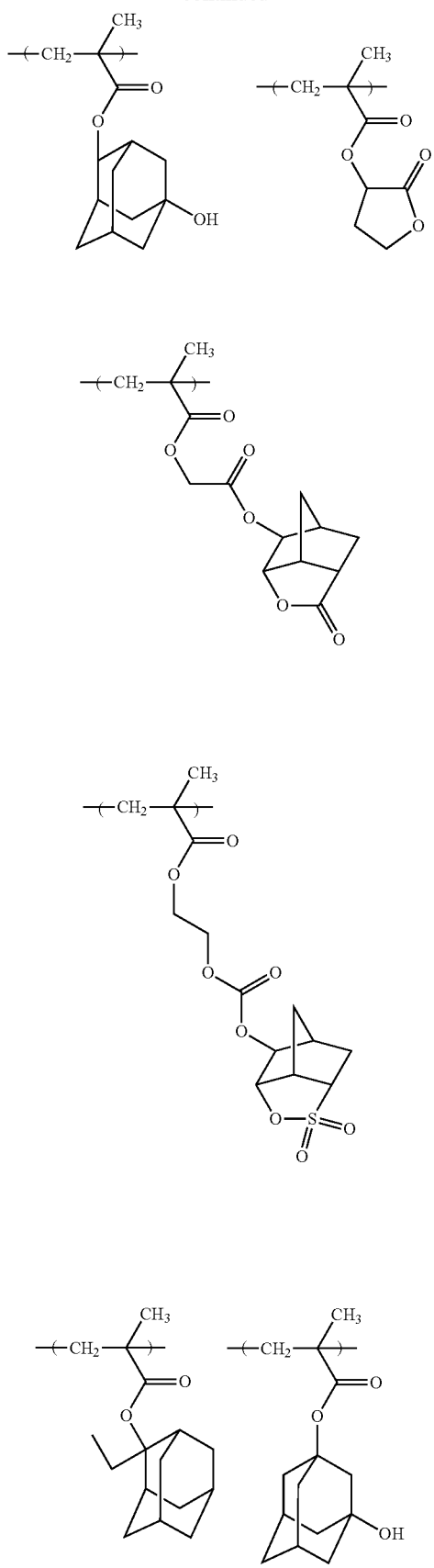

-continued
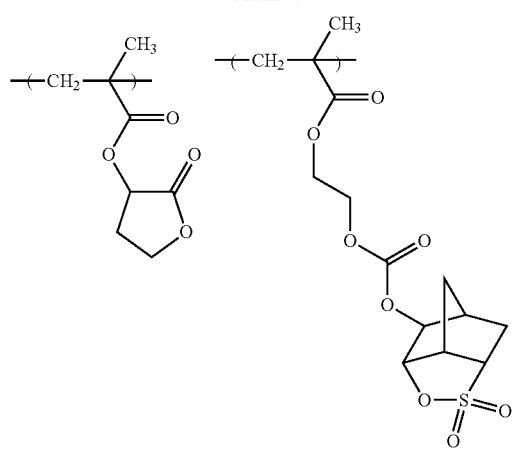
(A-4)
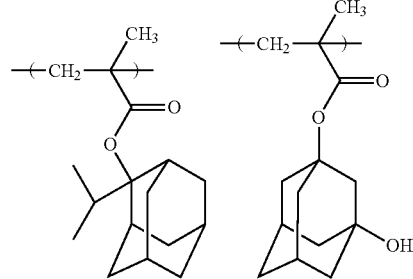
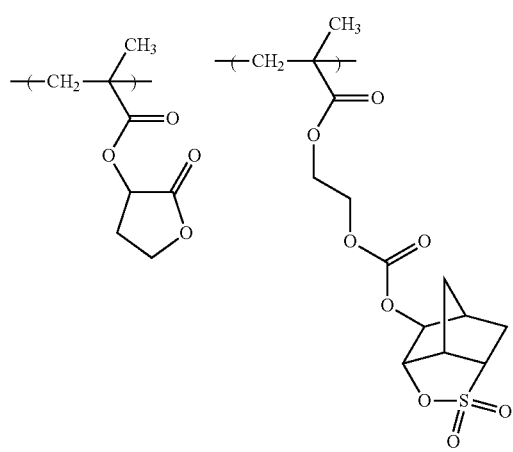
(A-5)
-continued
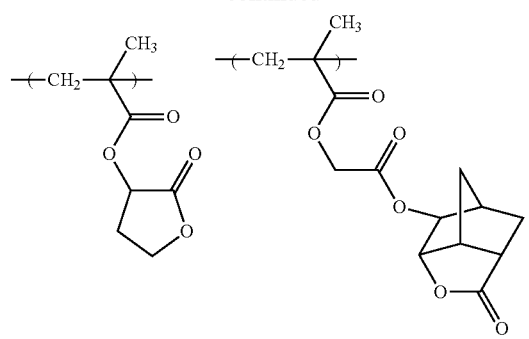
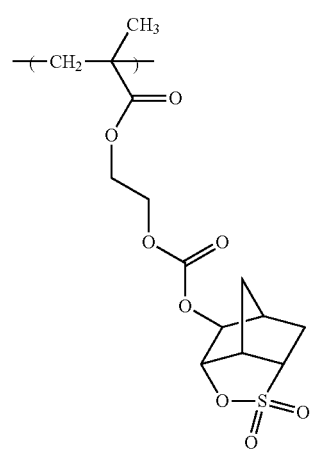
(A-6)
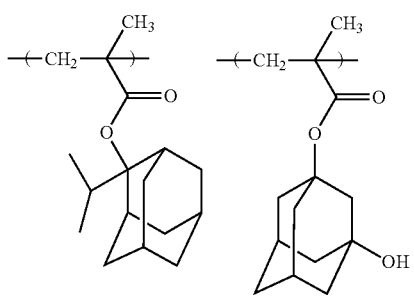
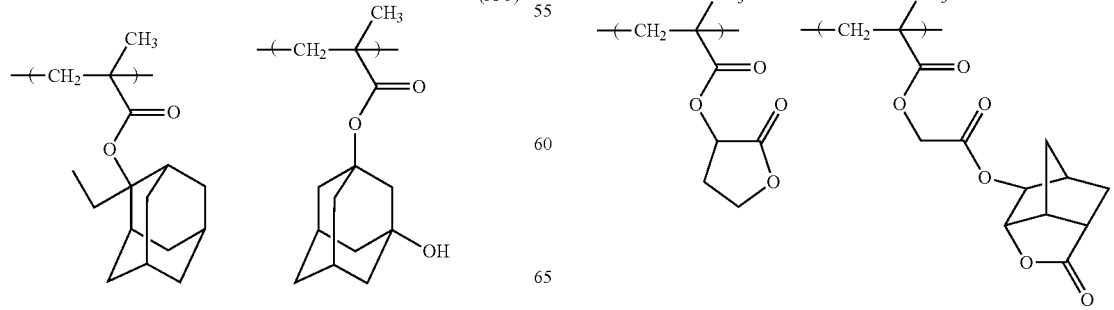

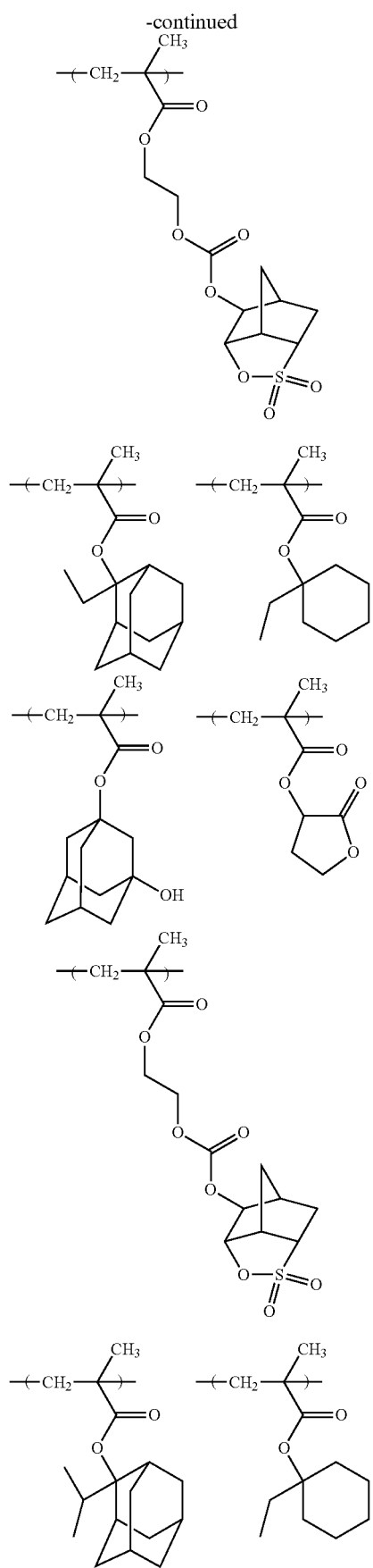
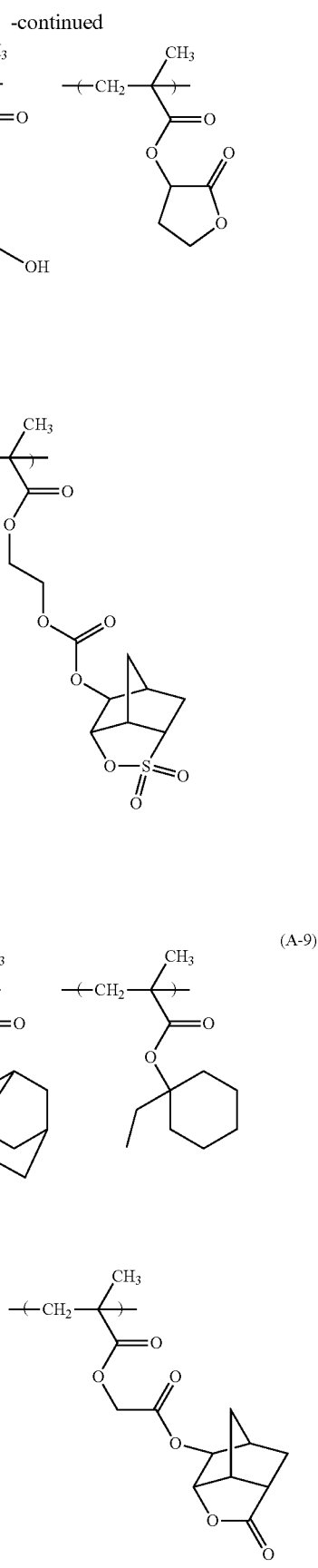

-continued
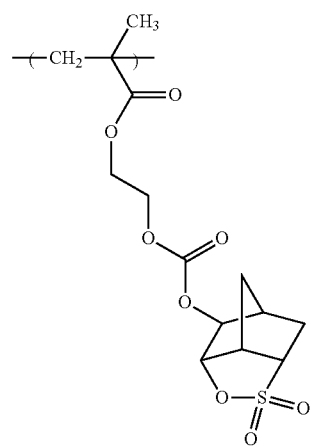
(A-10)
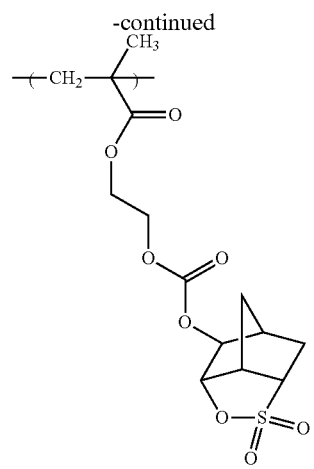
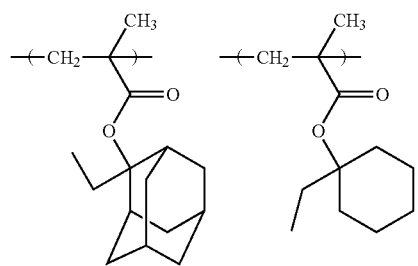
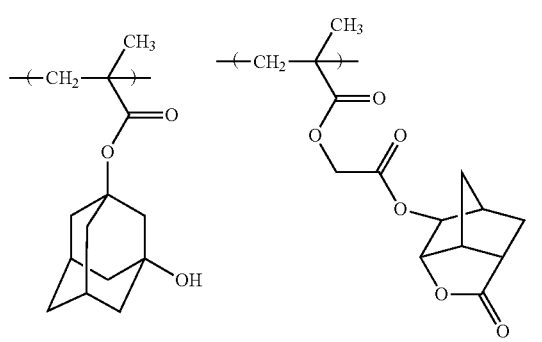
-continued
(A-11)
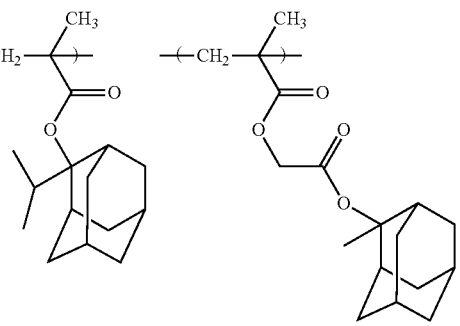
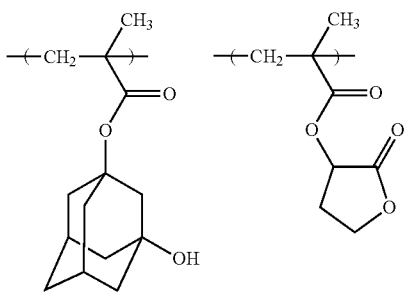
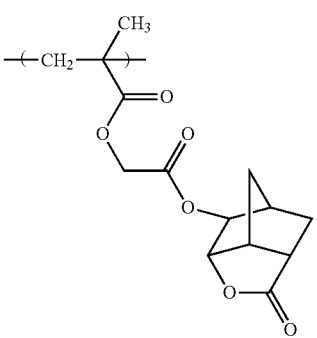

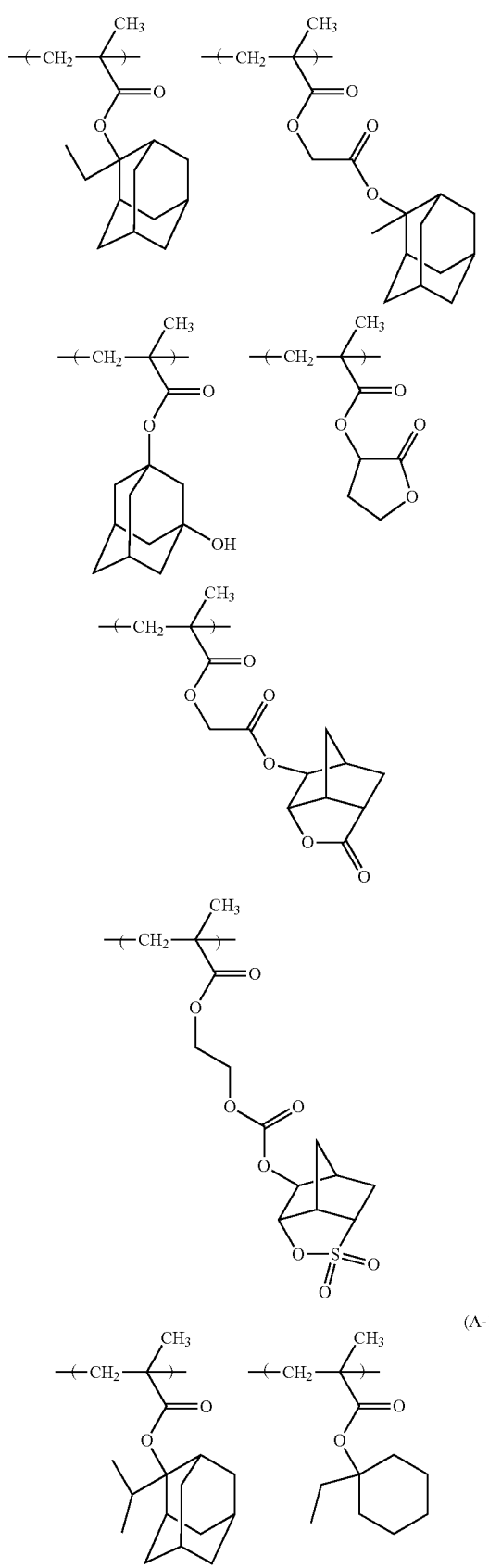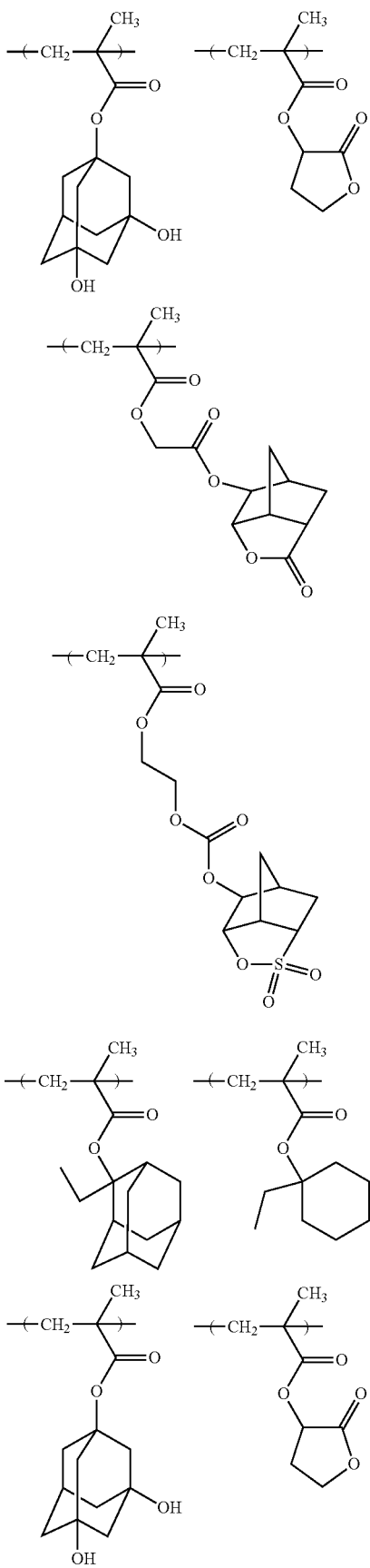

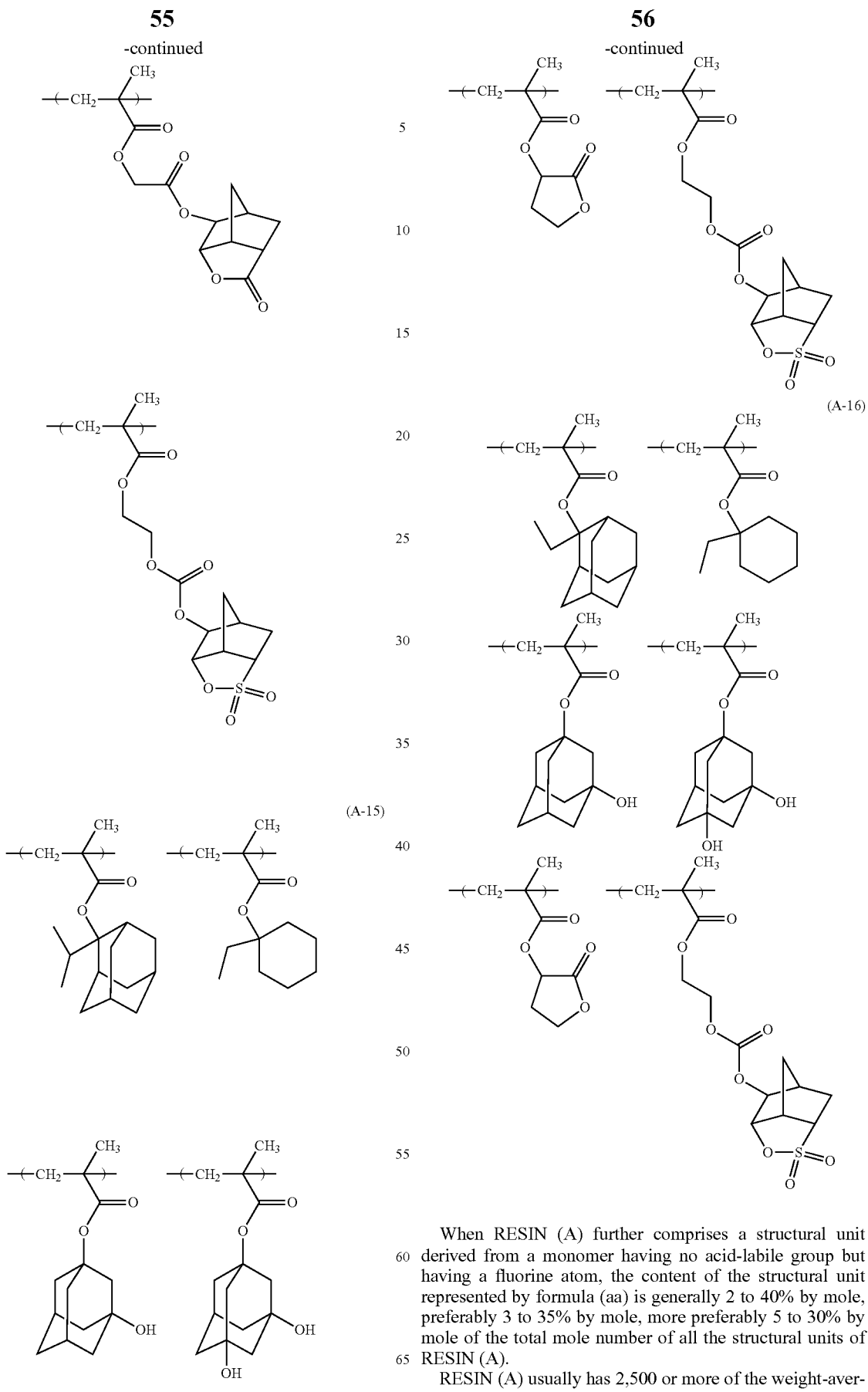

When RESIN (A) further comprises a structural unit derived from a monomer having no acid-labile group but having a fluorine atom, the content of the structural unit represented by formula (aa) is generally 2 to 40% by mole, preferably 3 to 35% by mole, more preferably 5 to 30% by mole of the total mole number of all the structural units of RESIN (A).

RESIN (A) usually has 2,500 or more of the weight-average molecular weight, preferably 3,000 or more, more preferably 3,500 or more of the weight-average molecular weight. RESIN (A) usually has 50,000 or less of the weight-average molecular weight, preferably has 30,000 or less, more preferably has 15,000 or less of the weight-average molecular weight.

The weight-average molecular weight can be measured with gel permeation chromatography.

The photoresist composition of the present invention comprises RESIN (A) and an acid generator.

The photoresist composition may comprise a resin other than RESIN (A), i.e. a resin which comprises no structural unit represented by formula (aa). Hereinafter, the resin which comprises no structural unit represented by formula (aa) is referred to as "another resin". The another resin is not limited to specific one, which may be a resin which is insoluble or poorly soluble in an aqueous alkali solution but becomes soluble in an aqueous alkali solution by an action of acid, or resin which does not show such property.

The another resin may comprise a structural unit derived from a monomer having an acid-labile group or a structural unit derived from a monomer having no acid-labile group, e.g. those derived from the monomers represented by formulae (a2-0), (a2-1), (a3-1), (a3-2) and (a3-3).

When RESIN (A) is a resin being insoluble or poorly soluble in an aqueous alkali solution but becoming soluble in an aqueous alkali solution by the action of an acid, the photoresist composition may comprise only RESIN (A) as its resin components. When RESIN (A) is not a resin showing such property as mentioned above, the photoresist composition generally comprises RESIN (A) and a resin which is insoluble or poorly soluble in an aqueous alkali solution but becomes soluble in an aqueous alkali solution by the action of an acid. Thus the photoresist composition of the present invention generally comprises a resin which is insoluble or poorly soluble in an aqueous alkali solution but becomes soluble in an aqueous alkali solution by the action of an acid, although the resin is RESIN (A) or another resin.

When RESIN (A) is not a resin which is insoluble or poorly soluble in an aqueous alkali solution but becomes soluble in an aqueous alkali solution by the action of an acid, the RESIN (A) preferably further comprises a structural unit derived from a monomer having no acid-labile group but having a fluorine atom. The resin which comprises a structural unit derived from a monomer having no acid-labile group but having a fluorine atom is preferably the resin which comprises a structural unit derived from the monomer represented by formula (a4-1).

When RESIN (A) comprises not a structural unit derived from a monomer having an acid-labile group, but a structural unit derived from a monomer having no acid-labile group but having a fluorine atom, the content of the structural unit represented by formula (aa) is usually 2 to 40% by mole, preferably 3 to 35% by mole, and more preferably 5 to 30% by mole of the total mole number of all the structural units of RESIN (A).

The another resin preferably comprises a structural unit derived from a monomer having an acid-labile group and a structural unit derived from a monomer having no acid-labile group but having a hydroxy group and/or a lactone ring.

The another resin which comprises the structural unit derived from a monomer having no acid-labile group but having a fluorine atom has the average weight molecular weight in the range of preferably 8000 to 80000, more preferably 10000 to 60000.

The photoresist composition of the present invention preferably comprises, as resin, only RESIN (A) or RESIN (A) together with another resin which comprises structural unit derived from a monomer having no acid-labile group but having a fluorine atom.

When RESIN (A) is a resin which is insoluble or poorly soluble in an aqueous alkali solution but becomes soluble in an aqueous alkali solution by the action of an acid, the content of RESIN (A) in the photoresist composition of the present invention is usually 80% by mass or more, and usually 99% by mass or less, based on the total amount of solid component.

When RESIN (A) is not a resin which is insoluble or poorly soluble in an aqueous alkali solution but becomes soluble in an aqueous alkali solution by the action of an acid, the content of RESIN (A) is usually 0.1 to 10% by weight, preferably 0.3 to 5% by weight, and more preferably 0.5 to 5% by weight, based on the total amount of solid component.

When the photoresist composition comprises another resin which comprises the structural unit derived from a monomer having no acid-labile group but having a fluorine atom, the content of the resin is usually 0.1 to 10% by weight, preferably 0.3 to 5% by weight, and more preferably 0.5 to 3% by weight, based on the total amount of solid component.

In this specification, "solid component" means components other than solvent in the photoresist composition. The contents of solid component can be determined by known mass spectrometry such as liquid chromatography or gas chromatography.

The photoresist composition of the present invention comprises an acid generator.

In the photoresist composition, an acid generates from the acid generator by exposure. The acid catalytically acts against an acid-labile group in the resin to cleave the acid-labile group, and the resin becomes one being soluble in an aqueous alkali solution.

The acid generator is a substance which is decomposed to generate an acid by applying a radiation such as a light, an electron beam or the like on the substance itself or on a photoresist composition containing the substance.

The acid generator includes a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonylmethide anion. The onium salt compound is preferable.

Other examples of the acid generator include acid generators described in JP 63-26653A, JP 55-164824A, JP 62-69263A, JP 63-146038 A, JP 63-163452 A, JP 62-153853 A, JP 63-146029 A, U.S. Pat. No. 3,779,778, U.S. Pat. No. 3,849,137, DE Patent No. 3914407 and EP Patent No. 126,712.

A fluorine-containing acid generator is preferable.

Preferable examples of the acid generator include a salt represented by the formula (B1):

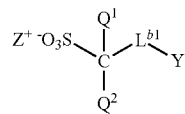
(B1)

wherein $Q^1$ and $Q^2$ each independently represent a fluorine atom or a C1-C6 perfluoroalkyl group,
$L^{b1}$ represents a single bond or a C1-C24 divalent aliphatic hydrocarbon group which can have a substituent, and a methylene group in the divalent aliphatic hydrocarbon group can be replaced by —O— or —CO—,
Y represents a hydrogen atom, or a C3-C18 alicyclic hydrocarbon group which can have a substituent and in which a methylene group can be replaced by —O—, —CO— or —SO$_2$—, and
$Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the divalent aliphatic hydrocarbon group represented by $L^{b1}$ include an alkandiyl group, a monocyclic or polycyclic divalent saturated hydrocarbon group and a group formed by combining two or more groups selected from the group consisting of the alkandiyl group and the monocyclic or polycyclic divalent saturated hydrocarbon group.

Examples thereof include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,1'-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group,
a branched chain alkanediyl group such as a butane-1,3-diyl group, a 2-methylpropane-1,3-diyl group, a2-methylpropane-1,2-diyl group, a pentane-1,4-diyl group and a 2-methylbutane-1,4-diyl group, a monocyclic divalent saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group, and
a polycyclic divalent saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group.

Examples of the aliphatic hydrocarbon group in which a methylene group has been replaced by —O— or —CO— include those represented by formulae (b1-1), (b1-2), (b1-3), (b1-4), (b1-5), (b1-6) and (b1-7).

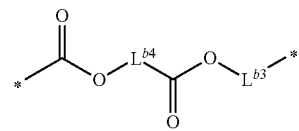
(b1-2)

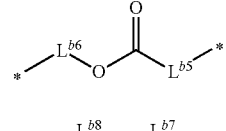
(b1-3)

(b1-4)

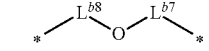

(b1-5)

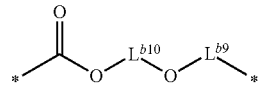

(b1-6)

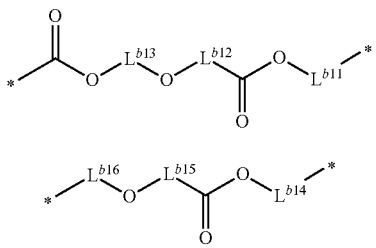

(b1-7)

where
$L^{b2}$ represents a single bond or a C1-C22 aliphatic hydrocarbon group,
$L^{b3}$ represents a single bond or a C1-C19 aliphatic hydrocarbon group,
$L^{b4}$ represents a C1-C20 aliphatic hydrocarbon group, with proviso that total carbon number of $L^{b3}$ and $L^{b4}$ is up to 20,
$L^{b5}$ represents a single bond or a C1-C21 aliphatic hydrocarbon group, $L^{b6}$ represents a C1-C22 aliphatic hydrocarbon group, with proviso that total carbon number of $L^{b5}$ and $L^{b6}$ is up to 22,
$L^{b7}$ represents a single bond or a C1-C22 aliphatic hydrocarbon group,
$L^{b8}$ represents a C1-C23 aliphatic hydrocarbon group, with proviso that total carbon number of $L^{b7}$ and $L^{b8}$ is up to 23,
$L^{b9}$ represents a single bond or a C1-C20 aliphatic hydrocarbon group,
$L^{b10}$ represents a C1-C21 aliphatic hydrocarbon group, with proviso that total carbon number of $L^{b9}$ and $L^{b10}$ is up to 21,
$L^{b11}$ and $L^{b12}$ represent a single bond or a C1-C18 aliphatic hydrocarbon group, $L^{b13}$ represents a C1-C19 aliphatic hydrocarbon group, with proviso that total carbon number of $L^{b11}$, $L^{b12}$ and $L^{b13}$ is up to 19,
$L^{b14}$ and $L^{b15}$ represent a single bond or a C1-C20 aliphatic hydrocarbon group, $L^{b16}$ represents a C1-C21 aliphatic hydrocarbon group, with proviso that total carbon number of $L^{b14}$, $L^{b15}$ and $L^{b16}$ is up to 21, and * represents a binding position to —C($Q^1$)($Q^2$)—.

Examples of the aliphatic hydrocarbon group represented by formula (b1-1) include those represented as follow.

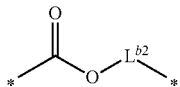
(b1-1)

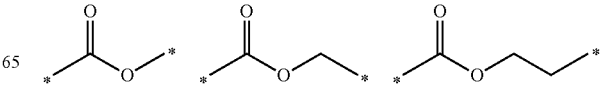

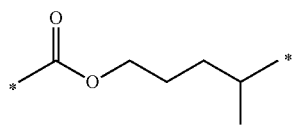

Examples of the aliphatic hydrocarbon group represented by formula (b1-2) include those represented as follow.

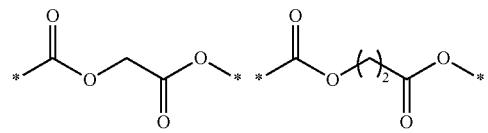

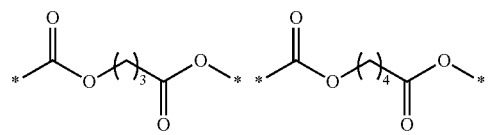

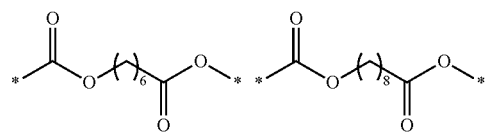

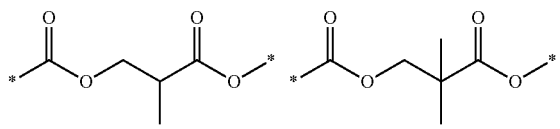

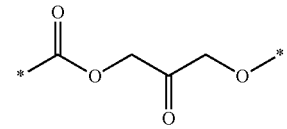

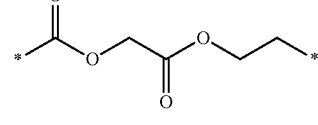

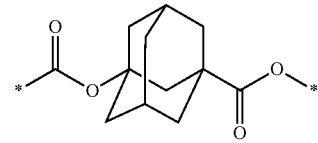

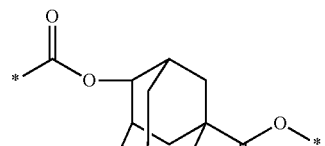

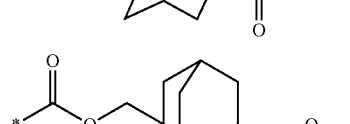

Examples of the aliphatic hydrocarbon group represented by formula (b1-3) include those represented as follow.

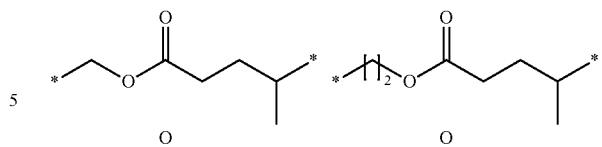

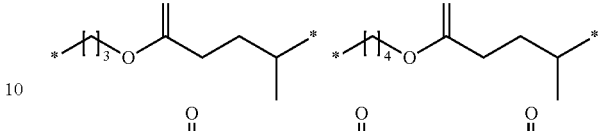

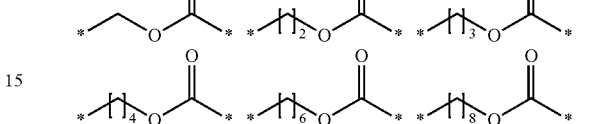

Examples of the aliphatic hydrocarbon group represented by formula (b1-4) include those represented as follow.

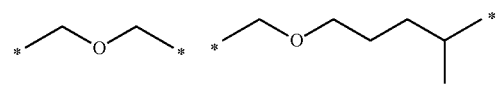

Examples of the aliphatic hydrocarbon group represented by formula (b1-5) include those represented as follow.

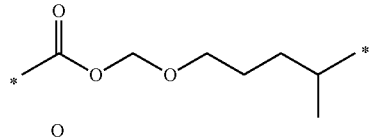

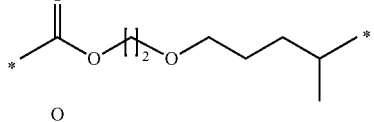

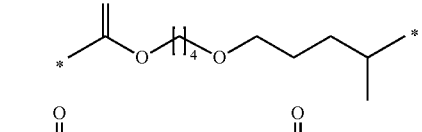

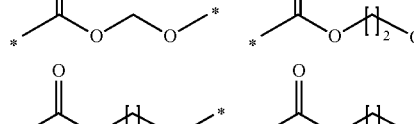

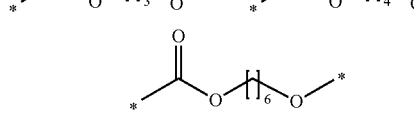

Examples of the aliphatic hydrocarbon group represented by formula (b1-6) include those represented as follow.

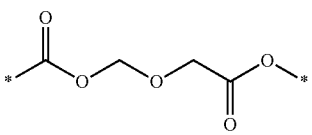

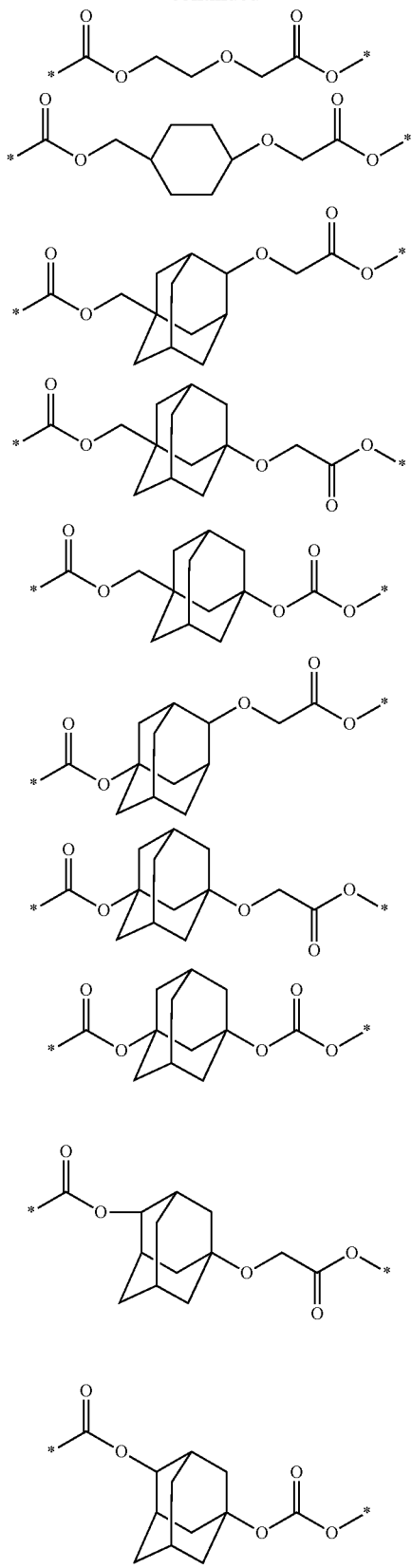

Examples of the aliphatic hydrocarbon group represented by formula (b1-7) include those represented as follow.

Among them, $L^{b1}$ is represented preferably by formula (b1-1), (b1-2), (b1-3), or (b1-4), more preferably by formula (b1-1) or (b1-2) still more preferably by formula (b1-1), in particular preferably by formula (b1-1) in which $L^{b2}$ represents a single bond or C1 to C6 saturated hydrocarbon group such as C1 to C6 alkyl group.

The C3-C18 alicyclic hydrocarbon group represented by Y is preferably a C3-C12 alicyclic hydrocarbon group such as cyclopropyl group, cyclobutyl group, cyclopentyl group, cyclohexyl group, cycloheptyl group, and cyclooctyl group.

Examples of the alicyclic hydrocarbon group in which a methylene group are replaced by —O—, —CO— or —SO$_2$— include a group having a cyclic ether structure, a saturated cyclic hydrocarbon group having an oxo group, a sultone ring group and a lactone ring group.

Examples of the substituent in Y include a halogen atom other than a fluorine atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH$_2$)$_{j2}$—O—CO—R$^{b1}$— in which R$^{b1}$ represents a C1-C16 aliphatic hydrocarbon group, a C3-C16 saturated cyclic hydrocarbon group or a C6-C18 aromatic hydrocarbon group and j2 represents an integer of 0 to 4.

Examples of the halogen atom include a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above.

Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

The alicyclic hydrocarbon group represented by Y includes those represented by formulae (Y1), (Y2), (Y3), (Y4), (Y5), (Y6), (Y7), (Y8), (Y9), (Y10), (Y11), (Y12), (Y13), (Y14), (Y15), (Y16), (Y17), (Y18), (Y19), (Y20), (Y21), (Y22), (Y23), (Y24), (Y25) and (Y26);

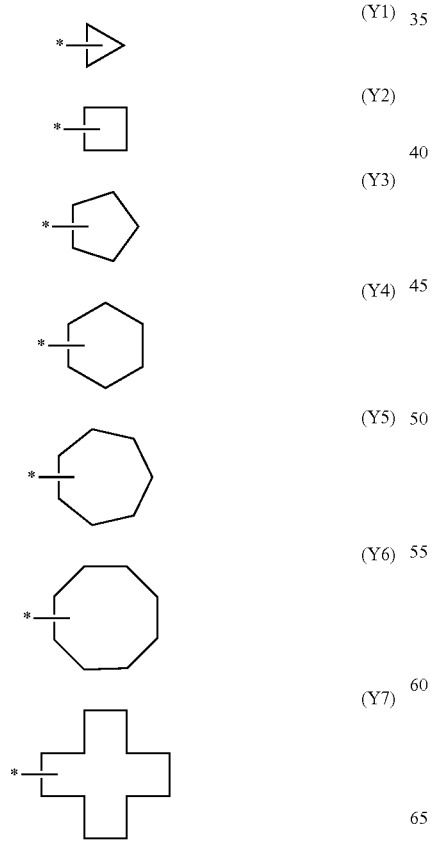
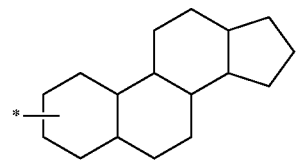
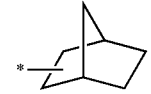
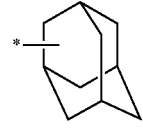
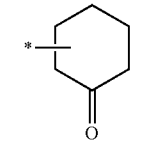
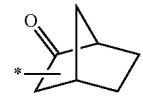
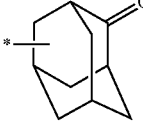
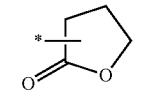
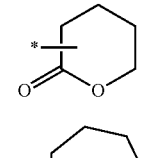
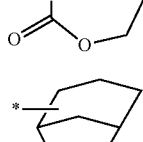

-continued (Y20) 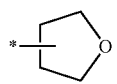

(Y21) 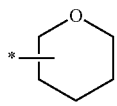

(Y22) 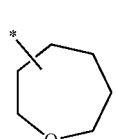

(Y23) 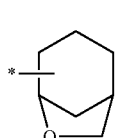

(Y24) 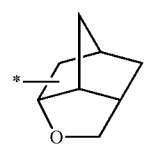

(Y25) 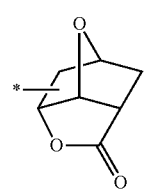

(Y26) 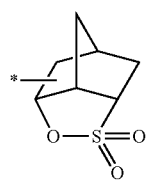

where * represents a binding position.

Among them, Y is preferably a group represented by formula (Y11), (Y14), (Y15), (Y16) or (Y19), more preferably a group represented by formula (Y11), (Y14), (Y15) or (Y19), and still more preferably a group represented by formula (Y11) or (Y14).

Y includes those represented by the following formulae.

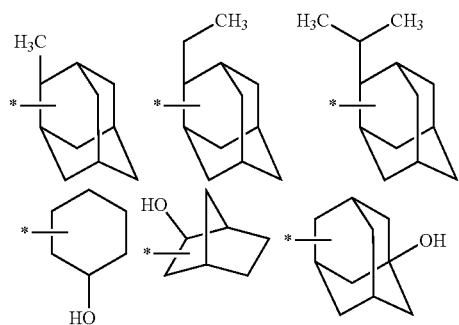

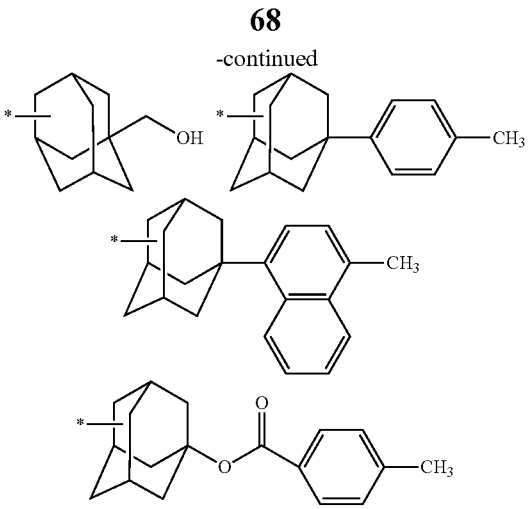

Y is preferably a hydrogen atom or a C5-C12 alicyclic hydrocarbon group which may have a substituent, more preferably a C5-C12 alicyclic hydrocarbon group which may have a substituent, still more preferably an adamantyl group which can have a substituent, and is more preferably an adamantyl group, an oxoadamantyl group or a hydroxyadamantyl group.

Among the sulfonic acid anions of the acid generator represented by the formula (B1), preferred are anions represented by the formulae (b1-1-1), (b1-1-2), (b1-1-3), (b1-1-4), (b1-1-5), (b1-1-6), (b1-1-7), (b1-1-8) and (b1-1-9).

(b1-1-1)
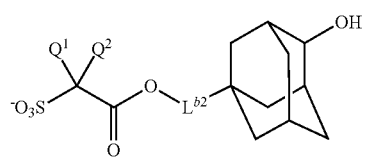

(b1-1-2)
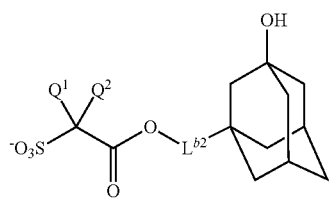

(b1-1-3)
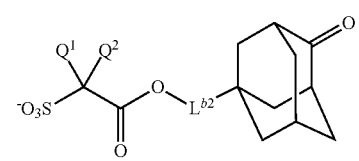

(b1-1-4)
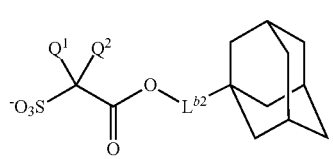

(b1-1-5)
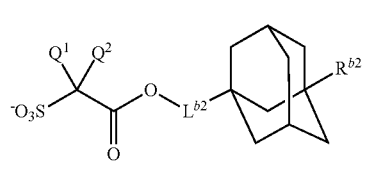

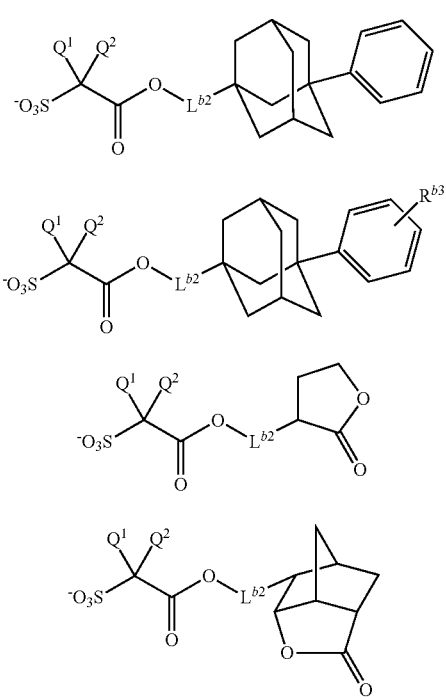

wherein $Q^1$, $Q^2$ and $L^{b2}$ are the same as defined above, and $R^{b2}$ and $R^{b3}$ each independently represent a C1-C4 alkyl group and it is more preferred that $R^{b2}$ and $R^{b3}$ each independently represent a methyl group.

The anions represented by the formulae (b1-1-1) to (b1-1-9) are specifically described in JP 2010-204646 A.

Specific examples of the sulfonic acid anion represented by formula (B1) where Y represents an unsubstituted alicyclic hydrocarbon group include those represented by the formulae (b1-s-0), (b1-s-1), (b1-s-2), (b1-s-3), (b1-s-4), (b1-s-5), (b1-s-6), (b1-s-7), (b1-s-8) and (b1-s-9).

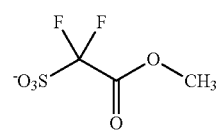
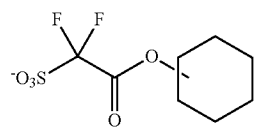
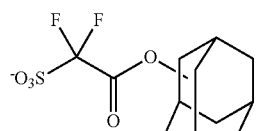
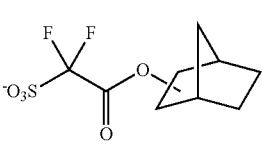

Specific examples of the sulfonic acid anion represented by formula (B1) where Y represents an alicyclic hydrocarbon group having a hydroxyl group include anions represented by the formulae (b1-s-10), (b1-s-11), (b1-s-12), (b1-s-13), (b1-s-14), (b1-s-15), (b1-s-16), (b1-s-17) and (b1-s-18)

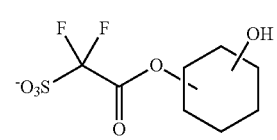
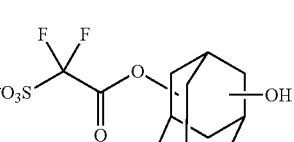
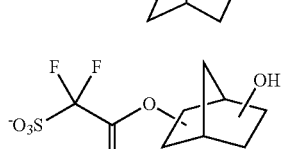

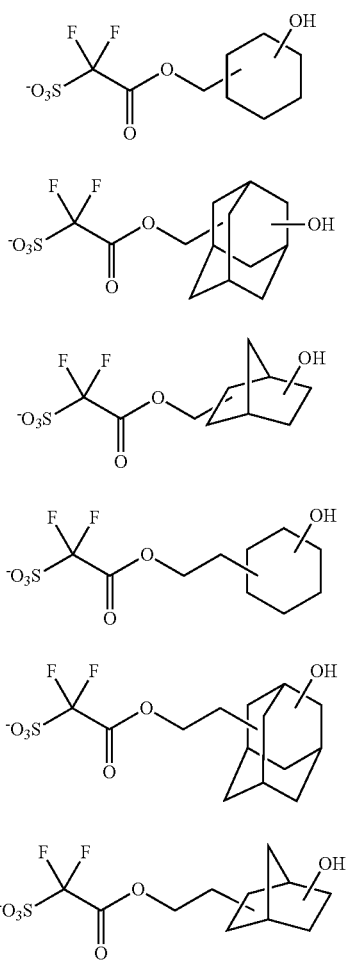

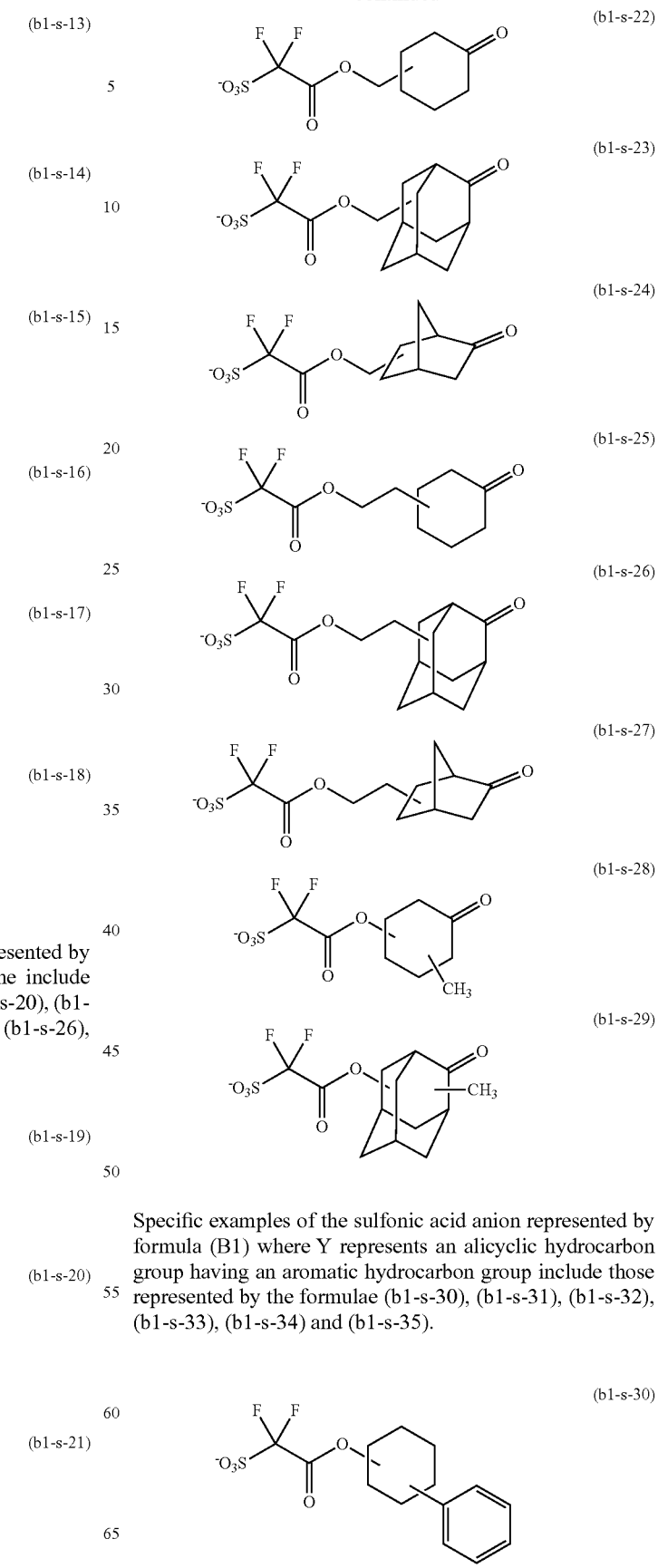

Specific examples of the sulfonic acid anion represented by formula (B1) where Y represents a cyclic ketone include anions represented by the formulae (b1-s-19), (b1-s-20), (b1-s-21), (b1-s-22), (b1-s-23), (b1-s-24), (b1-s-25), (b1-s-26), (b1-s-27), (b1-s-28) and (b1-s-29).

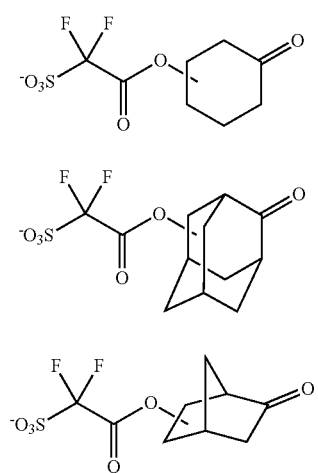

Specific examples of the sulfonic acid anion represented by formula (B1) where Y represents an alicyclic hydrocarbon group having an aromatic hydrocarbon group include those represented by the formulae (b1-s-30), (b1-s-31), (b1-s-32), (b1-s-33), (b1-s-34) and (b1-s-35).

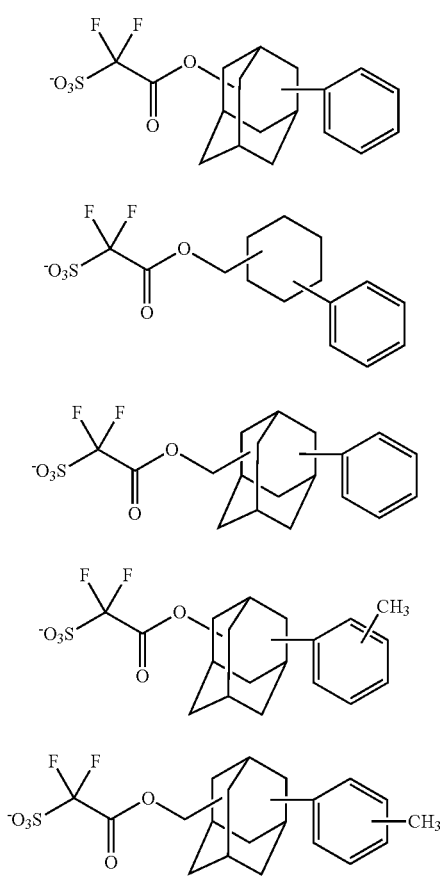

Specific examples of the sulfonic acid anion represented by formula (B1) where Y represents a lactone ring or a sultone ring include those represented by the formulae (b1-s-36), (b1-s-37), (b1-s-38), (b1-s-39), (b1-s-40) and (b1-s-41)

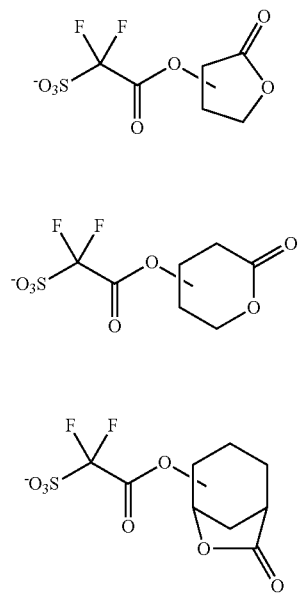

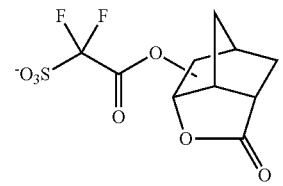

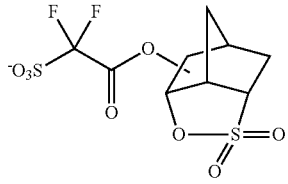

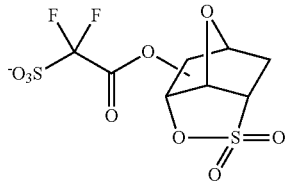

Examples of the organic counter ion represented by $Z^+$ include an onium cation such as a sulfonium cation, an iodonium cation, an ammonium cation, a benzothiazolium cation and a phosphonium cation, and a sulfonium cation and an iodonium cation are preferable, and a sulfonium cation is more preferable.

Preferable examples of the organic counter ion represented by $Z^+$ include the organic cations represented by the formulae (b2-1), (b2-2), (b2-3) and (b2-4):

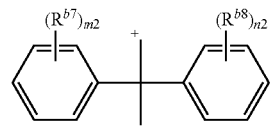

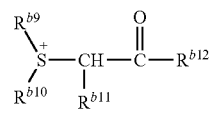

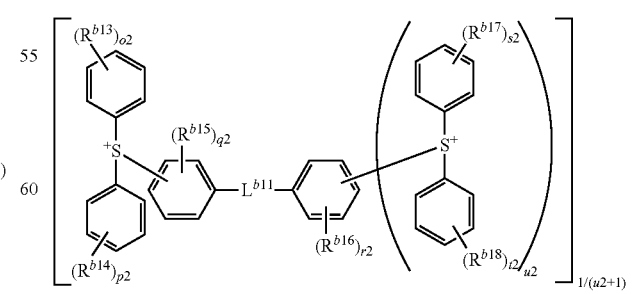

In the formulae (b2-1) to (b2-4), $R^{b4}$, $R^{b5}$ and $R^{b6}$ independently represent a C1-C30 aliphatic hydrocarbon group, a C3-C18 alicyclic hydrocarbon group and a C6-C18 aromatic hydrocarbon group. The alkyl group can have a substituent selected from the group consisting of a hydroxyl group, a C1-C12 alkoxy group and a C6-C18 aromatic hydrocarbon group. The C3-C18 alicyclic hydrocarbon group can have a substituent selected from the group consisting of a halogen atom, a C2-C4 acyl group and a glycidyloxy group. The C6-C18 aromatic hydrocarbon group can have a substituent selected from the group consisting of a halogen atom, a hydroxyl group, a C1-C18 aliphatic hydrocarbon group, a C3-C18 saturated cyclic hydrocarbon group and a C1-C12 alkoxy group.

$R^{b7}$ and $R^{b6}$ are independently in each occurrence a hydroxyl group, a C1-C12 alkyl group or a C1-C12 alkoxy group, m2 and n2 independently represents an integer of 0 to 5.

$R^{b9}$ and $R^{b10}$ independently represent a C1-C18 aliphatic hydrocarbon group or a C3-C18 alicyclic hydrocarbon group.

$R^{b11}$ represents a hydrogen atom, a C1-C18 aliphatic hydrocarbon group, a C3-C18 alicyclic hydrocarbon group or a C6-C18 aromatic hydrocarbon group.

When $R^{b9}$, $R^{b10}$ and $R^{b11}$ each independently represent an alkyl group, it is preferably a C1-C12 alkyl group, and when $R^{b9}$, $R^{b10}$ and $R^{b11}$ each independently represent an alicyclic hydrocarbon group, it is preferably C3-C18 alicyclic hydrocarbon group and more preferably C4-C12 alicyclic hydrocarbon group.

$R^{b12}$ represents a C1-C18 aliphatic hydrocarbon group, a C3-C18 saturated cyclic hydrocarbon group and a C6-C18 aromatic hydrocarbon group and the aromatic hydrocarbon group can have a substituent selected from the group consisting of a C1-C12 aliphatic hydrocarbon group, a C1-C12 alkoxy group, a C3-C18 saturated cyclic hydrocarbon group and a (C1-C12 alkyl)carbonyloxy group.

$R^{b9}$ and $R^{b10}$ can be bonded to form a C2-C11 divalent acyclic hydrocarbon group which forms a ring together with the adjacent S$^+$, and a methylene group in the divalent acyclic hydrocarbon group may be replaced by —CO—, —O— or —S—, and preferred is a C2-C6 divalent acyclic hydrocarbon group.

$R^{b11}$ and $R^{b12}$ can be bonded each other to form a C1-C10 divalent acyclic hydrocarbon group which forms a 2-oxocycloalkyl group together with the adjacent —CHCO—, and a methylene group in the divalent acyclic hydrocarbon group may be replaced by —CO—, —O— or —S—, and preferred is a C1-C5 divalent acyclic hydrocarbon group.

$R^{b13}$, $R^{b14}$, $R^{b15}$, $R^{b}16$, $R^{b17}$ and $R^{b18}$ independently represent a hydroxyl group, a C1-C12 aliphatic hydrocarbon group or a C1-C12 alkoxy group.

$L^{b11}$ represents —S— or —O— and o2, p2, s2 and t2 each independently represents an integer of 0 to 5, q2 and r2 each independently represents an integer of 0 to 4, and u2 represents 0 or 1.

Preferable examples of the aliphatic hydrocarbon group represented by $R^{b4}$ to $R^{b12}$ include an alkyl group such as a methyl group, an ethyl group, a propyl group, an isopropyl group, 2,2-dimethylethyl group, 1-methylpropyl group, a 2-methylpropyl group, a 1,2-dimethylpropyl group, a 2,2-dimethylpropyl group, a 1-ethylpropyl group, a butyl group, a sec-butyl group, a tert-butyl group, a pentyl group, a 1-methylbutyl group, a 2-methylbutyl group, a 3-methylbutyl group, a hexyl group, a 1-propylbutyl group, a 1-methylpentyl group, a 2-ethylhexyl group, a 1,4-dimethylhexyl group, a 1-methylheptyl group, an octyl group, a decyl group, a dodecyl group, a hexadecyl group, a pentadecyl group, a heptadecyl group and an octadecyl group, and more preferable examples thereof include a methyl group, an ethyl group, a propyl group, an isopropyl group, a butyl group, a sec-butyl group, a tert-butyl group, a pentyl group, a hexyl group, an octyl group and a 2-ethylhexyl group.

The alicyclic hydrocarbon group may be monocyclic or polycyclic. Preferable examples thereof include a cycloalkyl group such as a cyclopentyl group, a cyclohexyl group, a methylcyclohexyl group, a dimethylcyclohexyl group, a cycloheptyl group and a cyclooctyl group, a group obtained by hydrogenating a condensed aromatic hydrocarbon group such as a hydronaphthyl group, abridged cyclic hydrocarbon group such as an adamantyl group, a norbornyl group and a methylnorbornyl group, and the following groups.

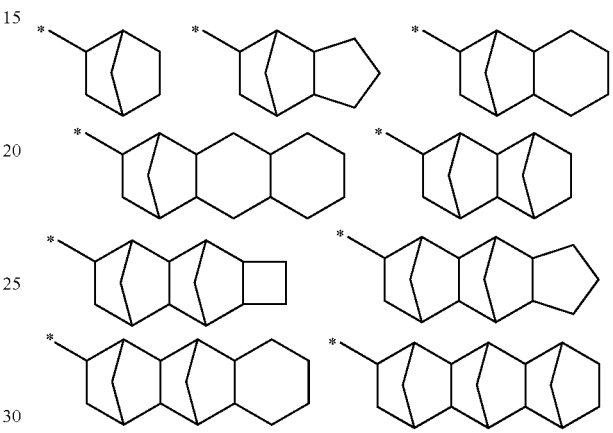

Among them, preferred are a cyclopropyl group, a cyclobutyl group, a cyclopentyl group, a cyclohexyl group, a cyclodecyl group, a 2-alkyl-2-adamantyl group, a 1-(1-adamantyl)alkan-1-yl group and an isobornyl group.

Preferable examples of the aromatic group include an aryl group such as a phenyl group, a naphthyl group, an anthryl group, a 4-methylphenyl group, a 4-ethylphenyl group, a 4-tert-butylphenyl group, a 4-cyclohexylphenyl group, a 4-methoxyphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group, and a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group are more preferable.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group a propyonyl group and a butyryl group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S$^+$ and the divalent acyclic hydrocarbon group include a thiolan-1-ium ring (tetrahydrothiphenium ring), a thian-1-ium ring and a 1,4-oxathian-4-ium ring. AC3-C7 divalent acyclichydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

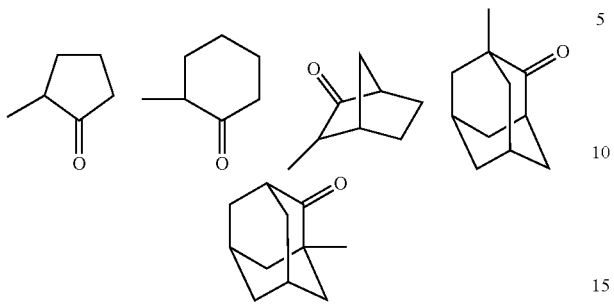

A C1-C5 divalent acyclic hydrocarbon group is preferable.

Examples of the C2-C13 acyloxy group include an acetyloxy group, a propyonyloxy group, a butyryloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

Examples of the cations represented by the formulae (b2-1) to (b2-4) include those described in JP 2010-204646A1.

Among the above-mentioned cations, preferred is the cation represented by the formula (b2-1), and more preferred is the cation represented by the formula (b2-1-1). A triphenylsulfonium cation and a tritolylsulfonium cation are especially preferable.

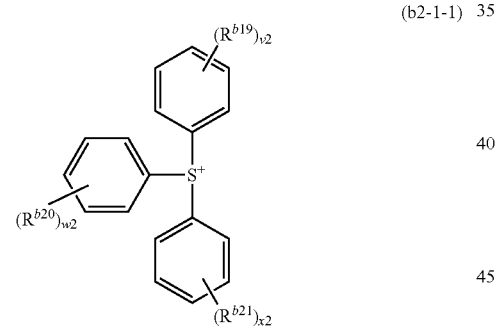

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, C3-C18 alicyclic hydrocarbon group or a C1-C12 alkoxy group, and a hydrogen atom of the aliphatic hydrocarbon group can be replaced by a hydroxyl group, a C1-C12 alkoxy group or a C6-C18 aromatic hydrocarbon group, and a hydrogen atom of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and a C1-C12 alkyl group is preferable. The v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

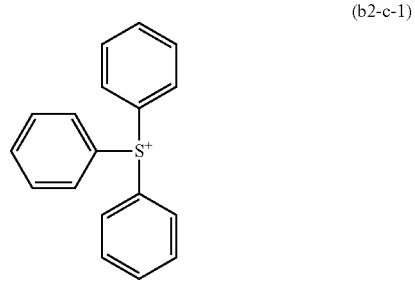

(b2-c-1)

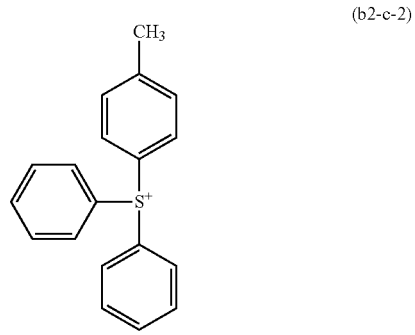

(b2-c-2)

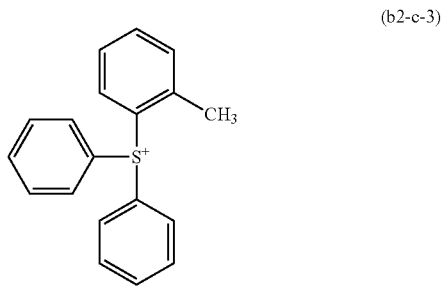

(b2-c-3)

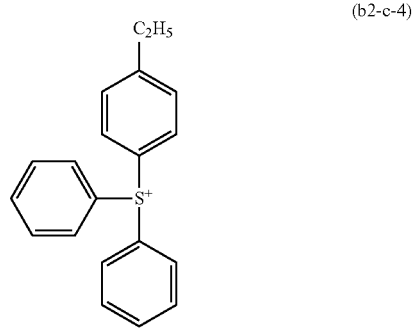

(b2-c-4)

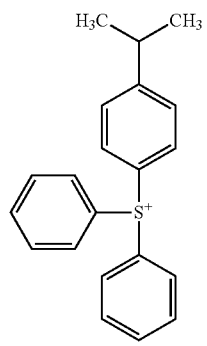 (b2-c-5)
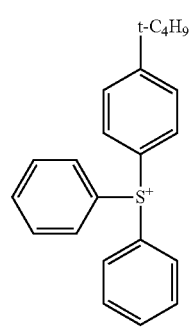 (b2-c-6)
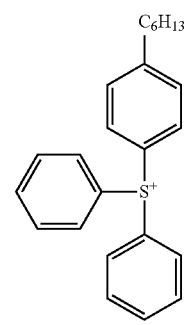 (b2-c-7)
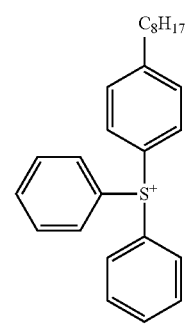 (b2-c-8)
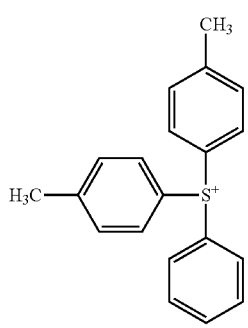 (b2-c-9)
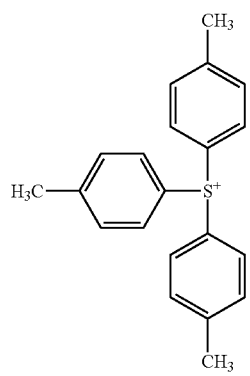 (b2-c-10)
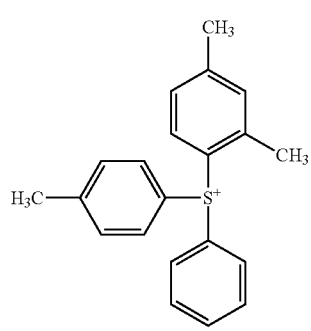 (b2-c-11)
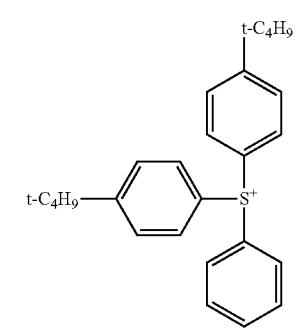 (b2-c-12)
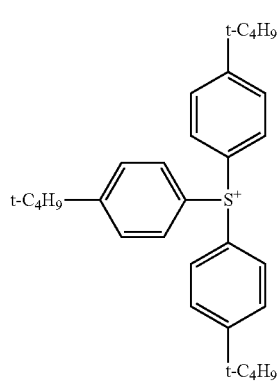 (b2-c-13)
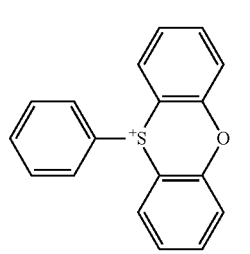 (b2-c-14)

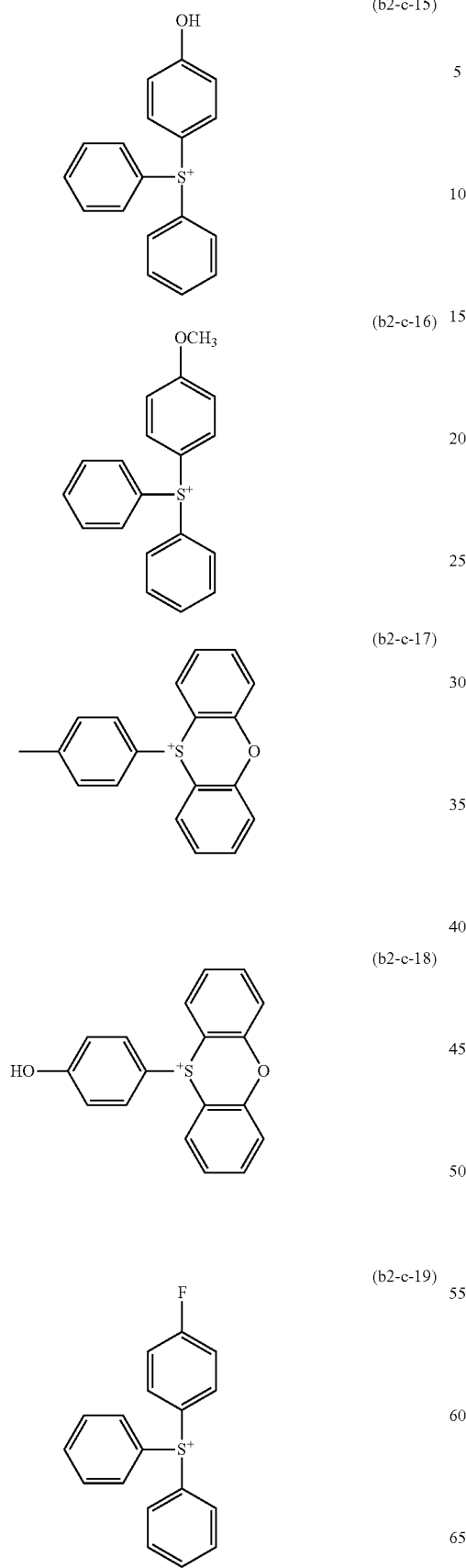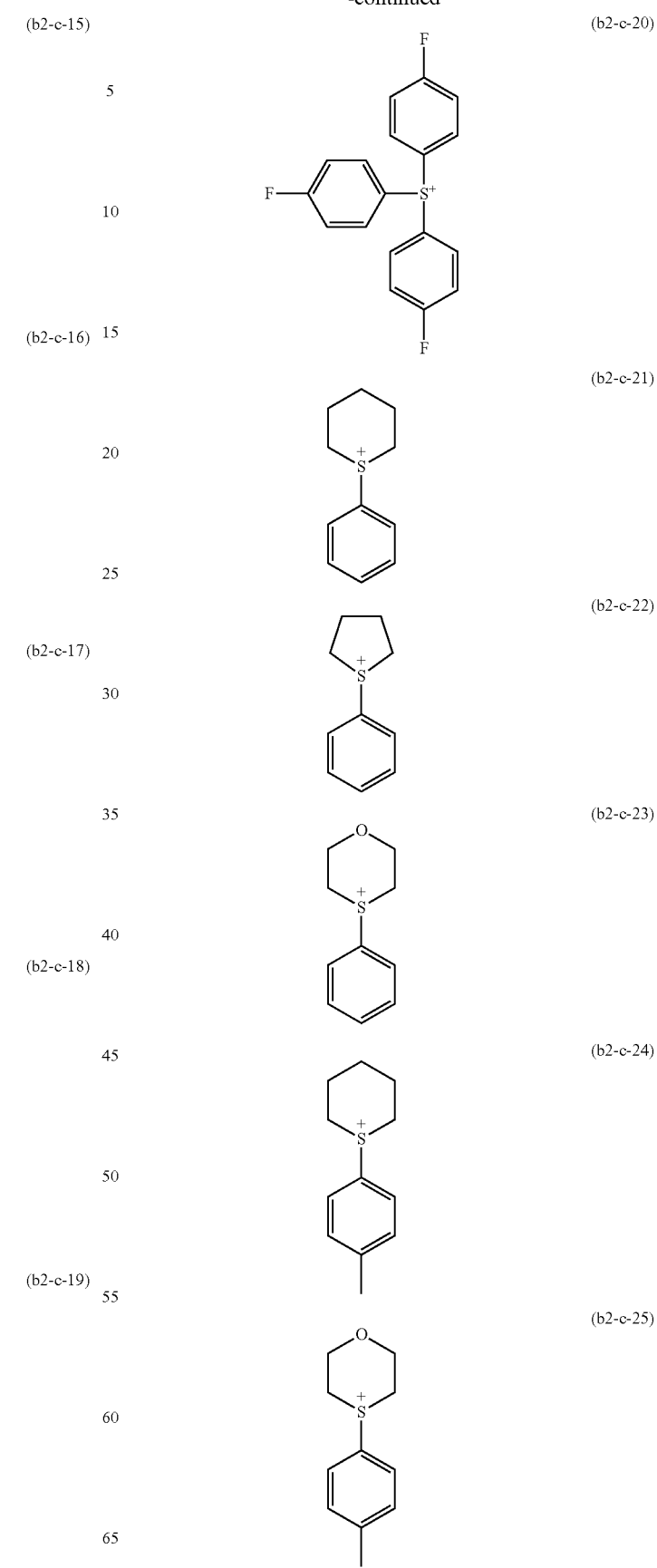

(b2-c-26)

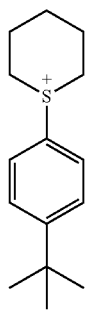

(b2-c-27)

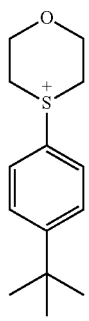

Examples of the cation represented by the formula (b2-2) include the followings.

(b2-c-28)

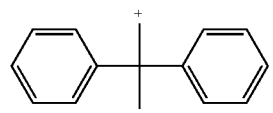

(b2-c-29)

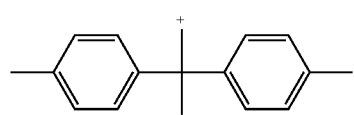

(b2-c-30)

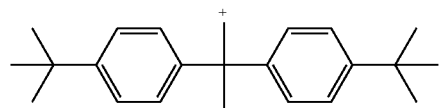

Examples of the cation represented by the formula (b2-3) include the followings.

(b2-c-31)

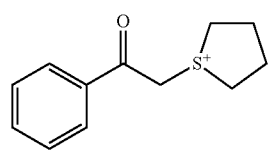

(b2-c-32)

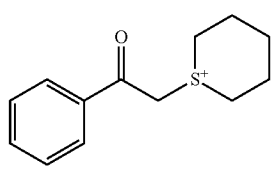

(b2-c-33)

(b2-c-34)

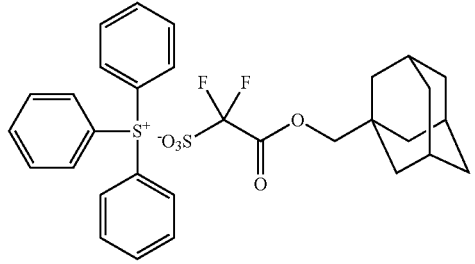

Examples of the salt represented by the formula (B1) include a salt wherein the anion is any one of the above-mentioned anions and the cation is any one of organic cations. Preferable examples thereof include those represented by formulae (B1-1), (B1-2), (B1-3), (B1-4), (B1-5), (B1-6), (B1-7), (B1-8), (B1-9), (B1-10), (B1-11), (B1-12), (B1-13), (B1-14), (B1-15), (B1-16), (B1-17), (B1-18), (B1-19), (B1-20), (81-21), (B1-22), (81-23) and (B1-24). Among them, preferred are the salts having triarylsulfonium cation, and more preferred are those represented by formulae (B1-1), (B1-2), (B1-3), (B1-6), (B1-7), (B1-11), (B1-12), (B1-13), (B1-14), (B1-21), (B1-22), (B1-23) and (B1-24).

(B1-1)

(B1-2)

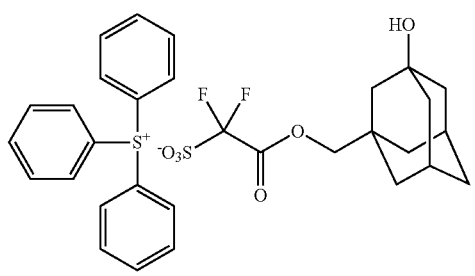

(B1-3) 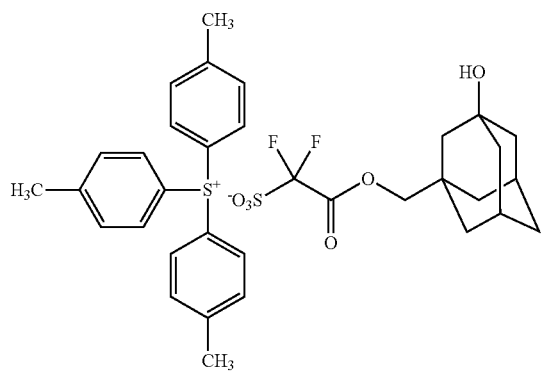
(B1-4) 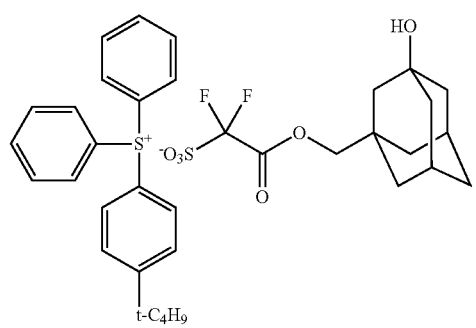
(B1-5) 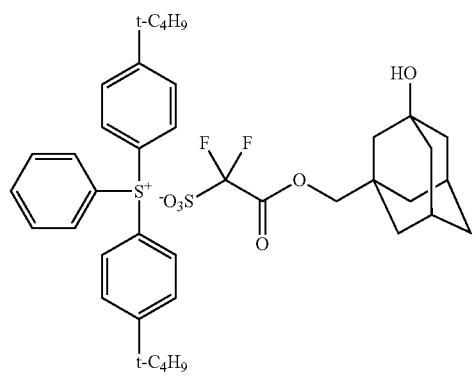
(B1-6) 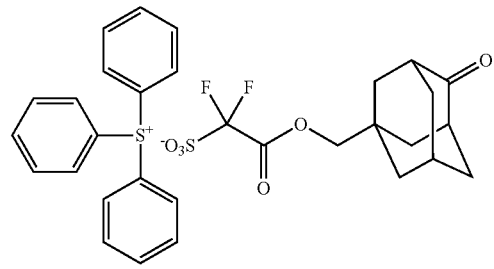
(B1-7) 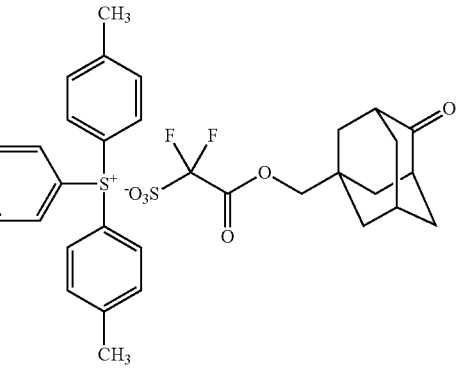
(B1-8) 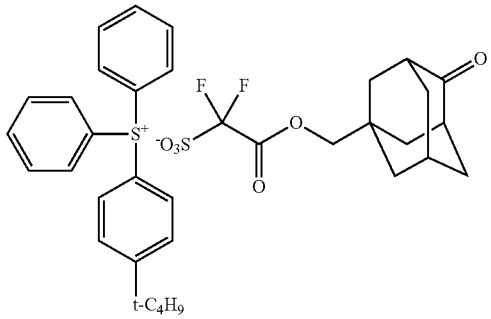
(B1-9) 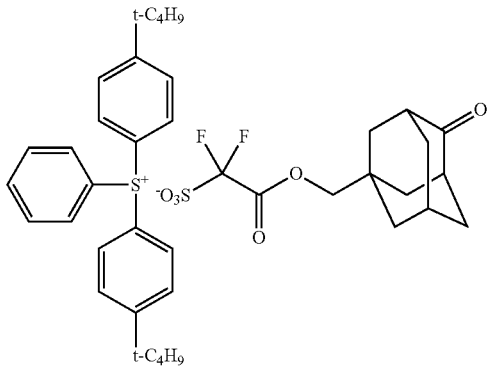
(B1-10) 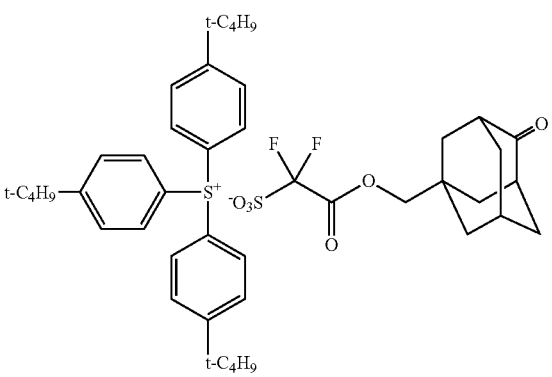

(B1-11)
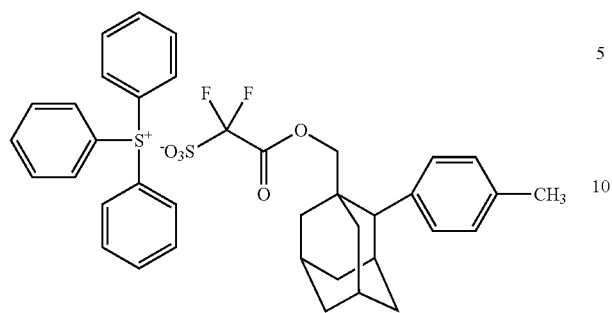
(B1-12)
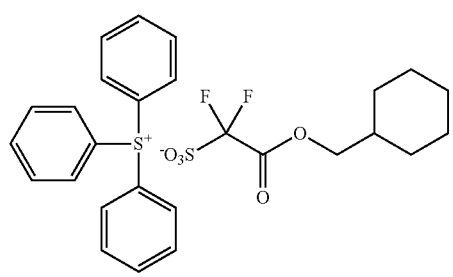
(B1-13)
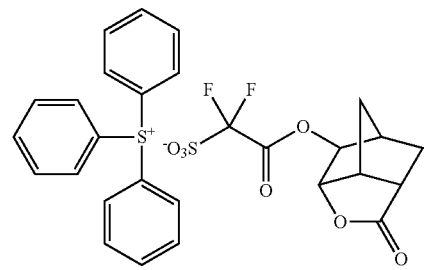
(B1-14)
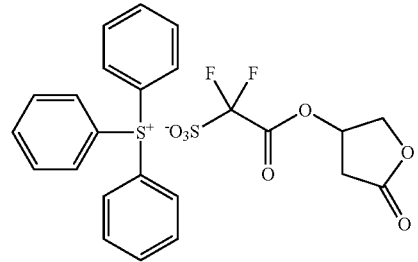
(B1-15)
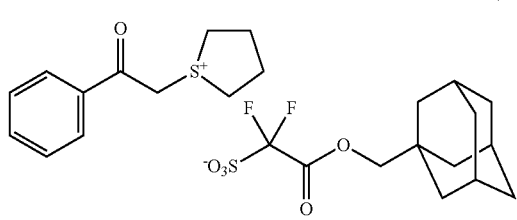
(B1-16)
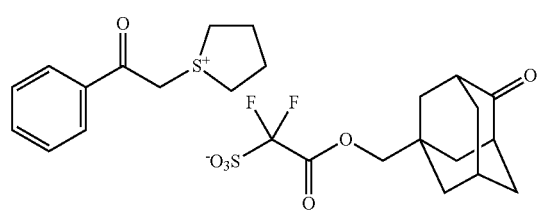
(B1-17)
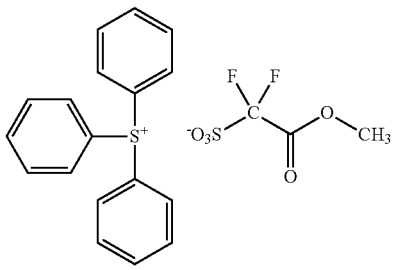
(B1-18)
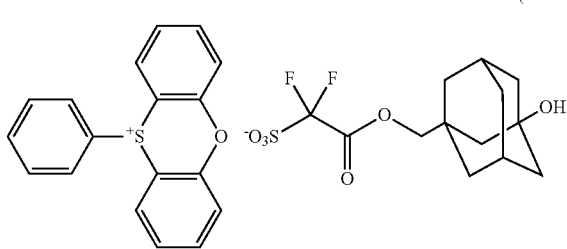
(B1-19)
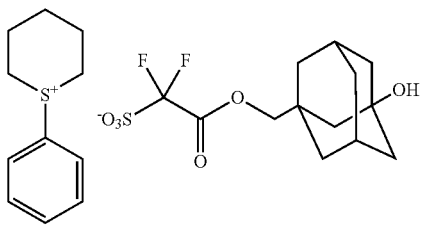
(B1-20)
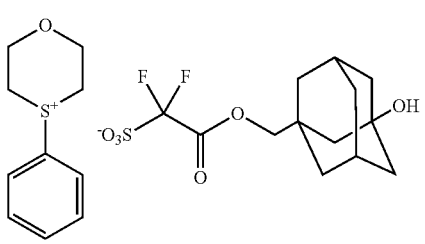
(B1-21)
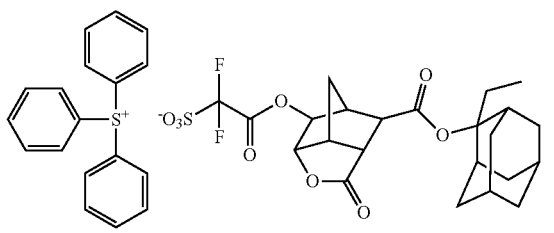
(B1-22)
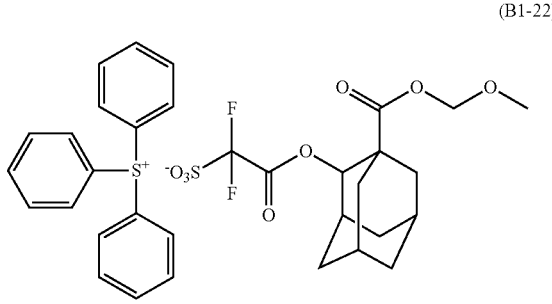

(B1-23)

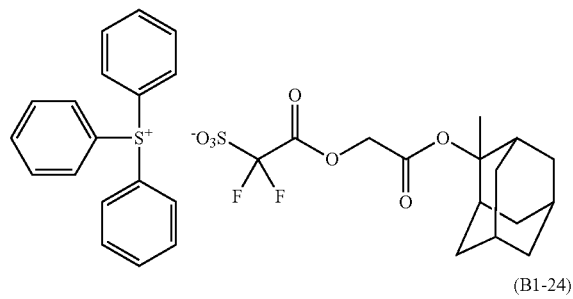

(B1-24)

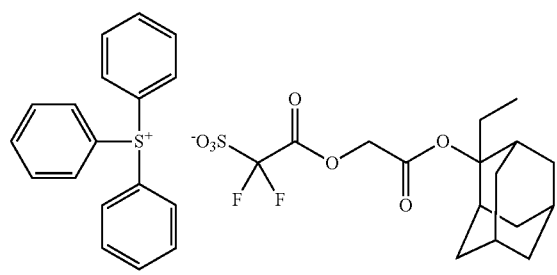

The content of the acid generator is preferably 1 part by mass or more, and more preferably 3 parts by mass or more, per 100 parts by mass of RESIN (A). The content of the acid generator is preferably 40 parts by mass or less, and more preferably 35 parts by mass or less, per 100 parts by mass of RESIN (A).

The photoresist compositions of the present invention can comprise a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine.

Examples of the aromatic amine include an aromatic amine in which an aromatic ring has an amino group, such as aniline, and a heteroaromatic amine such as pyridine.

Preferable examples of the basic compound (C1) include those represented by the formulae (C1), (C2), (C3), (C4), (C5), (C6), (C7) and (C8), (C1)

in which $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxy group, an amino group and a C1-C6 alkoxy group, and the aromatic hydrocarbon group can have a substituent selected from the group consisting of C1-C6 alkyl groups, a C5-C10 alicyclic hydrocarbon group, a hydroxy group, an amino group, and a C1-C6 alkoxy group.

(C2)

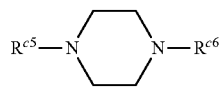

(C3)

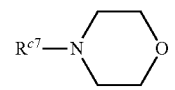

(C4)

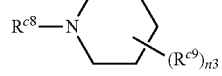

in which $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic hydrocarbon group, or a C2-C6 alkanoyl group, and n3 represents an integer of 0 to 8, (C5)

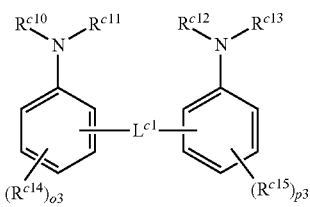

(C6)

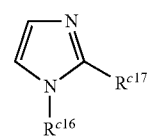

in which each of $R^{c10}$, $R^{c11}$, $R^{c12}$, $R^{c13}$ and $R^{c16}$ is defined same as $R^{c1}$, each of $R^{c14}$, $R^{c15}$ and $R^{c17}$ is defined same as $R^{c4}$, $L^{c1}$ represents a C1-C6 alkanediyl group, —CO—, —C(=NH)—, —S— or a combination thereof, and o3 and p3 respectively represent an integer of 0 to 3, (C7)

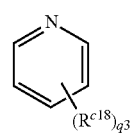

(C8)

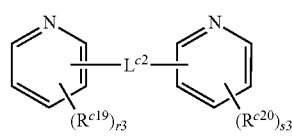

in which each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

The alkyl groups, alicyclic hydrocarbon groups, aromatic hydrocarbon groups, alkoxy groups and alkanediyl groups for the substituents of the formulae (C1) to (C8) include those as mentioned above. The alkanoyl group for the substituents of the formulae (C1) to (C8) includes an acetyl group, 2-methylacetyl group, 2,2'-dimethylacetyl group, propyonyl group, butyryl group, isobutyryl group, pentanoyl group, and 2,2-dimethylpropionyl group.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A1.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

Among these basic compounds, the compounds of formula (C1) are preferred.

As the aromatic amine represented by the formula (C1), an amine represented by the formula (C1-1) is preferred;

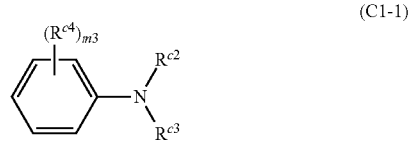

(C1-1)

in which $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3.

When the photoresist compositions comprise the basic compound, the content thereof is preferably 0.01 to 5% by mass, more preferably 0.01 to 3% by mass, still more preferably 0.01 to 1% by mass, based on the total amount of solid component.

The photoresist compositions of the present invention usually comprise a solvent. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by mass or more, preferably 92% by mass or more, preferably 94% by mass or more based on total amount of the photoresist composition of the present invention. The amount of the solvent is usually 99.9% by mass or less based on total amount of the photoresist composition of the present invention.

The photoresist compositions of the present invention can comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, generally in a solvent, an acid generator and RESIN (A), and if necessary a basic compound and/or additives at a suitable ratio for the composition, optionally followed by filtrating the mixture with a filter having from 0.003 to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

A photoresist pattern can be produced by the following steps (1) to (5):

(1) a step of applying the photoresist composition of the present invention on a substrate, (2) a step of forming a photoresist film by conducting drying the photoresist composition, (3) a step of exposing the photoresist film to radiation, (4) a step of heating the exposed photoresist film, and (5) a step of developing the heated photoresist film.

The applying of the photoresist composition on a substrate is usually conducted using a conventional apparatus such as spin coater. The photoresist composition is preferably filtrated with filter having a pore size of 0.003 to 0.2 μm before applying. Examples of the substrate include a silicon wafer or a quartz wafer on which a sensor, a circuit, a transistor or the like may be formed. The substrate may be coated with a reflect-preventing layer such as one containing hexamethyldisilazane before applying the photoresist composition of the present invention. For forming the reflect-preventing layer, such composition for organic reflect-preventing layer as available on the market can be used.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of heating of the exposed photoresist film is usually 50 to 200° C., and preferably 70 to 150° C.

The development of the heated photoresist film is usually carried out using a development apparatus. The development can be carried out in manner of known methods such as dipping, paddle, spray, or dynamic dispense method. The temperature of development is preferably 5 to 60° C. The time for development is usually 5 to 300 seconds.

The photoresist composition can provide positive or negative photoresist pattern. Each type of the pattern can be selectively made by development with a developer capable of providing desired pattern.

When a positive photoresist pattern is made from the photoresist composition of the present invention, an alkaline developer may be employed as a developer. The alkaline developer to be used may be any one of various alkaline aqueous solution used in the art.

Generally, an aqueous solution of tetramethylammonium hydroxide or (2-hydroxyethyl)trimethylammonium hydroxide (commonly known as "choline") is often used. The alkaline developer may contain a surfactant.

After development, the formed photoresist pattern is preferably washed with ultrapure water, and the remained water on the photoresist pattern and the substrate is preferably removed.

When a negative photoresist pattern is made from the photoresist composition of the present invention, organic solvent-containing developers may be employed as a developer.

The organic solvent for the developers includes ketone solvents such as 2-hexanone or 2-heptanone; glycoletherester solvents such as propyleneglycolmonomethylether acetate; ester solvents such as butyl acetate; glycolether solvents such as propyleneglycolmonomethylether; amide solvents such as N,N-dimethylacetoamide; and aromatic hydrocarbon solvents such as anisole.

The organic solvent-containing developer preferably comprises butyl acetate, 2-heptanone, or both of them.

When the organic solvent-containing developer comprises butyl acetate and 2-heptanone, the total content of them is preferably 50 to 100% by mole, more preferably 90 to 100% by mole, and the developer still more preferably consists substantially of butyl acetate and 2-heptanone.

The organic solvent-containing developer may comprise surfactants or water.

The content of the organic solvent in the organic solvent-containing developer is preferably 90 to 100% by mole, more preferably 95 to 100% by mole. The organic solvent-containing developer still more preferably consists of organic solvents.

Development can be stopped by replacing the organic solvent-containing developer by another solvent.

The negative-type photoresist pattern after development is preferably washed with solvents in which the pattern is not dissolved.

The solvents for this washing include alcohol solvents or ester solvents. It is preferred that the solvents on the substrate or the pattern are removed therefrom after washing them.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" represent the content of any component and the amount of any material used in the following examples and comparative examples are on a mass basis unless otherwise specifically noted.

The structure of the compounds was determined by mass spectrometry with Agilent type 1100 [Agilent Technologies; equipped with LC part and LC/MCD part].

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material.

Example 1

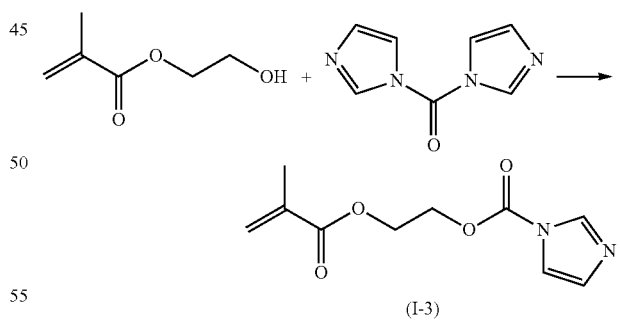

(I-3)

Into a reactor, added were 20 parts of 2-hydroxyethyl 2-methylpropenoate and 240 parts of chloroform. The resultant mixture was stirred at 23° C. for 30 minutes. To the mixture, 27.41 parts of 1,1'-carbonyldiimidazole was added and then stirred at 23° C. for 2 hours. To the resulting mixture, 60 parts of ion-exchanged water was added and then stirred for 30 minutes, followed by separating an organic layer therefrom. Such washing was conducted 6 times.

The collected organic layer was concentrated to obtain 33.46 parts of the compound represented by the formula (I-3).

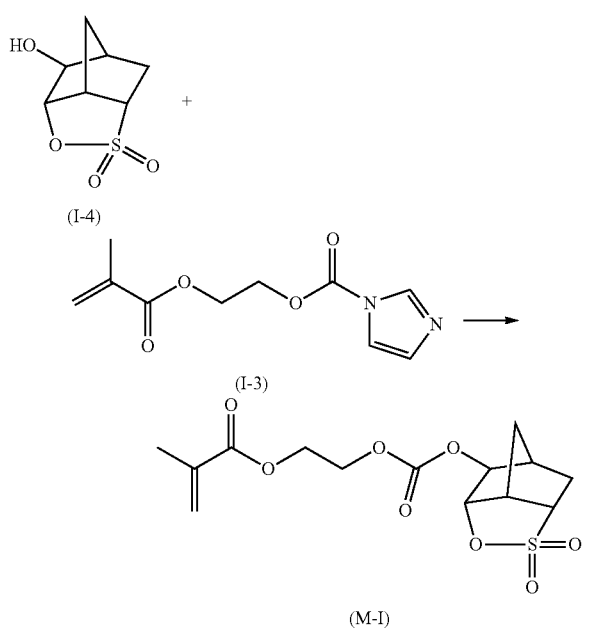

Into a reactor, fed were 1.9 parts of the compound represented by the formula (I-4) and 20 parts of acetonitrile, followed by stirring them at 23° C. for 30 minutes. Thereto 2.24 parts of the compound represented by the formula (I-3) was added and then heated to 50° C., followed by stirring them at the same temperature for 3 hours. To the resulting reaction mixture, 50 parts of chloroform and 20 parts of ion-exchanged water were added and then stirred at 23° C. for 30 minutes, followed by setting it still to separate an organic layer therefrom. The collected organic layer was washed with 20 parts of ion-exchanged water and then stirred at 23° C. for 30 minutes to separate an organic layer therefrom. Such washing with ion-exchanged water was conducted 5 times.

The washed organic layer was concentrated. The concentrates were purified with column chromatography (silica gel 60 to 200 mesh, manufactured by Merck, solvent: ethyl acetate) to obtain 2.21 parts of the compound represented by the formula (M-I).

MS: 346.1 (molecular ion peak)

Example 2

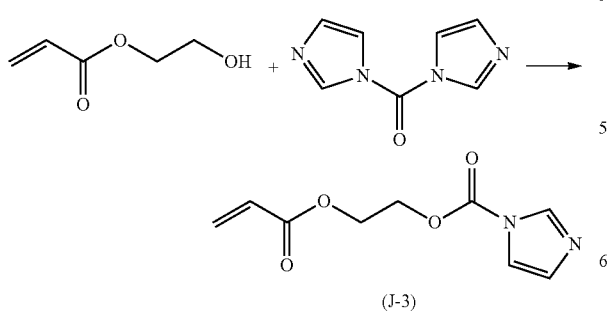

Into a reactor, added were 20 parts of 2-hydroxyethyl propenoate and 240 parts of chloroform. The resultant mixture was stirred at 23° C. for 30 minutes. To the mixture, 30.71 parts of 1,1'-carbonyldiimidazole was added and then stirred at 23° C. for 2 hours. To the resulting mixture, 60 parts of ion-exchanged water was added and then stirred for 30 minutes, followed by separating an organic layer therefrom. Such washing was conducted 6 times.

The collected organic layer was concentrated to obtain 34.88 parts of the compound represented by the formula (J-3).

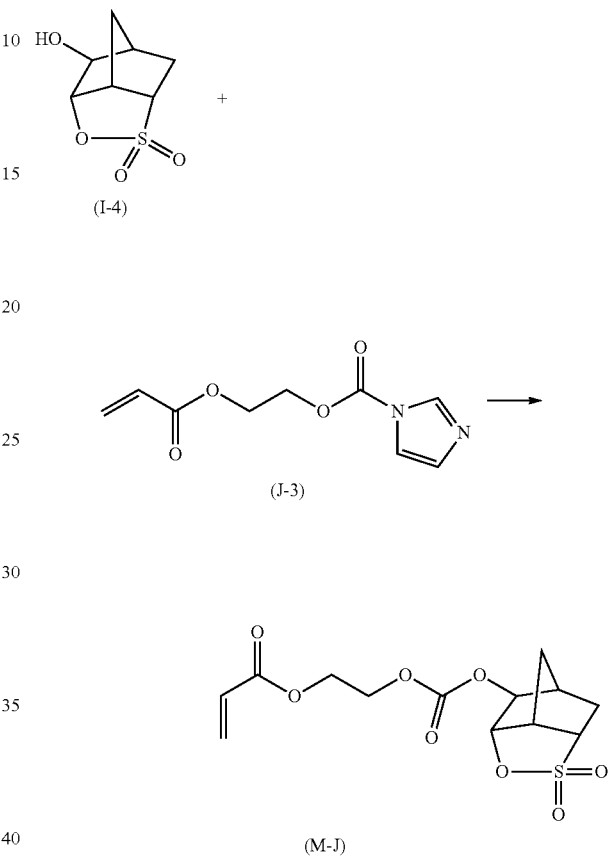

Into a reactor, fed were 1.9 parts of the compound represented by the formula (I-4) and 20 parts of acetonitrile, followed by stirring them at 23° C. for 30 minutes. Thereto 2.24 parts of the compound represented by the formula (J-3) was added and then heated to 50° C., followed by stirring them at the same temperature for 3 hours. To the resulting reaction mixture, 50 parts of chloroform, 20 parts of ion-exchanged water were added and then stirred at 23° C. for 30 minutes, followed by setting it still to separate an organic layer therefrom. The collected organic layer was washed with 20 parts of ion-exchanged water and then stirred at 23° C. for 30 minutes to separate an organic layer therefrom. Such washing with ion-exchanged water was conducted 5 times.

The washed organic layer was concentrated. The concentrates were purified with column chromatography (silica gel 60 to 200 mesh, manufactured by Merck, solvent: ethyl acetate) to obtain 2.02 parts of the compound represented by the formula (M-J).

MS: 332.1 (molecular ion peak)

Monomers used in Examples are the compounds represented by formulae (M-A), (M-B), (M-C), (M-D), (M-E), (M-F), (M-G), (M-H), (M-I), (M-J) and (M-K). Hereinafter, these monomers are briefly referred to as "monomer X" where X represents the symbol of formula corresponding to the monomer.

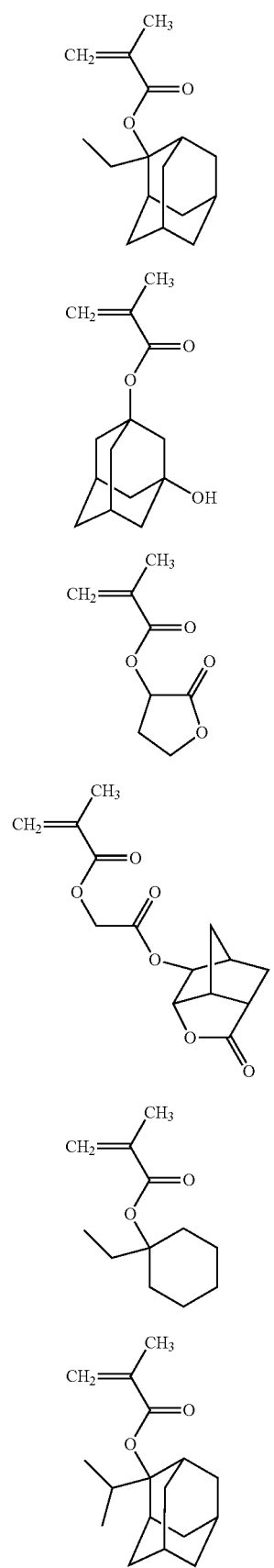 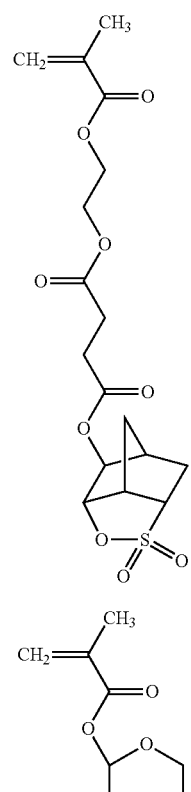 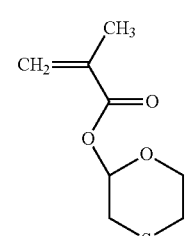 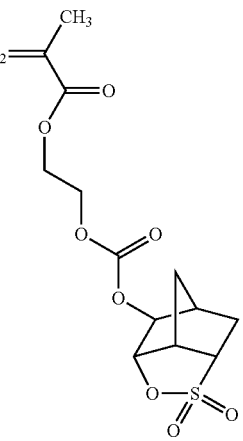 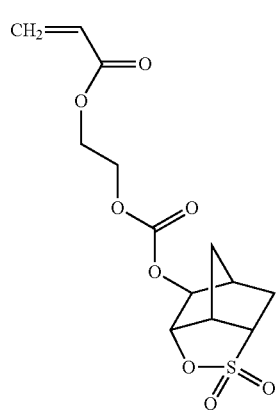

-continued

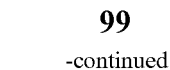
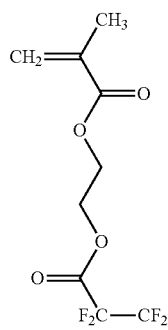

(M-K)

Example 3

The monomers (M-A), (M-E), (M-B), (M-D), (M-C) and (M-I) were mixed in a molar ratio of 30/14/6/10/30/10 [monomer (M-A)/monomer (M-E)/monomer (M-B)/monomer (M-D)/monomer (M-C)/monomer (M-I)], and 1,4-dioxane in 1.5 times part based on total parts of all monomers was added thereto to prepare a solution.

To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The obtained reaction mixture was poured into a large amount of a mixture of methanol and water to cause precipitation. The precipitate was collected by filtration and then, was dissolved in 1,4-dioxane followed by pouring the resultant solution into a large amount of a mixture of methanol and water to cause precipitation. This operation was conducted twice for purification. As a result, a resin having a weight-average molecular weight of about $7.9 \times 10^3$ was obtained in a yield of 82%. This resin is called as resin A1. The resin A1 has the following structural units.

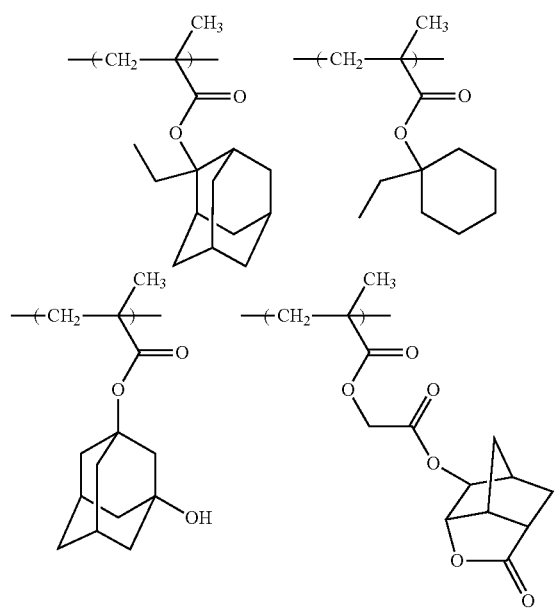

-continued

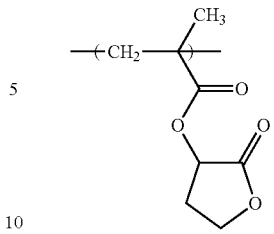
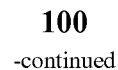
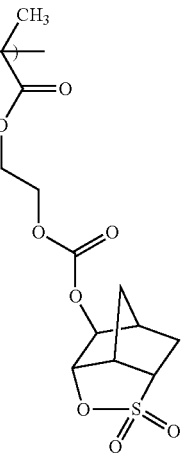

Example 4

The monomers (M-A), (M-H), (M-B), (M-D), (M-C) and (M-I) were mixed in a molar ratio of 30/14/6/10/30/10 (monomer (M-A)/monomer (M-H)/monomer (M-B)/monomer (M-D)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The obtained reaction mixture was poured into a large amount of a mixture of methanol and water to cause precipitation.

The precipitate was collected by filtration and then, was dissolved in 1,4-dioxane, followed by pouring the resultant solution into a large amount of a mixture of methanol and water to cause precipitation.

This operation was conducted twice for purification. As a result, a resin having a weight-average molecular weight of about $7.8 \times 10^3$ was obtained in a yield of 84%. This resin is called as resin A2. Resin A2 had the following structural units.

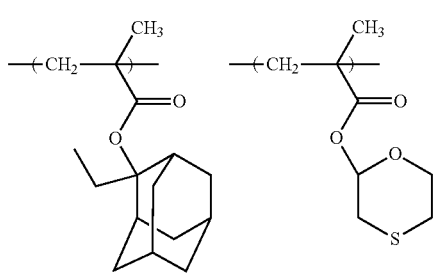

101

-continued

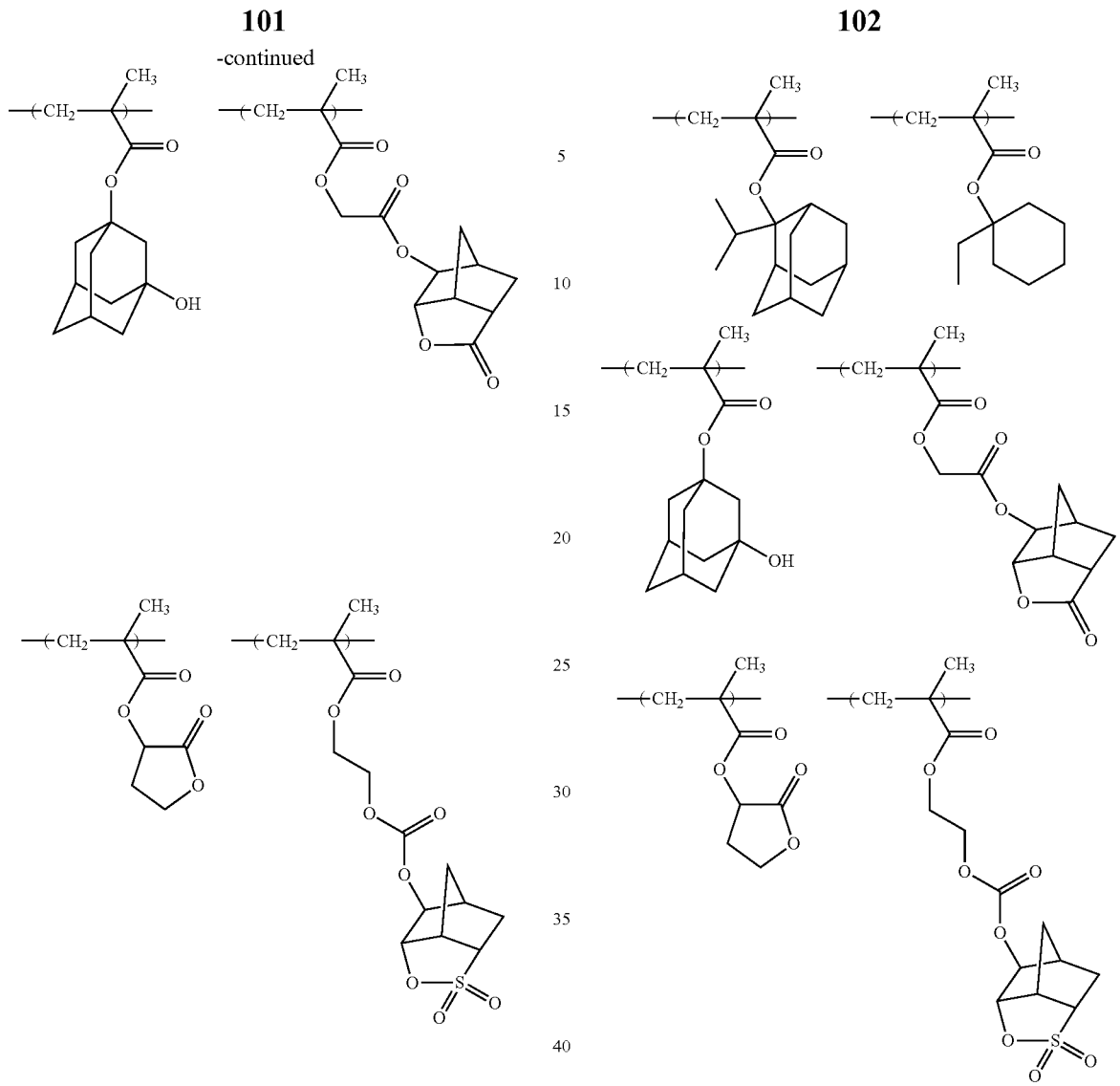

102

Example 5

The monomers (M-F), (M-E), (M-B), (M-D), (M-C) and (M-I) were mixed in a molar ratio of 30/14/6/10/30/10 (monomer (M-F)/monomer (M-E)/monomer (M-B)/monomer (M-D)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The obtained reaction mixture was poured into a large amount of a mixture of methanol and water to cause precipitation.

The precipitate was collected by filtration and then, was dissolved in 1,4-dioxane followed by pouring the resultant solution into a large amount of a mixture of methanol and water to cause precipitation.

This operation was conducted twice for purification. As a result, a resin having a weight-average molecular weight of about $7.3 \times 10^3$ was obtained in a yield of 68%. This resin is called as resin A3. Resin A3 had the following structural units.

Resin Synthesis Example 1

The monomers (M-A), (M-B) and (M-G) were mixed in a molar ratio of 53/17/30 (monomer (M-A)/monomer (M-B)/monomer (M-G)), and 1,4-dioxane in 1.5 times part based on total parts of all monomers was added to prepare a solution. To the solution, azobisisobutyronitrile as an initiator in a ratio of 1 mol % based on all monomer molar amount and azobis (2,4-dimethylvaleronitrile) as an initiator in a ratio of 3 mol % based on all monomer molar amount were added, and the obtained mixture was heated at 80° C. for about 5 hours. The obtained reaction mixture was poured into a large amount of a mixture of methanol and water to cause precipitation.

The precipitate was collected by filtration and then, was dissolved in 1,4-dioxane followed by pouring the resultant solution into a large amount of a mixture of methanol and water to cause precipitation.

This operation was conducted twice for purification. As a result, a resin having a weight-average molecular weight of about $7 \times 10^3$ was obtained in a yield of 80%. This resin is called as resin A4.

Resin A4 had the following structural units.

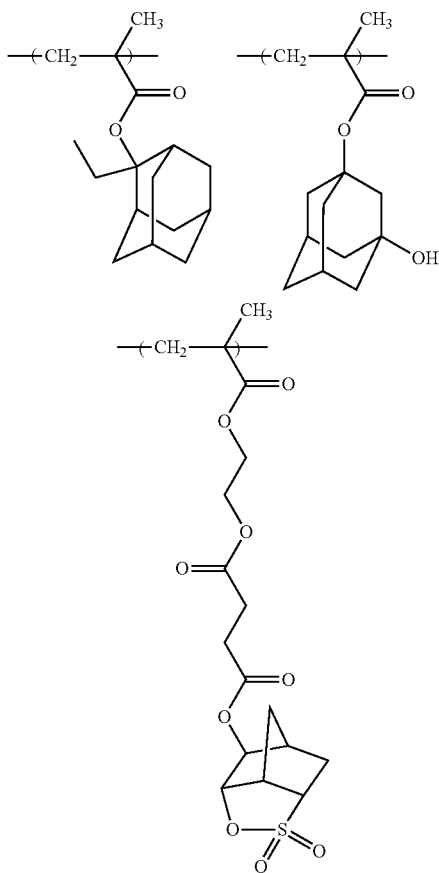

Example 6

The monomers (M-A), (M-H), (M-B), (M-D), (M-C) and (M-J) were mixed in a molar ratio of 30/14/6/10/30/10 (monomer (M-A)/monomer (M-H)/monomer (M-B)/monomer (M-D)/monomer (M-C)/monomer (M-J)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The obtained reaction mixture was poured into a large amount of a mixture of methanol and water to cause precipitation.

The precipitate was collected by filtration and then, was dissolved in 1,4-dioxane followed by pouring the resultant solution into a large amount of a mixture of methanol and water to cause precipitation.

This operation was conducted twice for purification. As a result, a resin having a weight-average molecular weight of about $8.3 \times 10^3$ was obtained in a yield of 87%. This resin is called as resin A5. Resin A5 had the following structural units.

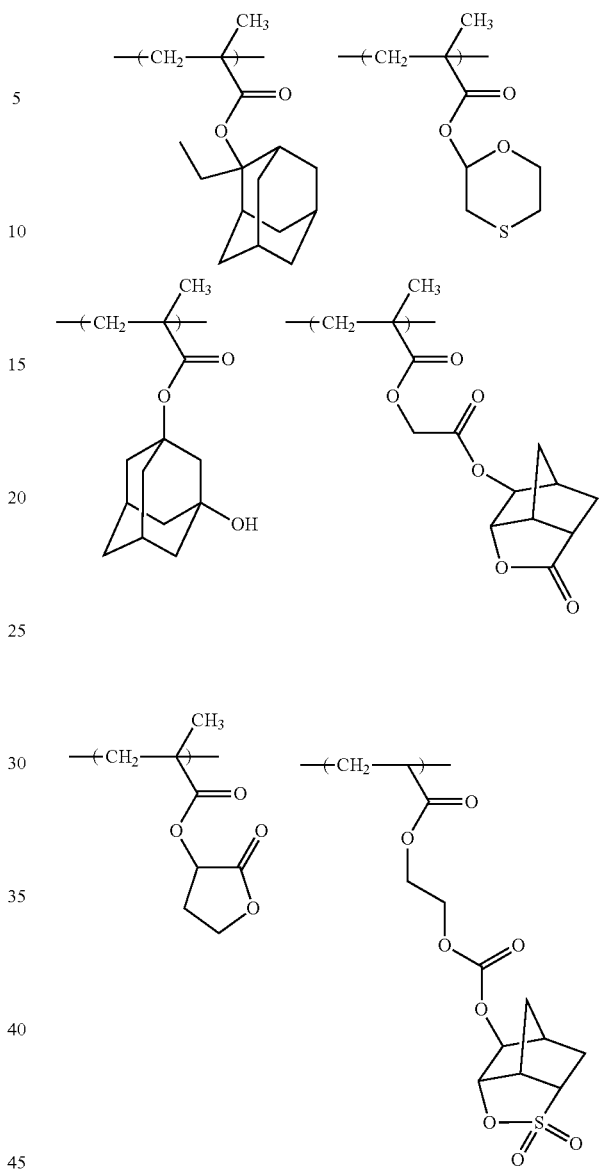

Resin Synthesis Example 2

The monomer (M-K) and 1,4-dioxane in 1.5 times part based on total parts of the monomer were fed into a reactor to prepare a solution. To the solution, azobisisobutyronitrile as an initiator in a ratio of 0.7 mol % based on the monomer molar amount and azobis(2,4-dimethylvaleronitrile) as an initiator in a ratio of 2.1 mol % based on the monomer molar amount were added, and the obtained mixture was heated at 75° C. for about 5 hours. The obtained reaction mixture was poured into a large amount of a mixture of methanol and water to cause precipitation. The precipitate was collected by filtration and then, was dissolved in 1,4-dioxane followed by pouring the resultant solution into a large amount of a mixture of methanol and water to cause precipitation. This operation was conducted twice for purification. As a result, a resin having a weight-average molecular weight of about $1.8)<10^4$ was obtained in a yield of 77%. This resin is called as resin X1.

Resin X1 had the following structural unit.

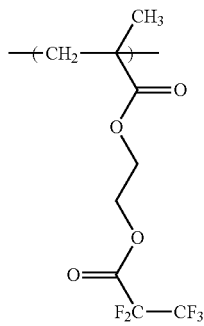

Examples 7 to 14 and Comparative Example 1

Resin, acid generator, quencher and solvent as follow were mixed and dissolved. Then the obtained mixture was filtrated through a fluorine resin filter having pore diameter of 0.2 μm, to prepare photoresist compositions.
Resin: kind and amount are described in Table 1
Resins A1, A2, A3, A4, A5
Acid generator: kind and amount are described in Table 1
B1: The salt as follows, made by the method described in JP2010-152341.

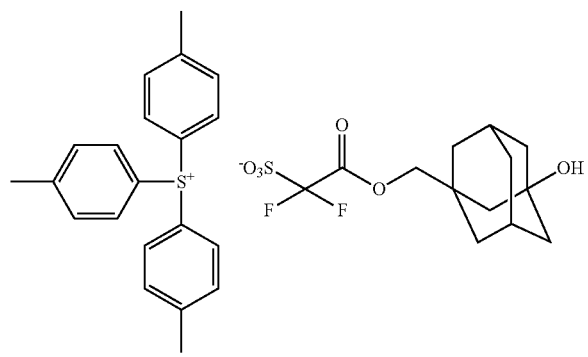

B2: The salt as follows, made by the method described in JP2010-164712.

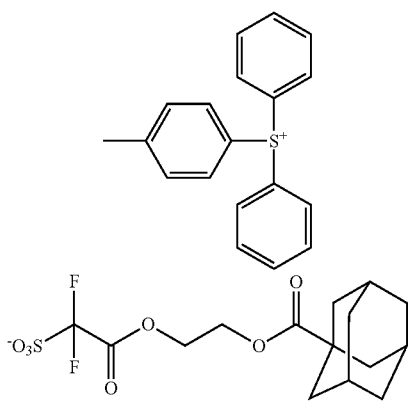

Quencher: kind and amount are described in Table 1
C1: 2,6-diisopropylaniline

<Solvent>

| E1: propylene glycol monomethyl ether acetate | 265 parts |
| propylene glycol monomethyl ether | 20 parts |
| 2-heptanone | 20 parts |
| γ-butyrolactone | 3.5 parts |

TABLE 1

| Ex. No. | Resin (kind/amount (part)) | Acid generator (kind/amount (part)) | Quencher (kind/amount (part)) | PB (° C.) | PEB (° C.) |
| --- | --- | --- | --- | --- | --- |
| Ex. 7 | A1/10 | B1/1.1 | C1/0.07 | 110 | 100 |
| Ex. 8 | A2/10 | B1/1.1 | C1/0.07 | 110 | 100 |
| Ex. 9 | A3/10 | B1/1.1 | C1/0.07 | 100 | 90 |
| Ex. 10 | A1/10 | B2/1.1 | C1/0.07 | 110 | 100 |
| Ex. 11 | A1/10 X1/0.7 | B1/1.1 | C1/0.07 | 110 | 100 |
| Ex. 12 | A2/10 X1/0.7 | B1/1.1 | C1/0.07 | 110 | 100 |
| Ex. 13 | A3/10 X1/0.7 | B1/1.1 | C1/0.07 | 100 | 90 |
| Ex. 14 | A5/10 X1/0.7 | B1/1.1 | C1/0.07 | 110 | 100 |
| Comp. Ex. 1 | A4/10 | B2/1.1 | C1/0.07 | 110 | 100 |

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each pre-baked on a direct hotplate at a temperature shown in the column "PB" in Table 1 for 60 seconds. Using an ArF excimer stepper for immersion exposure ("XT: 1900Gi" manufactured by ASML, NA=1.35, 3/4 Annular, X-Y polarization), each wafer thus formed with the respective resist film was subjected to line and space pattern exposure with the exposure quantity being varied stepwise. Ultrapure water was used as an immersion medium.

After the exposure, each wafer was subjected to post-exposure heating on a hotplate at a temperature shown in the column "PEB" in Table 1 for 60 seconds and then to paddle development for 60 seconds with an aqueous solution of 2.38% by mass tetramethylammonium hydroxide.

<Evaluation>

The photoresist patterns were obtained at the exposure quantity of effective sensitivity, with the focal point distance being varied stepwise.

Here, the effective sensitivity (ES) was expressed as the exposure quantity that the line widths of the pattern became 50 nm after exposure and development through line and space pattern mask of 50 nm line width.

Each of patterns developed on the organic anti-reflective coating substrate after the development was observed. The focal point distances when the line widths of the pattern were within 50 nm±5% (between 47.5 nm and 52.5 nm) were measured, and the difference between the max value of the focal point distance and the minimum value of the focal point distance was calculated, which difference was defined as Focus margin (DOF).

The larger is DOF, the finer pattern can be made from the photoresist composition.

TABLE 2

| Ex. No. | DOF (μm) |
| --- | --- |
| Ex. 7 | 0.21 |
| Ex. 8 | 0.21 |
| Ex. 9 | 0.18 |
| Ex. 10 | 0.15 |
| Ex. 11 | 0.21 |
| Ex. 12 | 0.21 |
| Ex. 13 | 0.18 |
| Ex. 14 | 0.24 |
| Compar. Ex. 1 | 0.09 |

The resin of the present invention can provide a photoresist composition which can finely make a photoresist pattern. Therefore, the resin and the photoresist composition are highly available for a lithography process of semiconductor microfabrication.

What is claimed is:

1. A resin comprising a structural unit represented by formula (aa):

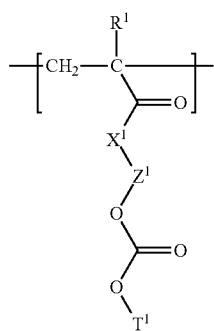

(aa)

wherein $T^1$ represents a group represented by the formula (T1), $X^1$ represents —O— or —N($R^c$)—, $R^c$ represents a hydrogen atom or a C1-C6 alkyl group, $Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)—, and $R^d$ represents a hydrogen atom or a C1-C6 alkyl group, and $R^1$ represents a hydrogen atom, a halogen atom, or a C1-C6 alkyl group optionally having a halogen atom:

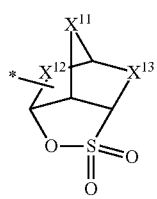

(T1)

wherein $X^{11}$, $X^{12}$ and $X^{13}$ independently each represent —O—, —S— or —CH$_2$—, a hydrogen atom in —CH$_2$— in the formula (T1) may be replaced by a halogen atom, a hydroxyl group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group or a C2-C4 acyl group, and * represents a binding position to —O—.

2. The resin according to claim 1, which is insoluble or poorly soluble in an aqueous alkali solution but becoming soluble in an aqueous alkali solution by the action of an acid.

3. A photoresist composition which comprises an acid generator and the resin according to claim 1.

4. A process for producing a photoresist pattern comprising:
   (1) a step of applying the photoresist composition according to claim 3 on a substrate to form a photoresist composition layer,
   (2) a step of forming a photoresist film by drying the photoresist composition layer,
   (3) a step of exposing the photoresist film to radiation,
   (4) a step of heating the photoresist film after exposing, and
   (5) a step of developing the heated photoresist film.

5. The photoresist composition according to claim 3 which further comprises a resin having not an acid-labile group but a fluorine atom.

6. The photoresist composition according to claim 5, wherein the resin having not an acid-labile group but a fluorine atom comprises a structural unit derived from a monomer represented by formula (a4-1):

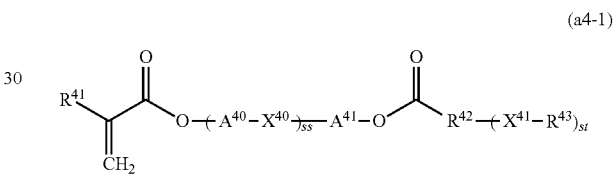

(a4-1)

wherein $R^{41}$ represents a hydrogen atom or a methyl group, $A^{40}$ and $A^{41}$ each independently represent a C1-C6 divalent aliphatic hydrocarbon group, $X^{40}$ represents —O—, —CO— or —CO—O—, $R^{42}$ represents a C1-C18 aliphatic hydrocarbon group which may be substituted with a fluorine atom and $R^{43}$ represents a C1-C17 monovalent aliphatic hydrocarbon group which may be substituted with a fluorine atom, provided that one or both aliphatic hydrocarbon groups of $R^{42}$ and $R^{43}$ have a fluorine atom, $X^{41}$ represents —CO—O—, ss represents an integer of 0 to 2, and st represents an integer of 0 to 3.

7. The photoresist composition according to claim 6, wherein the monomer represented by formula (a4-1) is represented by formula (a4-1'):

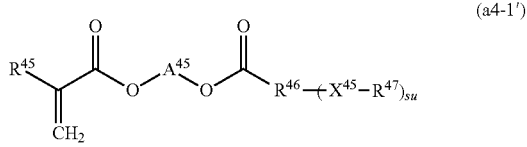

(a4-1')

wherein $R^{45}$ represents a hydrogen atom or a methyl group, $A^{45}$ represents a C1-C6 divalent aliphatic hydrocarbon group, $R^{46}$ represents a C1-C18 aliphatic hydrocarbon group which may be substituted with a fluorine atom and $R^{47}$ represents a C1-C17 aliphatic hydrocarbon group which may be substituted with a fluorine atom, provided that one or both aliphatic hydrocarbon groups of $R^{46}$ and $R^{47}$ have a fluorine atom, $X^{45}$ represents —CO—O—, and su represents an integer of 0 to 1.

8. A compound represented by formula (aa'):

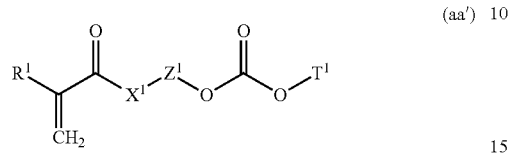

wherein $T^1$ represents a C3-C34 sultone ring group optionally having a substituent, $X^1$ represents —O— or —N($R^c$)—, $R^c$ represents a hydrogen atom or a C1-C6 alkyl group, $Z^1$ represents —$X^2$— or —$X^3$—$X^4$—CO—$X^5$—, where $X^2$, $X^3$ and $X^5$ independently each represent a C1-C6 alkanediyl group, $X^4$ represents —O— or —N($R^d$)—, and $R^d$ represents a hydrogen atom or a C1-C6 alkyl group, and $R^1$ represents a hydrogen atom, a halogen atom, or a C1-C6 alkyl group optionally having a halogen atom.

9. The compound according to claim 8, wherein $T^1$ is a C4-C34 sultone ring group optionally having a substituent.

* * * * *